US008865159B2

(12) United States Patent
Mittal et al.

(10) Patent No.: US 8,865,159 B2
(45) Date of Patent: Oct. 21, 2014

(54) TREATMENT OF TUMORS BY ABLATING BONE MARROW-DERIVED ENDOTHELIAL PROGENITOR CELLS

(75) Inventors: Vivek Mittal, Greenlawn, NY (US); Daniel J. Nolan, Franklin Square, NY (US); Dingcheng Gao, Rego Park, NY (US); Albert S. Mellick, Huntington, NY (US)

(73) Assignee: Cold Spring Harbor Laboratory, Cold Spring Harbor, NY (US)

( * ) Notice: Subject to any disclaimer, the term of this patent is extended or adjusted under 35 U.S.C. 154(b) by 1343 days.

(21) Appl. No.: 12/522,093

(22) PCT Filed: Jan. 4, 2008

(86) PCT No.: PCT/US2008/000214
§ 371 (c)(1),
(2), (4) Date: Jun. 17, 2010

(87) PCT Pub. No.: WO2008/085951
PCT Pub. Date: Jun. 17, 2008

(65) Prior Publication Data
US 2010/0284907 A1 Nov. 11, 2010

Related U.S. Application Data

(60) Provisional application No. 60/878,949, filed on Jan. 4, 2007, provisional application No. 60/934,846, filed on Jun. 14, 2007.

(51) Int. Cl.
| | | |
|---|---|---|
| *A61K 35/14* | (2006.01) | |
| *C12N 5/0789* | (2010.01) | |
| *C12N 15/86* | (2006.01) | |
| *A61K 48/00* | (2006.01) | |
| *C07K 16/28* | (2006.01) | |
| *C12N 15/113* | (2010.01) | |

(52) U.S. Cl.
CPC ............ *C07K 16/2896* (2013.01); *C12N 15/86* (2013.01); *C12N 2830/008* (2013.01); *A61K 48/0058* (2013.01); *C12N 2740/15043* (2013.01); *C12N 15/113* (2013.01); *C12N 15/1136* (2013.01); *C12N 2310/14* (2013.01); *A61K 48/005* (2013.01)
USPC ........................................ 424/93.7; 435/372

(58) Field of Classification Search
None
See application file for complete search history.

(56) References Cited

U.S. PATENT DOCUMENTS

2003/0232050 A1* 12/2003 Isner et al. ................. 424/144.1
2004/0141916 A1* 7/2004 Sgouros ....................... 424/1.49

FOREIGN PATENT DOCUMENTS

WO WO 2005/120090 12/2005
WO WO 2006/060779 6/2006

OTHER PUBLICATIONS

Satyanarayana et al, FASEB Journal, 2012, vol. 26, pp. 309-323.*
Hoelzle et al Molecular Biology of the Cell, 2012, vol. 23, pp. 310-323.*
Minna et al, Stem Cells, 2008, vol. 26, pp. 2696-2704.*
Arbab et al (Stem Cells, first published on-line Sep. 22, 2005, vol. 24, pp. 671-678).*
Liao et al (Cancer Research, 2002, vol. 62, pp. 2567-2575).*
Wei et al (Cancer Cell, 2004, vol. 5, pp. 477-488).*
International Search Report dated Mar. 12, 2008 for PCT/US2008/000214.
Lyden et al. "Impaired recruitment of bone-marrow-derived endothelial and hematopoietic precursor cells blocks tumor angiogenesis and growth." *Nat Med.* Nov. 2001;7(11):1194-201.
Shaked et al. "Therapy-induced acute recruitment of circulating endothelial progenitor cells to tumors." *Science.* Sep. 22, 2006;313(5794):1785-7.
Jiang et al. "Inhibition of hypoxia-inducible factor-1alpha and endothelial progenitor cell differentiation by adenoviral transfer of small interfering RNA in vitro." *J Vasc Res.* 2006;43(6):511-21. Epub Sep. 27, 2006.
Wei et al. "Embryonic endothelial progenitor cells armed with a suicide gene target hypoxic lung metastases after intravenous delivery." *Cancer Cell.* May 2004;5(5):477-88.
Gomez-Navarro et al. "Genetically modified CD34+ cells as cellular vehicles for gene delivery into areas of angiogenesis in a rhesus model." *Gene Ther.* Jan. 2000;7(1):43-52.
Database Biosis Biosciences Information Service, Database accession No. PREV200700245081, Downloaded Oct. 29, 2008.
Colleselli et al. "Inhibition of cyclooxygenase (COX)-2 affects endothelial progenitor cell proliferation." *Exp Cell Res.* Sep. 10, 2006 ;312(15):2933-41. Epub Jun. 14, 2006.
Furstenberger et al. "Circulating endothelial cells and angiogenic serum factors during neoadjuvant chemotherapy of primary breast cancer.:" *Br J Cancer.* Feb. 27, 2006;94(4):524-31.
Ribatti, "The involvement of endothelial progenitor cells in tumor angiogenesis." *J Cell Mol Med.* Jul.-Sep. 2004;8(3):294-300.
Milkiewicz et al. "Regulators of angiogenesis and strategies for their therapeutic manipulation." *Int J Biochem Cell Biol.* Mar. 2006;38(3):333-57.
Zammaretti "Adult 'endothelial progenitor cells'. Renewing vasculature. " *Int J Biochem Cell Biol.*Mar. 2005;37(3):493-503.
Rafii et al. "Vascular and haematopoietic stem cells: novel targets for anti-angiogenesis therapy?" *Nat Rev Cancer.* Nov. 2002;2(11):826-35.

(Continued)

*Primary Examiner* — Karen Canella
(74) *Attorney, Agent, or Firm* — Wolf, Greenfield & Sacks, P.C.

(57) ABSTRACT

This invention provides methods of treating tumors and other conditions characterized by abnormal neoangiogenesis by inhibiting bone marrow-derived endothelial progenitor cells.

8 Claims, 36 Drawing Sheets

(56) References Cited

OTHER PUBLICATIONS

Masuda and Asahara "Post-natal endothelial progenitor cells for neovascularization in tissue regeneration." *Cardiovasc Res.* May 1, 2003;58(2):390-8.

Verheul and Pinedo "Vascular Endothelial Growth Factor and its Inhibitors" Durgs of Today 39(C) 2003 81-93.

"Hicklin and Ellis" Role of the vascular endothelial growth factor pathway in tumor growth and angiogenesis. *J Clin Oncol.* Feb. 10, 2005;23(5):1011-27.

* cited by examiner

TREATMENT OF TUMORS BY ABLATING BONE MARROW-DERIVED ENDOTHELIAL PROGENITOR CELLS

RELATED APPLICATIONS

This application is a national stage filing under 35 U.S.C. 371 of International Application PCT/US2008/000214 designating the United States of America, and filed Jan. 4, 2008. This application claims the benefit under 35 U.S.C. §119(e) of U.S. provisional application No. 60/878,949, filed Jan. 4, 2007 and U.S. provisional application No. 60/934,846, filed Jun. 14, 2007, both of which are incorporated by reference herein. International Application PCT/US2008/000214 was published under PCT Article 21(2) in English.

This invention was made with government support under Grant No. 1RO1-CA100933-01A1, awarded by the National Institutes of Health and under Grant No. 1 R01CA107429-01, awarded by the National Institutes of Health. The government has certain rights in the invention.

BACKGROUND OF THE INVENTION

The angiogenic switch involves the formation of new blood vessels (neovasculature), and is a hallmark of cancer emergence and progression (Folkman, N Engl J Med 285, 1182 (1971); Hanahan and Folkman, Cell 86, 353 (1996); Carmeliet and Jain, Nature 407, 249 (2000)). In adults, neovasculature formation relies on the sprouting and cooption of proliferating endothelial cells from adjacent preexisting host vasculature. More recent investigations suggest that the adult bone marrow (BM) is a source of cells that contribute significantly to postnatal angiogenesis (Kopp et al. Curr Opin Hematol 13, 175 (2006); Carmeliet, Nature 438, 932 (2005)). Of the BM-derived cells, much focus has been directed on the proangiogenic hematopoietic mural cells that are recruited to the perivascular sites within the tumor bed (Kopp et al., Curr Opin Hematol 13, 175 (2006); Carmeliet, Nature 438, 932 (2005); Coussens and Werb, Nature 420, 860 (2002); Pollard, Nat Rev Cancer 4, 71 (2004)). Several populations of BM-derived hematopoietic cells have been reported to contribute to tumor angiogenesis. These include tumor-associated macrophages (TAMs) (Pollard, Nat Rev Cancer 4, 71 (2004); Lin et al., J Exp Med 193, 727 (2001)). Tie2-expressing monocytes (TEMs) (De Palma et al., Cancer Cell 8, 211 (2005)), VEGFR1-positive myeloid progenitors (Lyden et al., Nat Med 7, 1194 (2001)), recruited bone marrow-derived circulating cells (Grunewald et al., Cell 124, 175 (2006)), PDG-FRβ$^+$ pericyte progenitors (Song et al., Nat Cell Biol 7, 870 (2005)), vascular leukocytes (Conejo-Garcia et al., Blood 105:679-681 (2005), and infiltrating neutrophils (Nozawa et al., Proc Natl Acad Sci USA 103, 12493 (2006)).

In addition to the perivascular contribution of BM-derived hematopoietic cells, it has been proposed that the BM-derived endothelial progenitor cells (EPCs) may provide an alternative source of endothelial cells that contribute to neovessel formation (Kopp et al., Curr Opin Hematol 13, 175 (2006); Lyden et al., Nat Med 7, 1194 (2001); Urbich and Dimmeler, Trends Cardiovasc Med 14, 318 (2004); Khakoo and Finkel, Annu Rev Med 56, 79 (2005); Asahara et al., Embo J 18, 3964 (1999); Rafii, et al., Nat Rev Cancer 2, 826 (2002)). However, the true identity of EPCs and their relative contribution to neovasculature formation has been controversial. Extensive variability in EPC contribution to vessel formation has been described. For instance, contribution as high as 50% (Lyden et al., Nat Med 7, 1194 (2001); Garcia-Barros et al., Science 300, 1155 (2003)), to as low as 5-20% (Peters et al., Nat Med 11, 261 (2005); Rajantie et al., Blood 104(7):2084-6 (2004); Machein et al., Brain Pathol 13, 582 (2003)), and in some cases undetectable levels (De Palma et al., Cancer Cell 8, 211 (2005); De Palma et al., Nat Med 9, 789 (2003); Gothert et al., Blood 104, 1769 (2004); Ziegelhoeffer et al., Circ Res 94, 230 (2004); Voswinckel et al., Circ Res 93, 372 (2003); He et al., Cancer Res 64, 3737 (2004)) have been reported. Thus, it remains unclear whether bone marrow-derived EPCs play a significant role in tumor neoangiogenesis and hence serve as a valid target for cancer therapy.

SUMMARY OF THE INVENTION

Using a comprehensive panel of cell surface markers to phenotypically identify EPCs, we have discovered that these cells are recruited to the tumor periphery preceding vessel formation. EPCs differentiate into endothelial cells and incorporate luminally into a subset of sprouting tumor neovessels in various tumors. Selective ablation of EPCs in vivo result in a marked delay in tumor growth associated with distinct vascular defects, demonstrating the functional relevance of these cells in the process of tumor neovascularization. This discovery provides a scientific basis for methods of treating tumors, including: preventing or inhibiting tumor emergence, growth, metastasis (e.g., progression from micrometastases to macrometastases); and preventing or inhibiting neoangiogenesis in rapidly growing tumors, rebounding tumors after chemotherapy, regrowing tumors following incomplete surgical removal of a primary lesion. Furthermore, the invention describes herein encompasses methods of treating tumors by targeting EPCs in combination with existing anti-cancer therapies (e.g. surgical removal, chemotherapy, and radiation therapy).

This invention encompasses a method of inhibiting angiogenesis in a tumor in a subject. This invention further encompasses a method of inhibiting tumor growth or formation in a subject. This invention further encompasses a method of inhibiting progression of micrometastases to macrometastases in a subject. The above-mentioned methods comprises the step of inhibiting bone marrow-derived endothelial progenitor cells (EPCs) in the subject, wherein the EPCs are lin$^-$ bone marrow cells expressing an EPC-specific gene, wherein the EPC-specific gene is an Id1 gene, VEGFR2 gene, or VE-cadherin gene. In some embodiments, the subject is human. In some embodiments, the EPCs are VE-cadherin$^+$ VEGFR2$^+$ CD31$^{low}$ Endoglin$^+$ ProminiI/AC133$^+$ CXCR4$^+$ VLA4$^+$ c-kit$^+$. Is some embodiments, the subject is also treated, either serially or in parallel, with any of the following treatments: surgical removal of tumors, chemotherapy, or radiation therapy. In some embodiments, the inhibiting step comprises inhibiting the growth or differentiation of the EPCs, inhibiting homing of the EPCs to a tumor site, or inhibiting the angiogenic activity of EPCs.

In some embodiments, the inhibiting step comprises administering to the subject an antibody against an EPC-specific cell surface molecule, wherein the antibody is optionally conjugated to a cytotoxin. In some embodiments, the EPC-specific cell surface molecule is monomeric VE-cadherin and the cytotoxin is an alpha-emitting radioactive isotope. In some embodiments, the antibody is E4G10 and the antibody is conjugated to actinium-225.

In some embodiments, the inhibiting step comprises introducing to the bone marrow-derived EPCs a suicide gene, anti-angiogenic gene, or a small interfering RNA molecule against the EPC-specific gene, under transcriptional control of an EPC-specific gene promoter. In some embodiments, the suicide gene is a gene coding for HSV-thymidine kinase, cytosine deaminase (CD), carboxypeptidase G2 (CPG2), purine nucleoside phosphorylase (PNP), nitroreductase (NR), deoxycytidine kinase (dCK), or cytochrome P450 and the anti-angiogenic gene is a gene coding for thrombospondin 1 (TSP1), angiostatin, homeobox (HEX), or Endostatin. In some embodiments, the EPC-specific gene promoter is an Id1 promoter, a VEGFR2 promoter, or a VE-cadherin promoter. In some embodiments, the suicide or anti-angiogenic gene, or the small interfering RNA is introduced to the EPCs using a viral vector, wherein the viral vector is a lentiviral, retroviral, or adenoviral vector. In some embodiments, the introduction step is performed ex vivo.

This invention further encompasses a method of inhibiting tumor growth or formation in a subject, comprising isolating EPCs from the subject, conjugating to the isolated EPCs a cancer therapeutic agent, and implanting the conjugated cells to the subject. In some embodiments, the EPCs are isolated from the subject by flow-cytometry-based cell sorting, magnetic cell sorting, and/or antibody panning, and wherein the EPCs are VE-cadherin$^+$ VEGFR2$^+$ CD31$^{low}$ Endoglin$^+$ Prominin I/AC133$^+$ CXCR4$^+$ VLA4$^+$ c-kit$^+$. In some embodiments, the EPCs are isolated from the bone marrow, peripheral blood, or cord blood of the subject. In some embodiments, the subject is a human. In some embodiments, the subject is also treated, either serially or in parallel, with any of the following treatments: surgical removal of tumors, chemotherapy, or radiation therapy.

This invention further encompasses a composition of substantially purified population of EPCs, wherein the EPCs are VE-cadherin$^+$ VEGFR2$^+$ CD31$^{low}$ Endoglin+ Prominin I/AC133$^+$ CXCR4$^+$ VLA4$^+$ c-kit$^+$. In some embodiments, the EPCs are isolated from the bone marrow, peripheral blood, or cord blood of the subject. In some embodiments, the subject is a human.

This invention further encompasses a method of isolating a population of bone marrow-derived EPCs, comprising isolating cells from a subject, and purifying cells that are VE-cadherin$^+$ VEGFR2$^+$ CD31$^{low}$ Endoglin$^+$ Prominin I/AC133$^+$ CXCR4$^+$ VLA4$^+$ c-kit$^+$ VCAM$^+$ by flow-cytometry-based cell sorting, magnetic cell sorting, and/or antibody panning. In some embodiments, the EPCs are isolated from the bone marrow, peripheral blood, or cord blood of the subject. In some embodiments, the subject is a human.

This invention further encompasses a method of detecting tumor growth in a subject, comprising, isolating EPCs from the subject, labeling the isolated EPCs with a magnetically detectable moiety, scanning the subject by magnetic resonance imaging or positron emission tomography, wherein a higher-than-normal magnetic signal at a site of the subject indicates tumor growth at the site. In some embodiments, the isolating step comprises isolating cells from the bone marrow, peripheral blood, or cord blood of the subject by flow-cytometry-based cell sorting, magnetic cell sorting, and/or antibody panning, wherein the isolated EPCs are VE-cadherin$^+$ VEGFR2$^+$ CD31$^{low}$ Endoglin$^+$ Prominin I/AC133$^+$ CXCR4$^+$ VLA4$^+$ c-kit$^+$. In some embodiments, the subject is a human.

This invention further encompasses a method of treating a condition in a subject characterized by abnormally high rates of neoangiogenesis, for example, age-related macular degeneration, rheumatoid arthritis, psoriasis, or diabetic blindness, comprising the step of inhibiting bone marrow-derived endothelial progenitor cells (EPCs) in the subject, wherein the EPCs are lin$^-$ bone marrow cells expressing an EPC-specific gene, wherein the EPC-specific gene is an Id1 gene, VEGFR2 gene, or VE-cadherin gene. In some embodiments, the subject is human. In some embodiments, the EPCs are VE-cadherin$^+$ VEGFR2+ CD31$^{low}$ Endoglin$^+$ Prominin I/AC133$^+$ CXCR4$^+$ VLA4$^+$ c-kit$^+$. Is some embodiments, the subject is also treated, either serially or in parallel, with any of the following treatments: surgical removal of tumors, chemotherapy, or radiation therapy. In some embodiments, the inhibiting step comprises inhibiting the growth or differentiation of the EPCs, inhibiting homing of the EPCs to a tumor site, or inhibiting the angiogenic activity of EPCs.

In some embodiments, the inhibiting step comprises administering to the subject an antibody against an EPC-specific cell surface molecule, wherein the antibody is optionally conjugated to a cytotoxin. In some embodiments, the EPC-specific cell surface molecule is monomeric VE-cadherin and the cytotoxin is an alpha-emitting radioactive isotope. In some embodiments, the antibody is E4G10 and the antibody is conjugated to actinium-225.

In some embodiments, the inhibiting step comprises introducing to the bone marrow-derived EPCs a suicide gene, anti-angiogenic gene, or a small interfering RNA molecule against the EPC-specific gene, under transcriptional control of an EPC-specific gene promoter. In some embodiments, the suicide gene is a gene coding for HSV-thymidine kinase, cytosine deaminase (CD), carboxypeptidase G2 (CPG2), purine nucleoside phosphorylase (PNP), nitroreductase (NR), deoxycytidine kinase (dCK), or cytochrome P450 and the anti-angiogenic gene is a gene coding for thrombospondin 1 (TSP1), angiostatin, homeobox (HEX), or Endostatin. In some embodiments, the EPC-specific gene promoter is an Id1 promoter, a VEGFR2 promoter, or a VE-cadherin promoter. In some embodiments, the suicide or anti-angiogenic gene, or the small interfering RNA is introduced to the EPCs using a viral vector, wherein the viral vector is a lentiviral, retroviral, or adenoviral vector. In some embodiments, the introduction step is performed ex vivo.

BRIEF DESCRIPTION OF THE FIGURES

FIG. 1A is a representative fluorescent image showing recruitment of BM-derived GFP$^+$ VE-cadherin$^+$ EPCs (arrows) at the periphery of early nonvascularized Lewis Lung Carcinoma (LLC) tumors (day 4-6, n=15). CD31+ mature vessels are observed in the host tissue but not in the tumors. The dotted line separates the host tissue from the tumor. Scale bar, 100 μm. FIG. 1B is high resolution image showing GFP$^+$ VE-cadherin$^+$ CD31$^{low}$ EPCs (arrows) at the periphery of LLC tumors (day 4). DAPI was used to stain the nucleus of all cells. Scale bar, 5 μm.

FIG. 2A is a representative fluorescent image showing CD31$^+$ mature vessels in LLC tumors (day 6-8, n=15). Arrows depict incorporated BM-derived endothelial cells in these vessels. Scale bar, 200 μm. The dotted line separates the host tissue from the tumor. FIG. 2B is a high resolution image of a representative blood vessel showing an incorporated mature BM-derived GFP$^+$ CD31$^+$ VE-cadherin$^+$ co-expressing cell (arrow). The lumen of the vessel (L) and VE-cadherin staining the adherens junctions between endothelial cells are shown. Scale bar, 20 μm. FIG. 2C shows optical sectioning (Z-stack resolution 0.275 μm) of the BM-derived endothelial cells showing that GFP and CD31 signals are localized within the same individual cell (X Z and Y Z axis are represented by top and side panels).

FIG. 3A is flow cytometry analysis of LLC tumors (day 4-14; n=5 per group), showing relative contribution of BM-derived EPCs (GFP$^+$ VE-cadherin$^+$ CD31$^{low}$, CD11b$^-$), and host-derived ECs (GFP$^-$ VE-cadherin$^+$ CD31$^+$, CD11b$^-$). Total number of cells analyzed was 2×10$^5$ per animal, except for Day 4, due to smaller tumor size. Each analysis was performed in duplicate. Error bars represent standard deviations. This experiment was repeated three times and identical trends were observed. FIG. 3B is a graph showing quantification of vessels in LLC tumors (day 4-28) with incorporated BM-derived ECs (GFP$^+$, CD31$^+$, VE-cadherin$^+$), a minimum of 400 vessels counted per time point from 6 non sequential sections and 20 images per tumor, Z-stacks evaluated for each section. Error bars represent standard deviations. FIG. 3C is a representative image showing a tumor vessel form an animal perfused with isolectin GS-IB4 and stained with CD31. Arrows indicate isolectin IB4 staining the luminal surface of the EC in the vessel. L denotes the lumen. Scale bar, 20 µm. FIG. 3D is flow cytometric analysis of LLC tumors (day 6-8) showing that fluorescent isolectin specifically stains a population of luminally-incorporated CD31$^+$ ECs. FIG. 3E is flow cytometric analysis showing that fluorescent isolectin stains a population of luminally-incorporated ECs (CD31$^+$ CD11b$^-$) derived from LLC tumors (Left). Of these 31±8.3% are BM-derived (GFP$^+$ CD31$^+$ Isolectin$^+$ CD11b$^-$) (Right). The averages and standard deviation were determined by analyzing 1×10$^5$ cells per animal (n=5). SSC-A denotes side scatter values.

FIG. 4A is a photograph showing primary adenoma lesions in mammary gland sections from a PyMT mouse at 8 weeks of age. Preexisting CD31$^+$ vessels are observed surrounding the adenomas. Scale bar, 100 µm. FIG. 4B shows recruitment of BM-derived GFP$^+$ VE-cadherin$^+$ EPCs (arrows) at the periphery of the avascular adenoma-carcinoma progression is shown. Scale bar, 100 µm. FIG. 4C is a photograph of an early carcinoma showing recruited CD31$^+$ mature vessels in the tumor mass (10 weeks of age). Arrow depicts incorporated BM-derived endothelial cells in a vessel. Scale bar, 100 µm. FIG. 4D is a high resolution image of a representative blood vessel (box in C) showing an incorporated mature BM-derived GFP$^+$ CD31$^+$ co-expressing cell (arrow). Scale bar, 20 µm. DAPI was used to stain the nucleus of all cells.

FIG. 5A is a scatter plot showing VE-cadherin expressing EPCs (red) in the BM-derived Lin$^-$ CD11b$^-$ fraction. FIG. 5B is a high resolution image of immunostaining of co-cultured BM-derived GFP$^+$ EPCs and mature ECs (non-GFP) in 3D matrigel at 12 hours. It shows an unincorporated, BM-derived GFP$^+$ VCAM-EPC (white arrow, lower panel). Scale 100 µm. FIG. 5C is a high resolution image of multiple BM-derived ECs (GFP$^+$ VCAM$^+$, yellow arrows) that have incorporated into vascular tubes 48 hours following co-culture. It shows an incorporated BM-derived GFP$^+$ EC (lower panel, yellow arrow). Scale, 100 µm. SSC-A denotes side scatter values.

FIG. 6A shows five color immunostaining of early LLC tumors (day 6) with VE-cadherin antibody E4G10 (white arrows), pan VE-cadherin antibody 11D4.1 (VE-cadh-$^{pan}$, red arrows) and CD31. E4G10 exclusively staining EPCs is shown (double red and white arrows). Scale bar, 20 µm. FIG. 6B shows immunostaining of early tumors (day 6) with CD31 and a pan VE-cadherin antibody. Low magnification image showing endothelial projections of the invading tumor vasculature. Yellow arrows depict VE-cadherin+ EPCs in the vicinity. Scale bar, 100 µm. GFP staining is not included for precise visualization. FIG. 6C shows higher magnification of the area denoted by a rectangle (in B) depicting that the endothelial projections are devoid of VE-cadherin (white arrows).

FIG. 7A shows LLC tumor volume at day 14 in animals administered with isotype control $^{225}$Act-IgG and unlabeled E4G10 or $^{225}$Act-E4G10 antibody (n=5, 10 respectively per group). FIG. 7B shows the number of BM-derived EPCs (GFP$^+$ VE-cadherin$^+$ CD31$^{low}$ CD11b$^-$) cells in early tumors (day 6) in animals administered with control or $^{225}$Act-E4G10 antibody at days 3 and 5 post-tumor innoculation (n=5, 10 respectively, 1×10$^5$ events counted per n). Bars denote averages. FIG. 7C shows BM-derived GFP$^+$ CD11b$^+$ cells in tumors from animals treated as in FIG. 7B (n=5, 10 respectively, 1×10$^5$ events counted per n). Bars denote averages. FIG. 7D shows the vessel density in tumors in animals treated with control and test antibody (day 14, n=5, 7 respectively per group). FIG. 7E shows CD31 immunostaining of tumor sections (day 14) isolated from E4G10 treated and control treated animals. Scale bar, 50 µm. Error bars represent standard deviations. "*" represents significant by t-test (*p<0.05).

FIG. 8A shows a tumor (day 6) with both a mature EC (M) and an EPC (IM). Quantitation shows greater than 10-fold lower CD31 signal intensity in an EPC relative to mature EC. Error bars represent the standard error of the mean. Scale bar, 50 µm.

FIG. 11A is a high resolution image showing a portion of a blood vessel with an incorporated BM-derived GFP$^+$ CD31$^+$ VE-cadherin$^+$ EC. The lumen of the vessel (L) and VE-cadherin staining the adherens junctions between ECs are shown (white arrows). Optical sectioning shows that VE-cadherin is localized at the junction of the incorporated cell (see white arrows in the YZ axis, middle panel). Scale bar, 20 µm. FIG. 11B is a high resolution image showing a GFP$^+$ perivascular cell closely associated with a CD31$^+$ vessel. Scale bar, 20 µm. FIG. 11C is a high resolution image showing a false positive GFP$^+$ endothelial cell that appears to be vessel-incorporated (XY plane). Scale bars, 20 µm.

FIG. 12A is a panel of representative fluorescent images showing that the vessel incorporated BM-derived GFP$^+$ EC (yellow arrow) does not express CD45. GFP+ CD45+ cells are shown (white arrows) in the vicinity. Scale bar, 20 μm. FIG. 12B shows a magnified portion of the boxed area in A showing a vessel incorporated GFP+ CD31+ cell (arrow). Scale bar, 10 μm. FIG. 12C is a scatter plot showing that neither the total ECs (Isolectin+ CD31+ CD11b−) (left) nor the BM-derived ECs (GFP+ Isolectin+ CD31+ CD11b−) (right) express CD45.

FIG. 13A is a representative fluorescent image showing recruitment of donor BM-derived GFP+ VE-cadherin+ EPCs at the periphery of early melanomas (day 4-6). Scale bar, 200 μm. FIG. 13B is a panel of high resolution images showing mature vessels in melanoma tumors (day 8). Arrow depicts incorporated BM-derived ECs (GFP+ CD31+ Isoectin+) in these vessels. Scale bar, 20 μm. FIG. 13C is flow cytometry showing percentage of luminally-incorporated BM−derived ECs (GFP+, CD31+, Isolectin+ CD11b−) in total ECs (CD31+ CD11b−) in melanoma (Mel).

FIG. 15A is a high resolution image showing that the incorporated GFP+ EC also expresses CD31. Scale bar, 10 μm.

FIG. 16A shows that E4G10 recognizes the monomeric VE-cadherin on the BM-derived GFP+ EPCs (white arrows), but not in the nascent vasculature (red arrows).

FIG. 17a is a schematic of a lung metastasis experiment. LLC tumor cells stably expressing RFP were inoculated into recipient animals that were previously reconstituted with GFP+ BM. The primary tumors are allowed to grow for two weeks and resected. Lung metastases are analyzed.

FIG. 18A is a panel of fluorescent stereomicroscope images of whole lungs isolated from mouse reconstituted with GFP+ BM after primary tumor resection. Tumor cells (RFP) and BM-derived cells (GFP) were detected in lung metastases post primary tumor innoculation (day 14, 21, 28). Representative data from n=6 animals per time point. Scale bar, 5 mm. FIG. 18B shows the quantitation of metastatic colonies in the lung post primary tumor inoculation (day 14, 21, 28). n=5-6 per group. FIG. 18C is a representative fluorescent image showing an avascular metastatic lesion (upper panel, day 14), and a vascularized macrometastases (lower panel, day 21). Blood vessels were detected by anti-CD31 antibody. Scale bar, 200 μM.

FIG. 19A is a panel of fluorescent stereomicroscopic images of whole lungs showing metastases progression (wk 12-16) in a MMTV-PyMT mouse reconstituted with GFP+ bone marrow. GFP+ BM cells in a 16 week old metastases are shown (right panel). Scale bar, 5 mm.

FIG. 20A is a representative fluorescent image showing recruitment of BM-derived EPCs (GFP+ VE-cadherin+, arrows) at the periphery of early avascular LLC metastases in the lung (day 14). Scale bar, 100 μM. DAPI was used to stain the nucleus of all cells. The dotted line separates the host tissue from the tumor. FIG. 20B is a flow cytometry analysis of single cell suspensions from lungs of animals (day 14; n=5 per group), showing the recruitment of BM-derived EPCs (GFP+ VE-cadherin+ CD31$^{low}$ CD11b) in lungs with micrometastases. The averages and standard deviation were determined by analyzing 1×10^5 cells per animal (n=5). FIG. 20C is a high resolution image of a representative blood vessel in macrometastases showing an incorporated mature BM-derived GFP+ CD31+ endothelial cell (arrow). Scale bar, 20 μM. FIG. 20D is an optical sectioning (Z-stack resolution of 0.275 μM, a total of 30 stacks analyzed) of a BM-derived ECs showing that GFP and CD31 signals are localized within the same individual cell (X Z and Y Z axis are represented by top and side panels). Scale bar, 10 μM. FIG. 20E is a flow cytometric analysis showing the contribution of vessel incorporated BM-derived ECs (GFP+ CD31+ Isolectin+ CD11b−). The averages and standard deviation were determined by analyzing 1×10^5 cells per animal (n=5).

FIG. 21A is a schematic of a lentiviral vector used for delivering miR30-based shRNAs in the BM-progenitors. TRE, tetracycline responsive element; cPPT, central polypurine tract; LTR, long terminal repeat; SIN, self-inactivating long terminal repeat. FIG. 21B shows the induction of GFP expression in the inducible lentiviral vector transduced cells. U2OS-rtTA cells were infected with lentivirus encoding inducible GFP-Id1shRNA. GFP expression was detected by microscopy 24 hours post induction with Dox (500 ng/ml). FIG. 21C shows U2OS-rtTA cells tranduced by a lentiviral vector encoding inducible Id1 shRNAs. Stable U2OS-rtTA cells were transfected with a construct expressing Id-CFP fusion protein. The expression of the fusion protein was detected by Western Blot analysis in the presence (+Dox) or absence (−Dox) of Doxycycline. FIG. 21D is a schematic showing a lentiviral-based transduction of BM-progenitors ex vivo. Lin− cells were enriched from freshly isolated BM cells from Rosa26-rtTA transgenic mice. These cells were transduced with lentiviral vector encoding inducible shRNA targeting Id1 or control shRNA. BM transplantation was performed with the injection of 5×10^5 transduced Lin− cells per animal in lethally irradiated animals, followed by tumor implantation, primary tumor resection and induction of shRNAs by doxycycline administration.

FIG. 22A is a representative stereomicroscope image of lung metastases formation (Day 28) in a non-specific shRNA bone marrow transplanted (BMT) mice (upper panel) and Id1-shRNA BMT mice (lower panel) in the absence of Dox (−Dox) and presence of Dox (+Dox). Scale bar, 20 μM. FIG. 22D shows the quantification of the number of metastases in the lungs of inducible Id1 shRNA BMT mice at day 28 in the absence of Dox (−Dox) and presence of Dox (+Dox). n=5 per group. FIG. 22C is a table showing the percentage of micrometastases and macrometastases in inducible Id1 shRNA BMT mice in the absence of Dox (−Dox) and presence of Dox (+Dox). FIG. 22D is a Q-PCR analysis showing fold suppression of Id1 (% of mRNA copies compared to control) in the BM harvested from Dox administered mice relative to control mice (n=5).

FIG. 23A shows VE-cadherin$^+$ EPCs expressing CXCR4 (arrows). Scale bar, 20 μM.

FIG. 24A shows that VE-cadherin$^+$ EPCs express integrin α4 (arrows). Scale bar, 20 μM. FIG. 24B shows that VE-cadherin$^+$ EPCs express integrin β1 (arrows). Scale bar, 20 μM. FIG. 24C shows that VE-cadherin$^+$ EPCs are observed in the proximity of VCAM expressing CD31$^+$ neovessels. Scale bar, 100 μM; L, Lumen. DAPI was used to stain all nuclei.

FIG. 25A is a multichannel fluorescent image showing that the BM-derived GFP$^+$ VE-cadherin$^+$ immature ECs (white arrow) at the tumor periphery express Id1. BM-derived GFP$^+$ VE-cadherin$^-$ cells do not express Id1 (yellow arrow). FIG. 25B: RT-PCR products showing reduction in Id1 mRNA levels by specific shRNAs as compared to a control non-specific (NS) shRNA. FIG. 25C: western blot showing reduction in Id1 protein levels by an Id1-specific shRNA.

FIGS. 26A and B show that Id1 is up-regulated in tumor challenged EPCs. FIG. 26A is a bar graph of Quantitative RT-PCR analysis showing that GATA2, CXCR4, VEGFR2, Id1 and VE-cadherin mRNA is up-regulated at least 2-fold in Lin$^-$ BM cells following LLC tumor challenge (day 6), compared to non-tumor challenged Lin$^-$ BM. Data represented as Mean % mRNA in tumor challenged BM compared with unchallenged Lin$^-$ BM control±S.E.M (n=5).

FIG. 27A is a schematic showing a lentiviral-based transduction of BM-progenitors ex vivo. Lineage negative (lin$^-$) bone marrow cells were enriched from freshly isolated total BM cells from wild type mice. These cells were transduced with lentiviral vector encoding GFP driven by Id1 promoter. BM transplantation was performed with 5×10$^5$ infected cells per animal in lethally irradiated animals, followed by tumor implantation. FIG. 27B is a representative fluorescent image showing recruitment of BM-derived GFP$^+$ cells at the periphery of early nonvascularized LLC tumors (day 4-6). The dotted line separates the host tissue from the tumor. Id1pr-GFP, Id1 promoter driving GFP. FIG. 27C is a high resolution image showing that the GFP$^+$ cells express VE-cadherin and flk1/VEGFR2 (for VEGFR2, see FIG. 34). DAPI was used to stain the nucleus of all cells. FIG. 27D is a representative fluorescent image showing CD31$^+$ mature vessels in LLC tumors (day 6-8). GFP$^+$ EPCs were observed in the vicinity of these CD31$^+$ vessels. FIG. 27E is a high resolution image of a representative blood vessel showing an incorporated mature BM-derived GFP$^+$ CD31$^+$ co-expressing cell (arrow).

FIG. 28A: Upper, Schematic representation of the Id1pr/p LV vector. Id1 proximal promoter (Id1pr/p) driving expression of GFP or RFP; cPPT, central polypurine tract; WPRE, woodchuck hepatitis virus post transcription regulatory element; LTR, long terminal repeat; SIN, self inactivating; Middle, Induction of GFP expression in mHEVCs is dependent on BMP-2 dosage. Lower, RFU—Relative fluorescence units. BMP-2-mediated dose-dependent induction of GFP expression in stable Id1pr/p-GFP mHEVCs and C2C12 cells (myoblasts), under low serum conditions (2.5% FBS), as determined by FACS. Data presented as Mean % of relative fluorescence of treated cells compared with untreated controls±SE (n=3 per treatment). FIG. 28B: Upper, Analysis of PB from LLC tumor challenged ACTb-EGFP$^+$ Id1pr/p-RFP mice showing that BM-derived ACTbEGFP$^+$ cells expressing Id1pr/p-RFP$^+$ is also VE-cadherin$^+$ (arrow). Scale bar=20 μm. Middle, A representative scatter plot showing FACS analysis of peripheral blood (PB) from WT and Id1pr/p-GFP tumor-challenged mice, showing that Id1pr/p-GFP marks 2.38±0.52% of the total mobilized circulating BM-derived cells following tumor challenge. Lower, FACS analysis of PB from Id1pr/p-GFP tumor challenged mice showing that Id1pr/p-GFP preferentially marks ~80% BM-derived circulating EPCs (c-Kit$^+$ VEGFR2$^+$ VE-cadherin+), as opposed to ~5% of CD45$^+$ hematopoietic cells, and ~8% of GR1$^+$ neutrophils. Data represented as mean number of GFP$^+$ cells as a percentage of total PBMCs±S.E.M (n=5). FIG. 28C: Upper, BM from BMT animals showing donor-derived (ACTb-EGFP$^+$) VE-cadherin$^+$ Id1pr/p-RFP$^+$ cells (arrow). Middle, Scatter plot representative of FACS analysis of mononuclear BM cells from WT and Id1pr/p-GFP tumor-challenged mice, showing that Id1pr/p-GFP$^+$ marks 1.23±0.08% of BM cells, following tumor challenge. Lower, FACS analysis of the BM from Id1pr/p-GFP mice showing that Id1pr/p-GFP$^+$ marks ~60% of the BM VE-cadherin+ cells, and ~0.1% of the CD11b$^+$ cells. Data represented as mean number of GFP$^+$ cells as a percentage of total BM cells±S.E.M (n=5). FIG. 28D: Immunofluroescent microscopy showing recruitment of Id1pr/p-GFP$^+$ cells to the periphery of early nonvascularized LLC tumors (day 8) from Id1pr/p-GFP mice. Scale bar=100 μm. The dotted line separates the tumor from the host tissue. Lower, higher magnification of the area denoted by a rectangle and depicting Id1pr/p-GFP$^+$ VE-Cadherin$^+$ cells (arrow). FIG. 28E: Immunofluorescent microscopy showing recruitment of ACTb-EGFP$^+$ Id1pr/p-RFP$^+$ VE-cadherin+ cells to the periphery of LLC tumors in ACTb-EGFP$^+$ Id1pr/p-RFP mice. Scale bar=100 μm. Lower, higher magnification of the area denoted by a rectangle depicting a ACTb-EGFP$^+$ Id1pr/p-RFP$^+$ VE-cadherin$^+$ cell (arrows). FIG. 28F: Representative image of a blood vessel showing an incorporated BM-derived Id1pr/p-GFP+ CD31+ cell (arrow) identified in day 14 LLC tumor. Scale bar=20 μm. DAPI was used to stain the nucleus of all cells.

FIG. 29A: HSV-tk is expressed in stable Id1pr/p-GFPITK 293T cells (arrow) (10% FCS). Scale bar=20 μm. FIG. 29B: Treatment with GCV showing dose-dependent killing of Id1pr/p-GFPITK cells as determined by microscopy (Upper, Scale bar=100 μm), and FACS analysis following PI-staining (Lower). Data represented as mean number of PI+Id1pr/p-GFP+ cells as a percentage of total±S.E.M. (n=3 per treatment). FIG. 29C: HSV-tk protein is detected in VE-cadherin+ Id1pr/p-GFP+ BM cells (arrow), from Id1pr/p-GFPITK BMT mice. Scale bars=20 μm. FIG. 29D: Upper, Unincorporated Id1pr/p-GFP+ CD31+ EPCs identified in control Id1pr/p-GFPITK (−GCV) tumors. Scale bars=100 μm. Lower, Vessel incorporated Id1pr/p-GFP+ EPCs in the tumors of control Id1pr/p-GFPITK (−GCV) mice.

FIG. 30A: Upper, Schematic representation of the Id1pr/p LV vector, with Id1pr/p driving expression of GFP and HSV-tk. Lower, LLC tumor growth (mean±S.E.M) and morphology in Id1pr/p-GFPITK BMT mice (n=10) and Id1pr/p-GFP BMT mice (n=5), either treated with GCV (+GCV) or untreated (−GCV). The experiment was repeated and similar trends were observed. FIG. 30B: FACS analysis of the PB from tumor challenged Id1pr/p-GFPITK (+GCV), Id1pr/p-GFPITK (−GCV) and Id1pr/p-GFP (+GCV) BMT mice, showing the number of mobilized CEPs (c-Kit+ VEGFR2+), hematopoietic cells (CD45+) and hematopoietic progenitors (CD45+ c-Kit+). A total of 1×10$^6$ cells were analyzed per animal. Data is represented as Mean number of cells per 1×10$^5$ PBMCs±S.E.M (n=5 per group). FIG. 30C: Analysis of BM VE-cadherin+ GFP+ mononuclear cells following GCV treatment in Id1pr/p-GFPITK animals using microscopy (upper) and FACS analysis (lower). Scale bar=100 μm. Data showing significant difference between GCV treated Id1pr/p-GFPITK and untreated animals (P=0.040, by Students t-Test). Numbers provided are normalized per 1×10$^6$ BM mononuclear cells. FIG. 30D: Vessel density in LLC tumors (P<0.05, Students t-Test, n=15). Data presented as average number of vessels per field±S.E.M. Scale bar=100 μm.

FIG. 31A: Upper Left, Schematic representation of pWPTU6 LV vector showing a pol III U6 promoter driving expression of shRNA (Ω) and EF-short promoter driving expression of GFP. Lower Left, LLC tumor growth in pWPTU6-NSΩ and pWPTU6-Id1Ω BMT mice. Data is represented as mean volume±S.E.M (P<0.001 by Student's t-Test, n=5 per group). Upper right, Tumor morphology and CD31 immunostaining of tumors from pWPTU6-NSΩ or pWPTU6-Id1Ω BMT mice. Scale bar=100 μm. Lower right, Q-PCR analysis of Id1 and CD45 mRNA levels in the BM of pWPTU6-Id1Ω mice. Data represented as mean level of mRNA as a % of mRNA in pWPTU6-NSΩ control BM±S.E.M. (n=5 per group). FIG. 31B: Upper right, Schematic representation of the Id1pr/p-GHPΩ LV vector showing the pol II Id1 promoter driving expression of GFP and miR30-based Ω. Lower, LLC tumor growth and morphology in Id1pr/p-GFPId1Ω, Id1pr/p-GFPVEGFR2Ω and Id1pr/p-GFPNSΩ BMT mice. Data represented as mean volume±S.E.M (P=0.0117 by Student's t-Test, n=5 per group). FIG. 31C: FACS analysis of PB showing the number of CEPs (c-Kit+ VEGFR2+ VE-cadherin+), neutrophils (GR1+) and hematopoietic (CD45+) cells in tumor challenged Id1pr/p-GFPΩ BMT mice. Data is represented as mean number of cells per 1×10$^5$±S.E.M. (n=5 per group; P values determined by Student's t-Test). The experiment was repeated and similar trends were observed. FIG. 31D: Vessel density in tumors from Id1pr/p-GFPΩ BMT mice (with the expression of shRNA against VEGFR2 or Id1, or non-specific shRNA). Scale bar=100 μm. Data presented as mean number of vessels per field±S.E.M (n=15 fields per group). FIG. 31E: Q-PCR analysis of Id1, VEGFR2, and CD45 mRNA levels in BM from Id1pr/p-GFPΩ mice. Data presented as mean level of mRNA copies as a % of mRNA from Id1pr/p-GFPNSΩ BM controls (n=4, repeats per sample).

FIG. 33A: A rabbit monoclonal Id1 antibody stains Id1pr/p-RFP+ cells (arrow) derived from the blood (Upper) and BM (Lower) of ACTb-EGFP+ Id1pr/p-RFP+ BMT mice. Scale bars=20 μm. FIG. 33B: Id1 antibody staining of Id1pr/p-GFP+ VE-cadherin+ cells in early LLC tumors growing in Id1pr/p-GFP+ mice. Scale bar=100 μm. Lower, higher magnification of the area denoted by a rectangle depicting Id1pr/p-GFP+Id1+ VE-cadherin+ cells (arrows). FIG. 33C: A representative image showing Id1 antibody staining of an Id1pr/p-GFP+ CD31+ vessel-incorporated EPC. Scale bar=100 μm. Lower, higher magnification of the area denoted by a rectangle depicting Id1pr/p-GFP+ Id1+ CD31+ cell (arrow). FIG. 33D: GFP antibody staining of Id1pr/p-GFP+ VE-cadherin+ cells (arrow) in the BM (Upper, Scale bar=20 μm) and in early tumors (Lower, Scale bar=100 μm) from Id1pr/p-GFP+ mice. DAPI was used to stain the nuclei of all cells.

FIG. 34A: Id1pr/p-GFP+ VE-Cadherin+ BM cells express VEGFR2 (arrow) Scale bar=20 μm. FIG. 34B: VCAM-1 but not CD11b. Scale bar=100 μm. Lower, higher magnification of the area denoted by a rectangle and depicting Id1pr/p-GFP+VCAM-1+ CD11b− cells (arrow). FIG. 34C: BM mononuclear cells harvested from ACTb-EGFP+ Id1pr/p-RFP+ BMT mice showing that Id1pr/p-RFP+ cells express Prominin 1 (arrow). Scale bar=20 μm. DAPI was used to stain the nuclei of all cells.

DETAILED DESCRIPTION OF THE INVENTION

Figure 1:
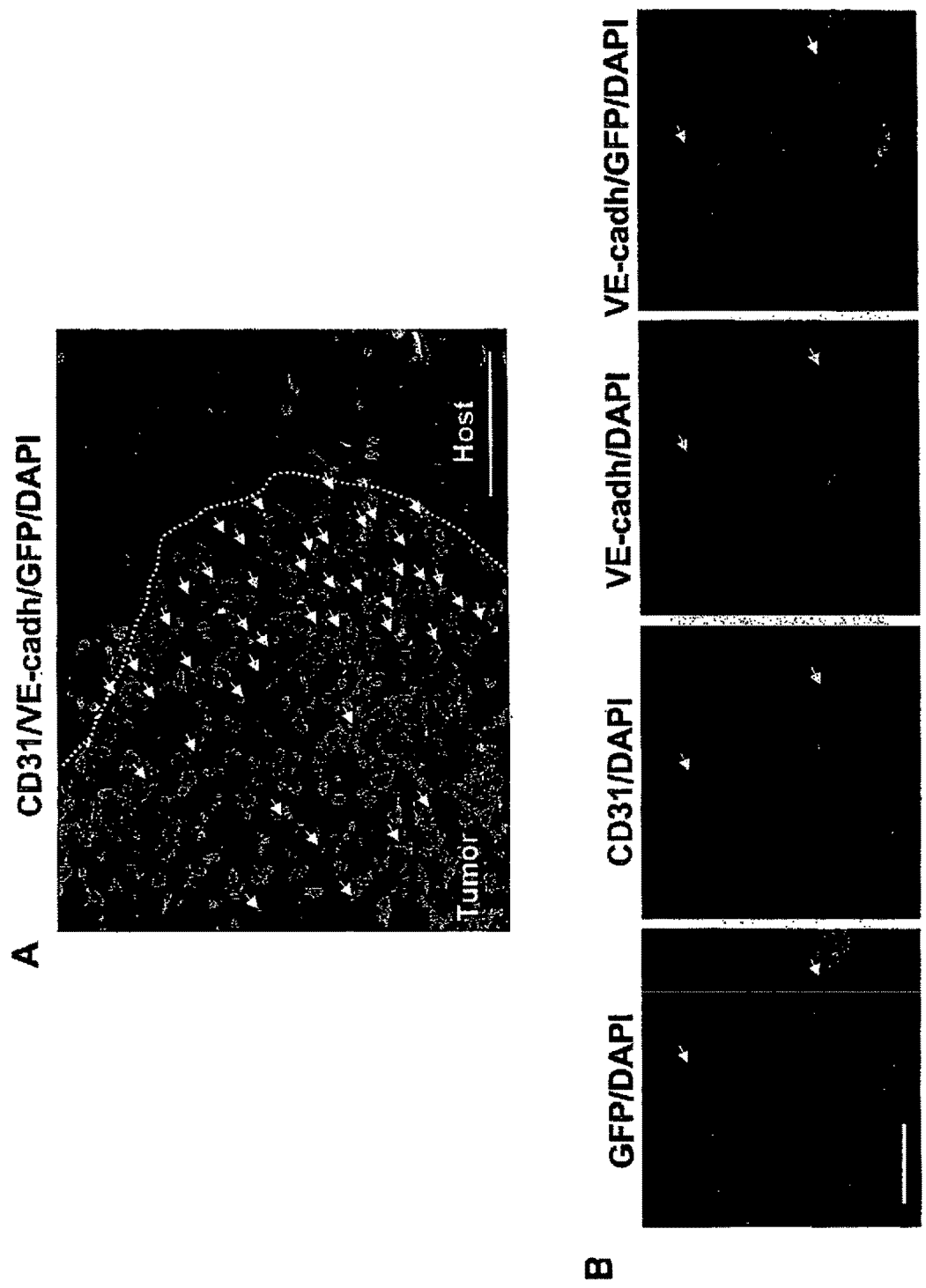
FIGS. 1A and 1B show BM-derived EPCs are recruited at the periphery of early tumors.

Tumors build vessels by co-opting pre-existing vasculature and de novo recruitment of BM-derived EPCs. However, the physiological contribution and the functional role of EPCs in tumor angiogenesis are controversial. By using genetically marked BM progenitor cells, we have discovered the precise spatial and temporal contribution of EPCs to the neovascularization of growing transplanted and spontaneous tumors in vivo using high resolution microscopy and flow cytometry. We have discovered that early tumors recruit BM-derived EPCs that differentiate into mature BM-derived endothelial cells and luminally incorporate into a subset of sprouting tumor neovessels. Notably, in later tumors, these BM-derived vessels are diluted with non-BM-derived vessels from the periphery, which accounts for purported differences in previously published reports. Furthermore, we have discovered that specific ablation of BM-derived EPCs with a cytotoxic agent such as alpha-particle-emitting anti-VE-cadherin antibodies, or with a suicide gene or a small interfering RNA molecule introduced into the EPCs, markedly impairs tumor growth that is associated with reduced vascularization. Our work shows that BM-derived EPCs involved in angiogenesis can be distinguished from other BM progenitor cell populations by a unique panel of markers. Specifically, these EPCs are VE-cadherin+VEGFR2+CD31$^{low}$Endoglin+Prominin I/AC133+CXCR4+VLA4+c-kit+. For example, we have demonstrated that the cell surface expression of endothelial cell marker CD31 is 10-30 fold lower in EPCs than mature endothelial cells Moreover, on EPCs, CD31 is uniformly distributed on the cell surface, whereas on mature endothelial cells, CD31 is distributed mostly at the adherent junctions. In sum, our work demonstrates that BM-derived EPCs are critical components of the earliest phases of tumor angiogenesis, including the progression of micrometastases to macrometastases in cancer. In addition, the determination of EPCs as VE-cadherin+ VEGFR2+ CD31$^{low}$ Endoglin+ Prominin I/AC133+ CXCR4+ VLA4+ c=kit+, all cell-surface proteins, makes it possible to isolate a substantially purified population of EPCs using cell sorting methods known in the art, for example, flow-cytometry-based cell sorting, fluorescence activated cell sorting (FACS), magnetic cell sorting, and antibody panning.

The development of macrometastases from dormant micrometastases is the major cause of mortality in cancer patients. However, despite the clinical importance of metastasis, the cellular and molecular mechanisms that govern macrometastases formation remain poorly understood. Our work demonstrates that the progression of micrometastaes to macrometastases is mediated by an angiogenic switch, associated with the de novo contribution of BM-derived EPCs. We have discovered that EPCs are recruited to sites of active neovascularization via the stromal derived factor 1 (SDF1)—Chemokine receptor 4 (CXCR4) and VLA (integrin α4β1)—VCAM interactions. Generation of a loss-of-function EPCs with inducible RNA interference (RNAi)-mediated suppression of an EPC-specific gene (e.g., Id1 transcription factor) does not affect initial colonization but markedly impairs both the size of metastatic colonies and neovascularization of the colonies. Thus, our work shows that EPC-mediated neovascularization is critical for metastasis progression, and that EPC targeting offers a valid approach for cancer therapy.

The existence of a BM reservoir of EPCs and their selective involvement in tumor neovascularization has considerable clinical significance because these cells represent a novel target for therapeutic intervention. The EPCs can be directly targeted for ablation or targeted to induce expression of transgenes or RNAi-mediated gene knockdown, or their selective homing to the tumor vessels may be exploited to deliver therapeutic cargos to the tumor microenvironment. For example, effective therapeutics in the form of stable inhibitory short hairpin (sh) RNAs targeting pro-angiogenic genes can be delivered by systemic administration of ex vivo expanded and engineered EPCs.

Given that BM transplantation is routinely performed in cancer patients, ex vivo expansion and manipulation of BM-progenitors will be particularly useful in cancer therapy. For example, Lentivirus-based approaches in clinical trials of human gene therapy, recently re-approved by the FDA, may be utilized. This approach may be used to deliver inhibitory shRNAs, toxic genes, and anti-angiogenic genes via autograft or allograft BM transplantations, followed by their stable engraftment in a patient's BM compartment.

This invention provides methods of inhibiting angiogenesis in a tumor, inhibiting tumor growth or formation, and inhibiting tumor metastasis (e.g. the transition from micrometastases to macrometastases) in a subject (e.g., a rodent such as a mouse, a hamster, or a rat, or a primate such as a human), wherein the BM-derived EPCs are inhibited. This method can be employed in conjunction with standard methods of cancer treatment (e.g., chemotherapy, radiation therapy, and surgical removal of tumors).

One approach to achieve EPC inhibition (e.g., inhibition of EPC growth, differentiation, or homing to a tumor site) is to administer to a subject an antibody against an EPC-specific cell surface molecule, wherein the antibody is optionally conjugated to a cytotoxin, e.g., conventional chemotherapy agents, and radioactive moieties (e.g., alpha-emitting radioactive isotope such as actinium-225). Monomeric VE-cadherin is one example of EPC-specific marker.

Another approach to inhibit EPCs is to introduce to the bone marrow-derived EPCs a suicide or anti-angiogenic gene under the transcriptional control of an EPC-specific gene promoter. Examples of suicide genes abound. Products of these genes genes (e.g., caspases and Cytochrome C) can cause apoptosis in combination with an inducer. For example, the suicide gene may be HSV-thymidine kinase (inducer: ganciclovir), cytosine deaminase (inducer: 5-FC), carboxypeptidase G2 (inducer: 4-[(2-chloroethyl)(2-mesyloxyethyl)amino]benzoyl-L-glutamic acid (CMDA)), purine nucleoside phosphorylase (PNP) (inducer: 6-methylpurine deoxyriboside (MEP) or Fludarabine), nitroreductase (NR) (inducer: dinitroaziridinylbenzamide CB 1954), deoxycytidine kinase (dCK), or cytochrome P450 (inducer: Cyclophosphamide (CPA), Ifosfamide or 4-Ipomeanol). See, e.g., Denny, *Journal of Biomedicine and Biotechnology* 2003:1, 48-70 (2003). Examples of anti-angiogenic genes are genes coding for thrombospondin 1 (TSP1), angiostatin, homeobox (HEX), and Endostatin.

In another approach, the inhibition of EPCs is achieved by introducing to the bone marrow-derived EPCs a small interfering RNA molecule against an EPC-specific gene whose expression is required for EPC-mediated tumor angiogenesis (e.g., a pro-angiogenic gene), or is upregulated by tumor challenge (e.g., Id1, VEGFR2/flk1, GATA-2, CXCR4, and VE-cadherin) and wherein the small interfering RNA molecule is under the transcriptional control of an EPC-specific promoter in an optionally inducible manner.

In some embodiments, the EPC-specific gene promoter is an Id1 gene promoter (see Working Examples below), a VEGFR2 gene promoter, or a VE-cadherin gene promoter. In further embodiments, the expression of the suicide gene or anti-angiogenic gene is inducible in the EPCs. Tissue-specific inducible expression of an exogenous gene can be achieved by well known methods. See, e.g., Working Examples below, and U.S. Pat. No. 6,639,121. Furthermore, the suicide gene, anti-angiogenic gene, or shRNA can be introduced to EPCs through the use of a viral vector, such as a lentiviral, retroviral, or adenoviral vector. In all of the above approaches, the EPCs can be manipulated ex vivo (e.g. expansion and viral transduction) and then implanted to the patient. For example transducing isolated lin⁻ BM cells with a viral vector encoding a gene-of-interest or shRNA driven by an EPC-specific promoter (e.g., Id1, VEGFR2, or VE-cadherin promoter), results in the gene-of-interest or shRNA being specifically expressed in EPCs, defined as VE-cadherin$^+$ VEGFR2$^+$ CD31$^{low}$ Endoglin$^+$ Prominin I/AC133$^+$ CXCR4$^+$ VLA4$^+$ c-kit$^+$ cells.

In some embodiments, the homing property of EPCs to tumor sites can be utilized in cancer treatment. For example, EPCs can be isolated from a patient (e.g., bone marrow, peripheral blood, or cord blood), conjugated to a therapeutic cargo, and then implanted back to the patient. Since EPCs preferentially home to tumor sites, the therapeutic cargo can thus be specifically delivered to those sites for more effective treatment.

This invention also features substantially purified population of bone marrow-derived EPCs, wherein the EPCs are purified from a subject, e.g., a human patient, by, e.g., flow cytometry-based cell sorting, fluorescence activated cell sorting, magnetic cell sorting, or antibody panning, based on their phenotype of being VE-cadherin$^+$VEGFR2$^+$CD31$^{low}$Endoglin$^+$Prominin I/AC133$^+$CXCR4$^+$VLA4$^+$c-kit$^+$.

Because of their preferential homing to tumor sites, tracking of EPCs in a patient can also indicate sites of tumor growth. For example, one can isolate bone marrow-derived EPCs from the patient, label with the isolated EPCs with a magnetically detectable moiety, and scan the subject by magnetic resonance imaging or positron emission tomography, where a higher-than-normal magnetic signal at a site of the patient indicates tumor growth at the site.

This invention also features methods of treating patients with a condition characterized by abnormally high rates of angiogenesis, comprising the step of inhibiting bone marrow-derived endothelial progenitor cells (EPCs) in the patient. Such conditions include, without limitation, age-related macular degeneration, rheumatoid arthritis, psoriasis, and diabetic blindness. For example, lin⁻ BM cells are transduced with viral vector encoding a suicidal gene, an anti-angiogenic gene, or an shRNA against an EPC-specific gene (e.g., Id1, VEGFR2, or VE-cadherin), driven by an EPC-specific promoter (e.g., Id1 promoter, VEGFR2 promoter, or VE-cadherin promoter). Neoangiogenesis is reduced, and the condition are alleviated. Alternatively, antibody against monomeric VE-cadherin (e.g., E4G10 antibody) optionally conjugated to a cytotoxin (e.g. alpha-emitting radioactive isotope, for example actinium-225) is injected into the subject. EPCs are selectively ablated, resulting in reduced neoangiogenesis and alleviation of the condition.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art. Throughout this specification and embodiments, the word "comprise," or variations such as "comprises," or "comprising" will be understood to imply the inclusion of a stated integer or group of integers but not the exclusion of any other integer or group of integers. The materials, methods, and examples are illustrative only and not intended to be limiting.

The following examples are meant to illustrate the methods and materials of the present invention. Suitable modifications and adaptations of the described conditions and parameters normally encountered in the art which are obvious to those skilled in the art are within the spirit and scope of the present invention.

EXAMPLE 1

Tumors build vessels by cooption of preexisting vasculature and de novo recruitment of bone marrow (BM)-derived endothelial progenitor cells (EPCs). However, the physiological contribution and the functional role of EPCs in tumor neoangiogenesis are controversial. By using genetically marked BM progenitor cells, we demonstrated the precise spatial and temporal contribution of EPCs to the neovascularization of growing transplanted and spontaneous tumors in vivo. We showed that early tumors recruited BM-derived EPCs that differentiated into mature BM-derived endothelial cells and luminally incorporated into a subset of sprouting tumor neovessels. Notably, in later tumors, these BM-derived vessels were diluted with non-BM-derived vessels from the periphery, which accounted for purported differences in previously published reports. Furthermore, ablation of BM-derived EPCs with alpha-emitting radioimmunoconjugates markedly impaired tumor growth associated with reduced vascularization. Our results demonstrate that BM-derived EPCs are critical components of the earliest phases of tumor neoangiogenesis.

A. Spatial and Temporal Contribution of BM-Derived EPCs in the Neovascularization of Growing Tumors.

In order to determine the contribution of the BM-derived EPCs to the formation of tumor neovasculature, we performed a bone marrow transplantation (BMT) experiment. To track BM-derived cells in vivo, GFP$^+$ BM cells were isolated from C57BL/6-Tg (ACTbEGFP) mice and transplanted into lethally irradiated age matched, syngeneic, non-GFP recipients. Analysis of bone marrow and peripheral blood (4-weeks post transplantation), showed greater than 95% reconstitution of recipient hematopoiesis by the donor BM-derived GFP$^+$ transplanted progenitor cells (data not shown), indicating stable replacement of original host stem-cell population by the donor cells. Next, the reconstituted mice were challenged with intradermal tumors such as, Lewis lung carcinoma (LLC), B6RV2 lymphoma, or orthotopic implanted melanoma (Aozuka et al., *Cancer Lett* 216, 35 (2004)). In addition to being syngeneic to the host, tumor implantations allow precise staging during tumor growth.

Figure 8:
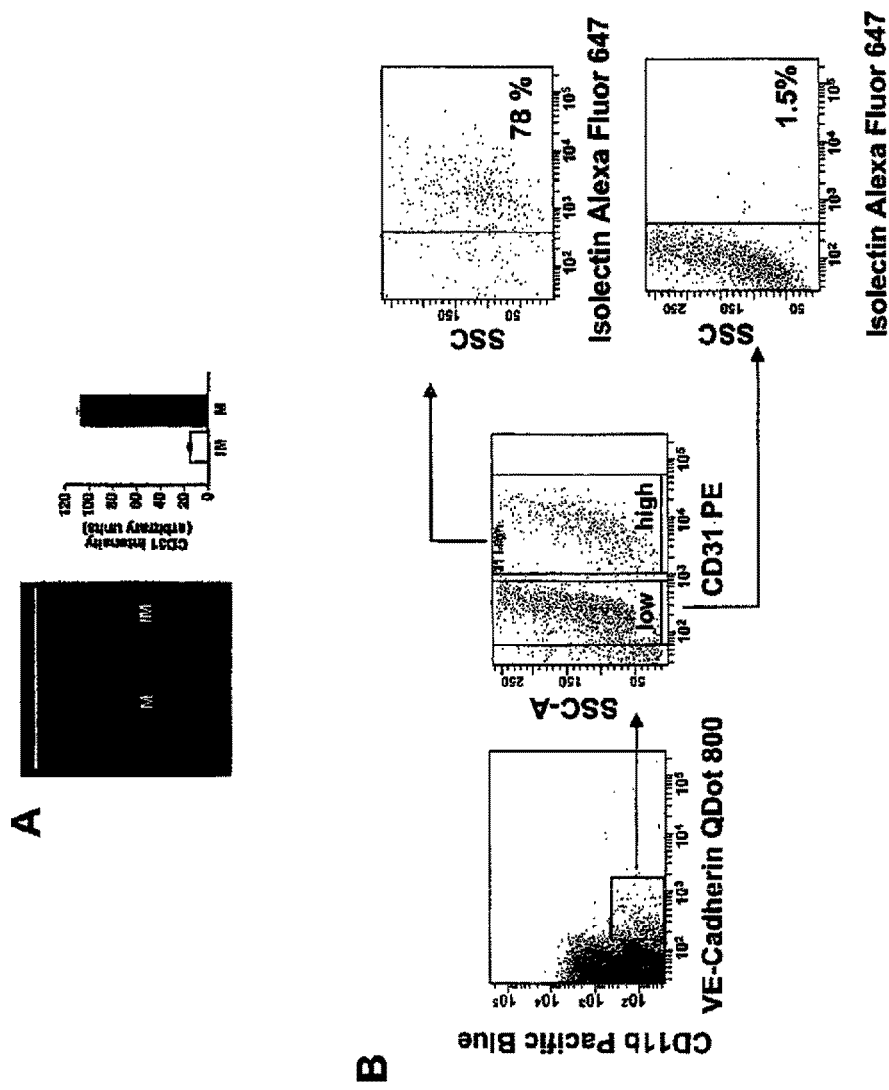
FIGS. 8A and B show the levels of CD31 expression on EPCs and endothelial cells.
FIG. 8B is flow cytometry analysis showing that the VE-cadherin$^+$ CD11b$^-$ cells in the tumors (day 6) are either CD31 low or CD31 high. Of these, the high CD31 expressing cells are in the functional vasculature (Isolectin$^+$) and the low CD31 expressing cells are EPCs (Isolectin−). Total cells examined were 1×10$^6$.
Figure 9:
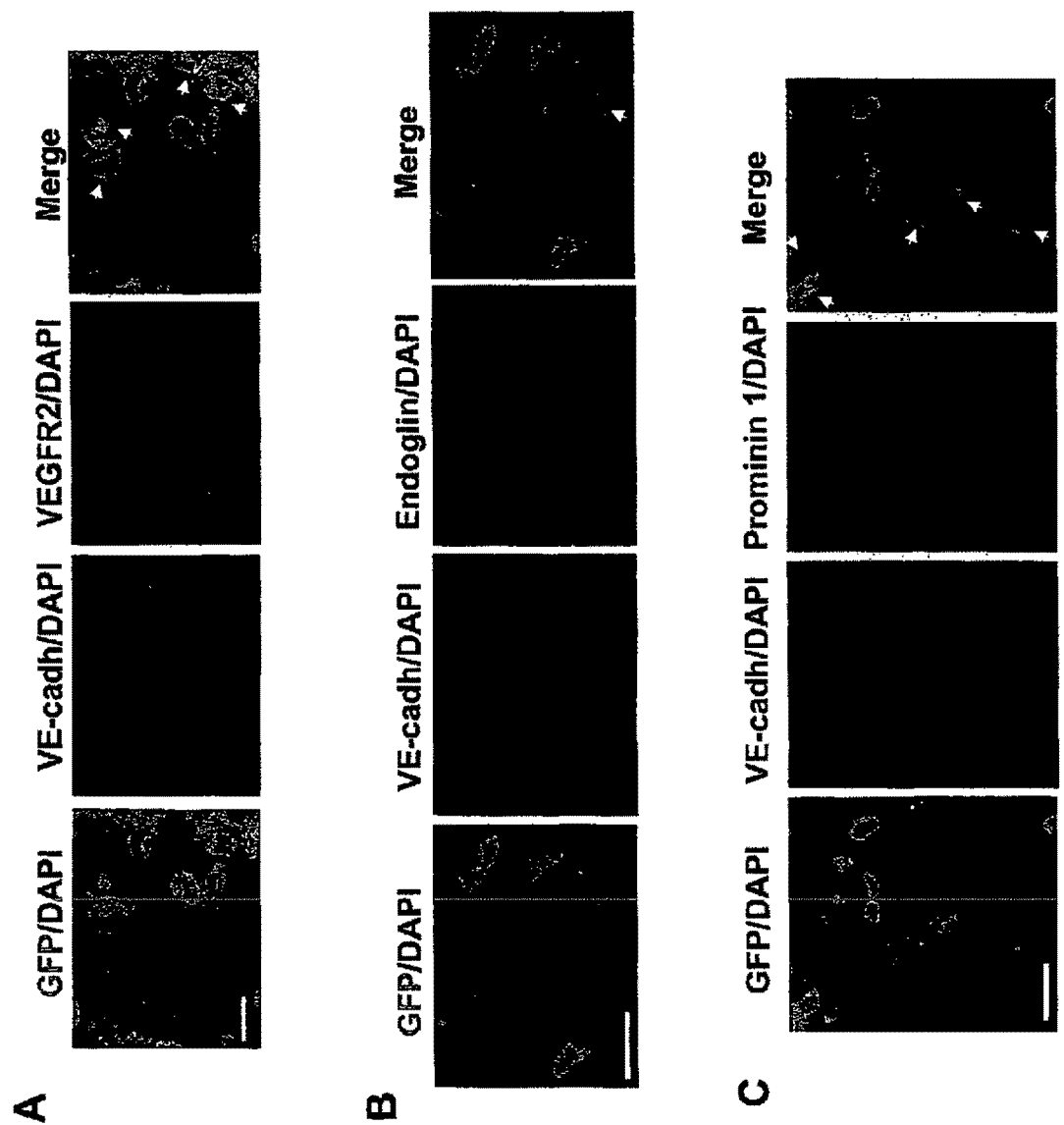
FIGS. 9A-C are multichannel fluorescent images showing: (A) GFP$^+$ VE-cadherin$^+$ VEGFR2$^+$ EPCs (arrows), scale bar, 10 µm; (B) GFP$^+$ VE-cadherin$^+$ Endoglin$^+$ EPC (arrows) at the periphery of LLC tumors (day 4), fluorescent signals shown individually or after merging (scale bar, 200 µm); and (C) a multichannel fluorescent image showing that BM-derived GFP$^+$ VE$^-$cadherin$^+$ EPCs (white arrows) in the early tumors (day 4) expressing stem cell marker Prominin I (AC133) (scale bar, 100 µm).
Figure 10:
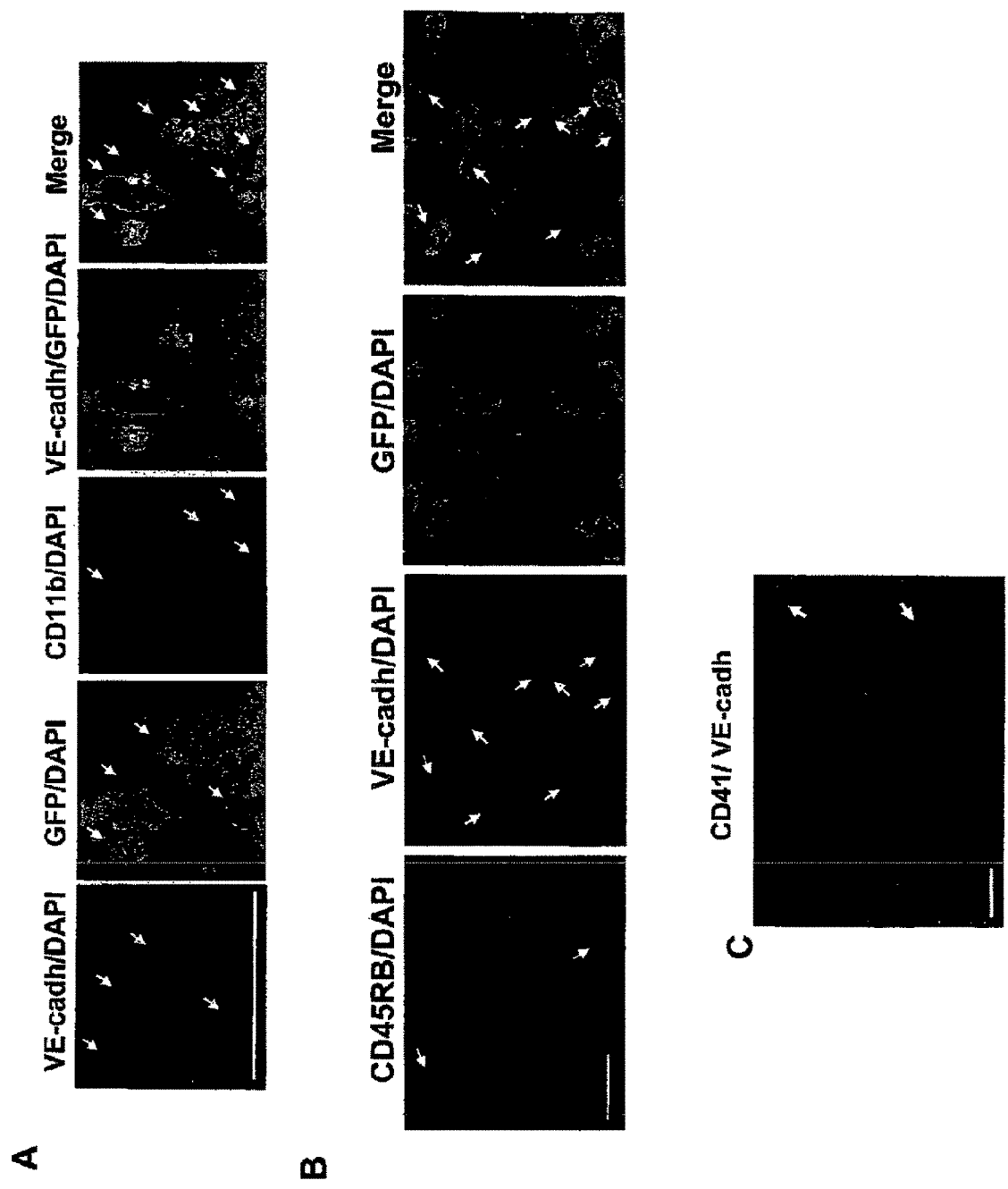
FIGS. 10A-C are high resolution images showing that the BM-derived GFP$^+$ VE-cadherin$^+$ EPCs lack hematopoietic markers: (A) CD11b (scale bar, 50 µm); (B) CD45RB (scale bar, 50 µm); and (C) CD41 (cytospun Lin$^-$ BM cells) (scale bar, 20 µm). White arrows denote BM-derived EPCs and yellow arrows denote CD11b$^+$ and CD45$^+$ cells.

We first determined the contribution of BM-derived endothelial progenitors to early stages of LLC tumor growth. Tumors were isolated, cryosectioned, and immunostained for endothelial cell (EC) markers (CD31/PECAM, VE-cadherin, VEGFR2/flk1, endoglin, and VCAM), progenitor markers (Prominin I/AC133), and various hematopoietic lineage markers. As expected, many BM-derived GFP+ cells were observed infiltrating the tumor bed. Interestingly, at early stages of tumor growth (day 4-6), we observed a marked recruitment of BM-derived GFP+ cells expressing the endothelial marker VE-cadherin at the periphery (FIG. 1A, arrows). Noticeably, these GFP+ VE-cadherin+ cells were recruited to early tumors prior to vessel invasion from the neighboring host tissue (FIG. 1A). Although these cells expressed VE-cadherin, we determined that they were not mature endothelial cells because they lacked typical mature EC morphology, expressed uniform cell surface VE-cadherin (compared to VE-cadherin localized at the adherens junctions between two adjacent mature endothelial cells in a vessel), and expressed low CD31 (greater then 10-fold reduction relative to endothelial cells in vessels) (FIG. 1B, arrows and FIG. 8A). Low CD31 expression on these cells was further confirmed by flow cytometric analysis of early tumors (FIG. 8B). These cells also expressed the endothelial specific marker VEGF receptor 2 (VEGFR2) and endoglin, and progenitor cell marker Prominin I/AC133 (FIGS. 9A-C), representing EPCs. The EPCs lacked expression of all hematopoietic lineage markers tested, including CD11b (monocytes, subsets of lymphocytes, Dendritic cells and NK cells), CD45RB (monocytes, granulocytes, subsets of T and B cells), and CD41 (megakaryocytes) (FIGS. 10A-C). Dim CD45 expression was observed in EPCs in the BM-compartment, but not in the tumors. In summary, these results demonstrate that BM-derived EPCs are recruited to early tumors prior to vessel formation, and that the EPCs are distinct from the hematopoietic lineages.

Figure 2:
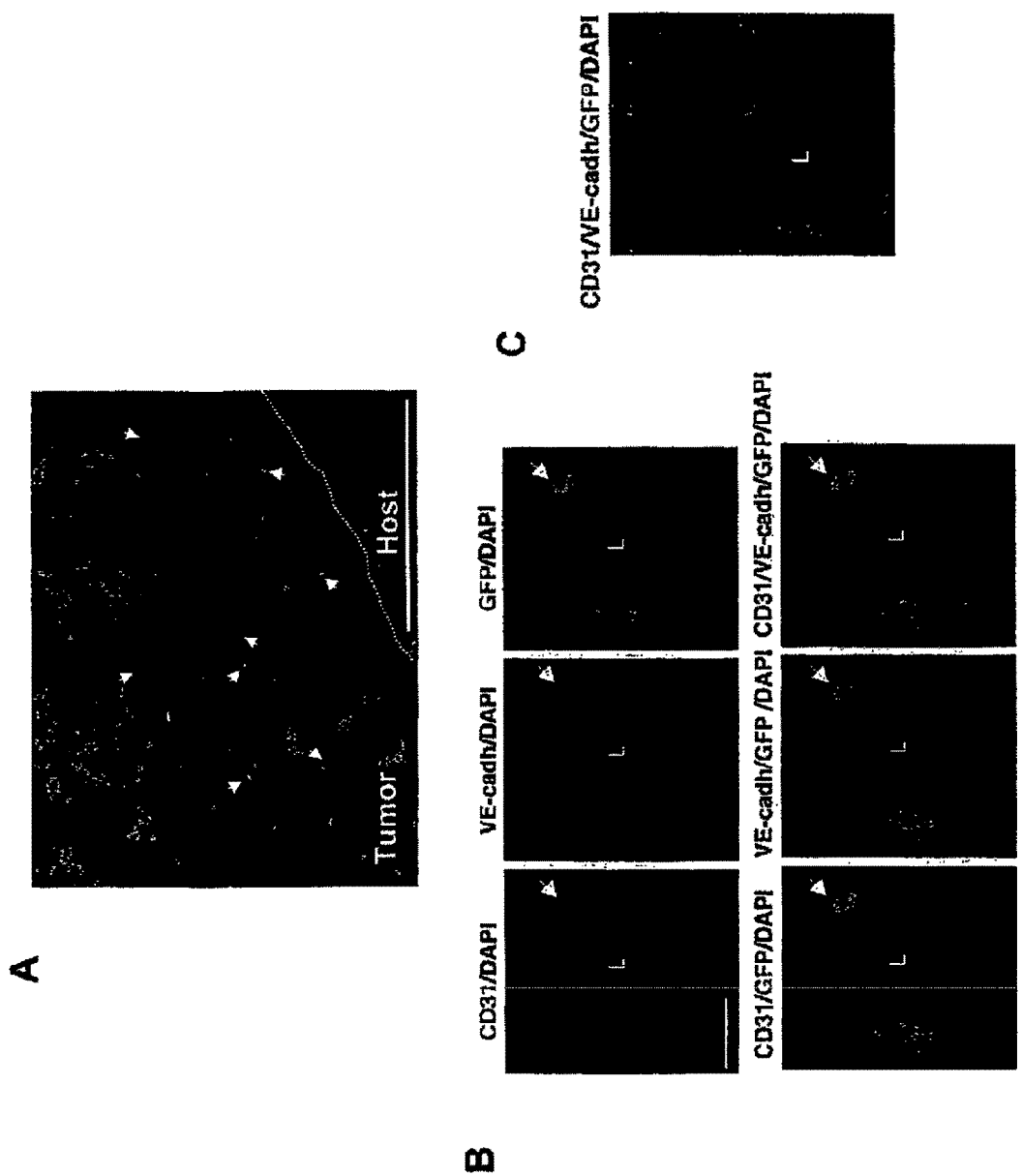
FIGS. 2A-C show that BM-derived endothelial cells are luminally incorporated in tumor neovasculature.
Figure 11:
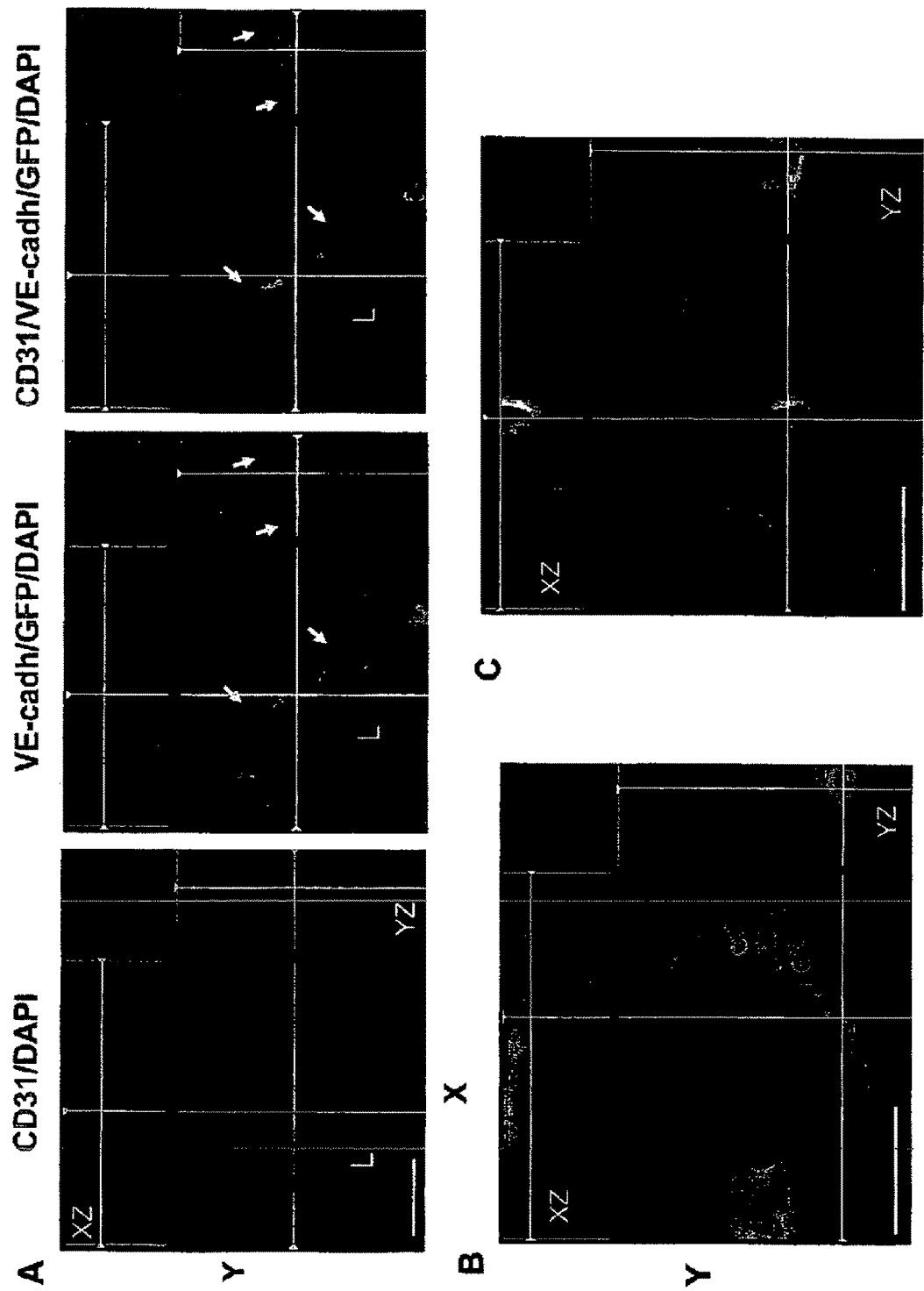
FIGS. 11A-C show that high resolution microscopy discerns vessel incorporated BM-derived ECs from perivascular cells.
Figure 12:
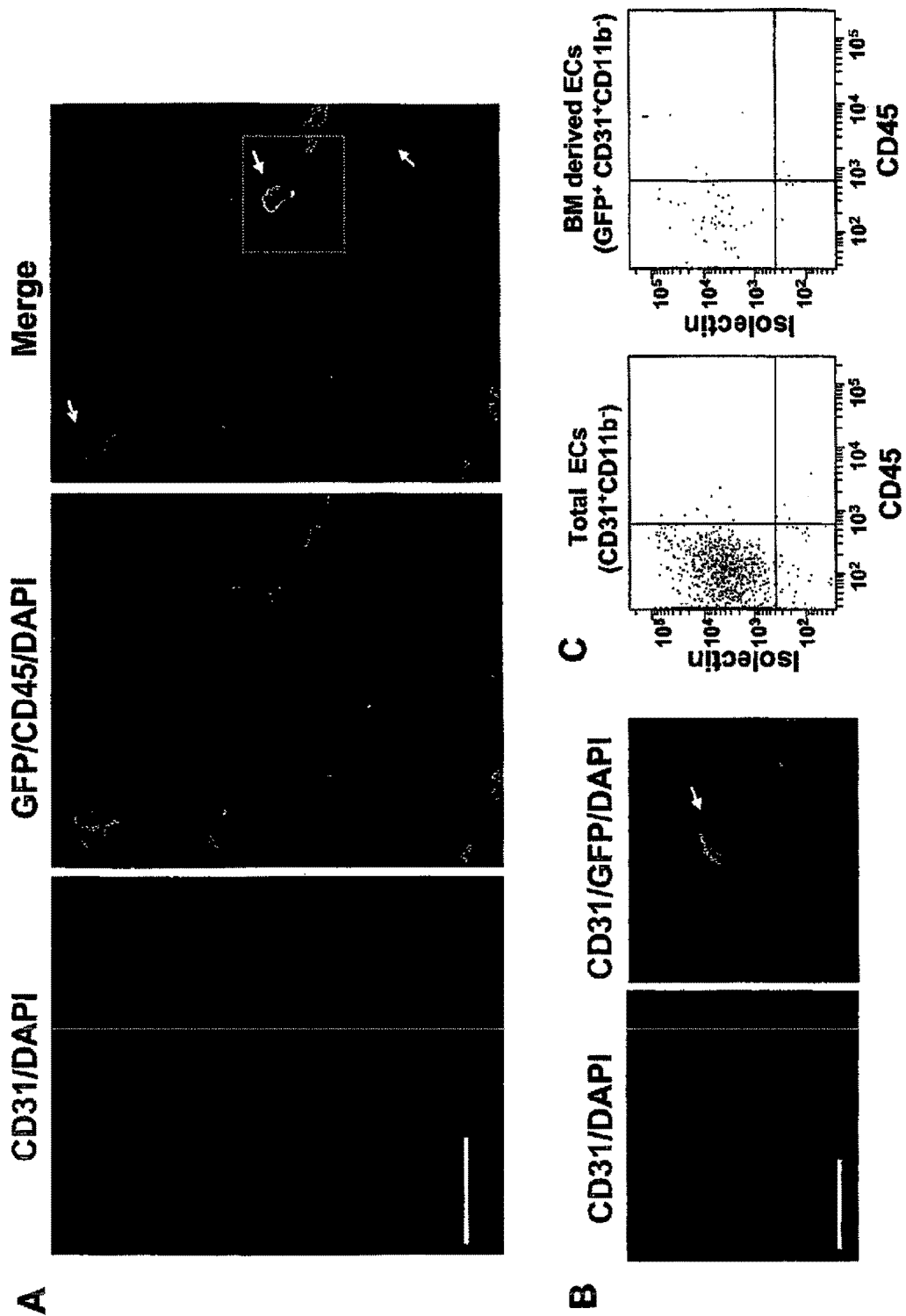
FIGS. 12A-C show that vessel incorporated BM-derived GFP$^+$ ECs do not express CD45.

B. BM-Derived Endothelial Cells Luminally Incorporate into Early Tumor Neovessels We next determined the contribution of BM-derived EPCs to neovessel formation in early vascular LLC tumors (days 6-8). These early vascular tumors were characterized by the presence of CD31+ neovessels of various sizes (FIG. 2A). A subset of these nascent sprouting vessels contained incorporated BM-derived GFP+ CD31+ VE-cadherin+ cells (FIG. 2A, arrows). High resolution microscopic analysis of these chimeric vessels showed that the vessel-incorporated BM-derived cells exhibited hallmarks of a mature endothelial cell (EC) such as, spindle-like morphology, high surface CD31 expression, and characteristic VE-cadherin staining at the intercellular adherent junctions (FIG. 2B). Optical sectioning (Z-stack resolution of 0.275 μm) further confirmed that the BM-derived endothelial cells had a single nucleus, and that the GFP and CD31 signals were localized to the same individual cell (FIG. 2C, FIG. 11A), indicating that the incorporated EC was derived from the BM. High resolution microscopy also allowed us to exclude false positives comprised of perivascular GFP+ cells intimately associated with vessels (FIGS. 11B and C), suggesting that low resolution light microscopy may lead to the overestimation of luminally incorporated BM-ECs as reported previously (Lyden et al., *Nat Med* 7, 1194 (2001); M. Garcia-Barros et al., *Science* 300, 1155 (2003)). It is worth noting that under all circumstances, BM-derived ECs were found in chimeric vessels with non-BM-derived ECs as opposed to vessels comprised exclusively of BM-derived ECs. Computer 3D rendering analysis confirmed that the VE-cadherin staining was shared between the GFP+ BM-derived EC and the non-BM derived EC in these chimeric vessels. The BM-derived GFP+ ECs also lacked expression of hematopoietic lineage markers including CD11b and CD45 as determined by both immunostaining of tumor sections and flow cytometry (FIGS. 12A-C). BM-derived EPCs and vessel-incorporated endothelial cells were also observed during early growth phase of other tumors, including melanomas (FIGS. 13A and B) and B6RV2 lymphoma. Taken together, these results demonstrate that in response to a tumor challenge, BM-derived EPCs, which are distinct from pro-angiogenic hematopoietic cells, are first recruited to early tumors followed by luminal incorporation of BM-derived endothelial cells into the neovessels.

Figure 3:
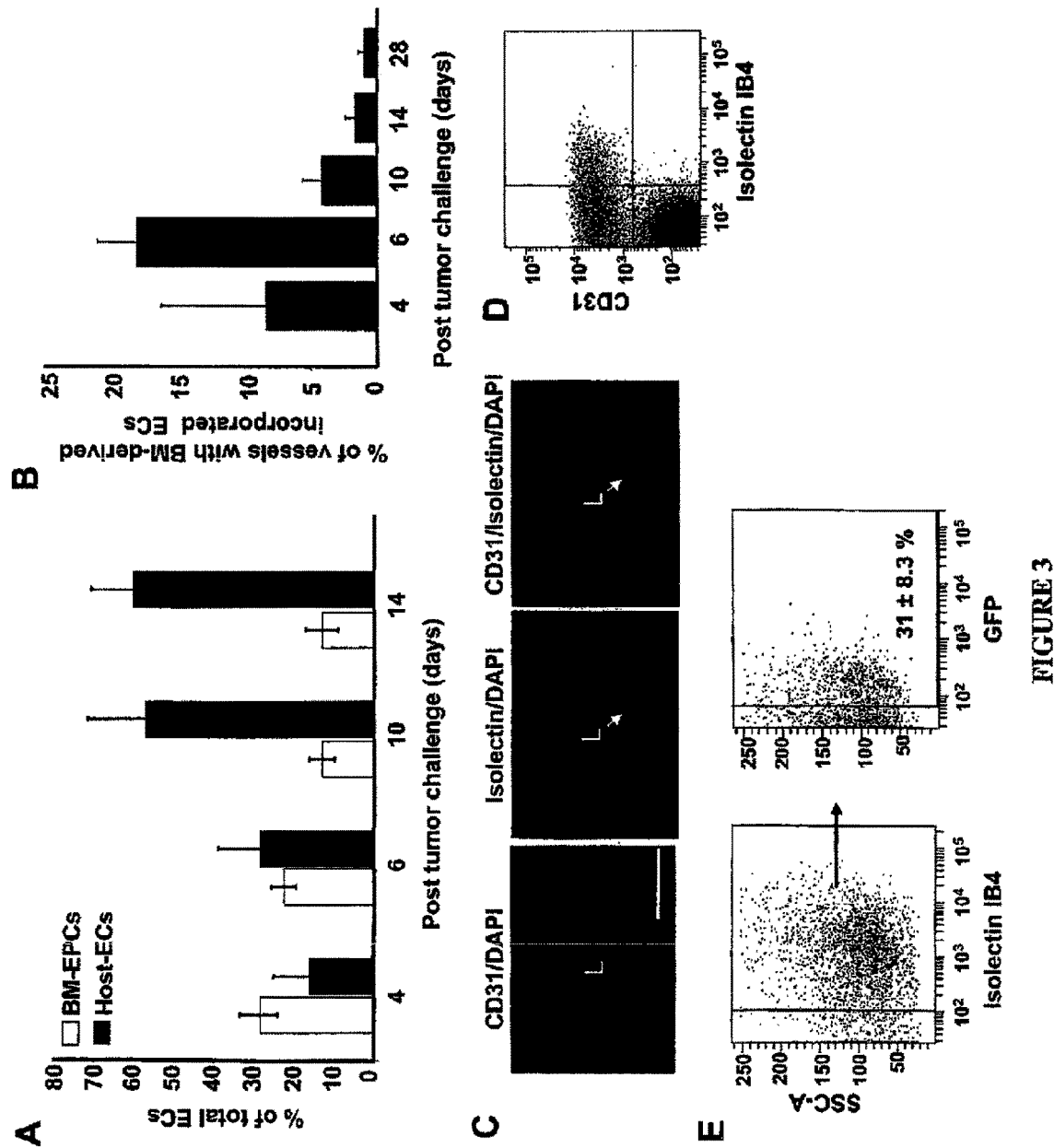
FIGS. 3A-E show contribution of BM-derived EPCs and endothelial cells as a function of tumor progression.
Figure 13:
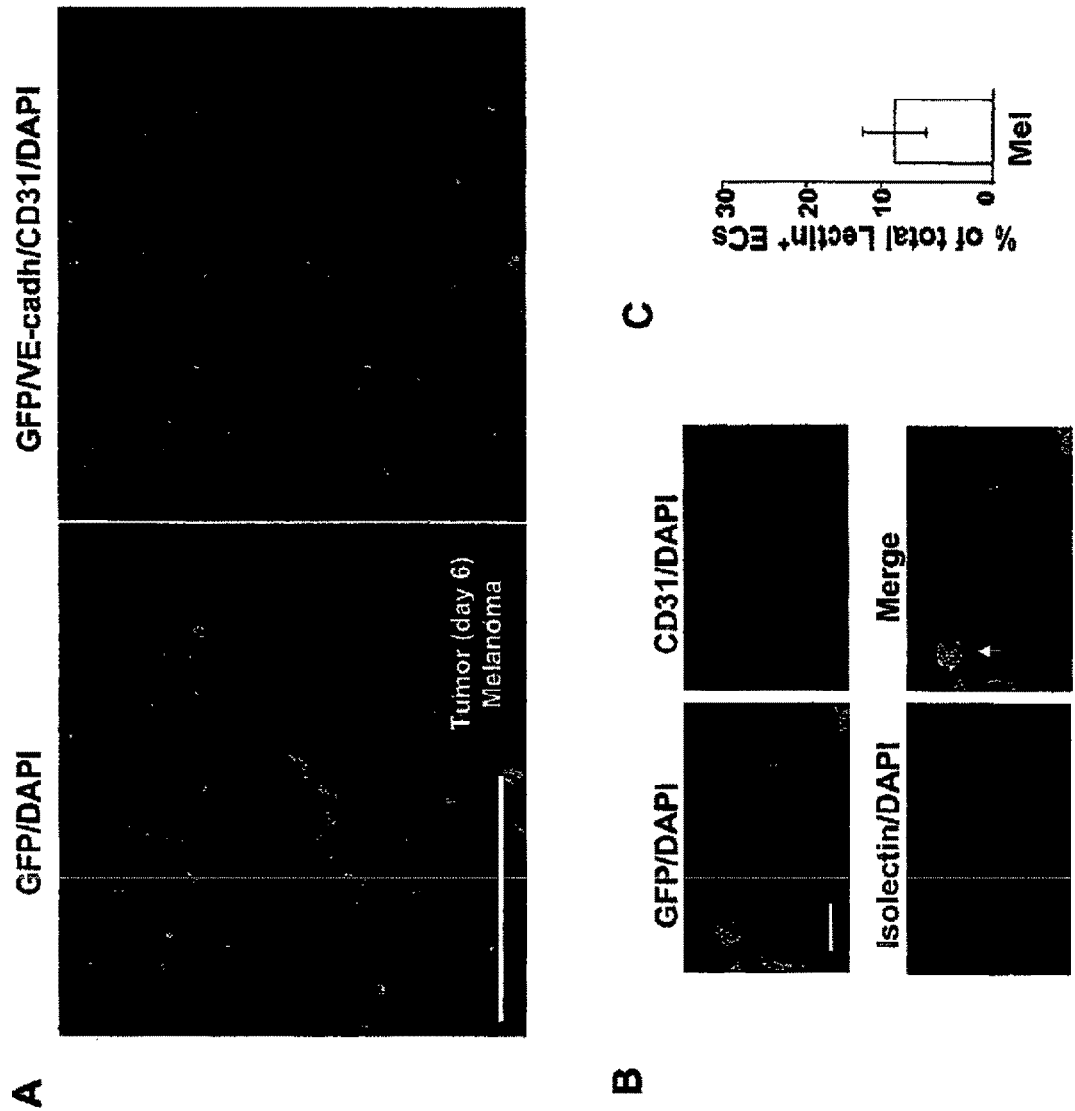
FIGS. 13A-C show that BM-derived EPCs and ECs contribute to B16F0 melanomas.
Figure 14:
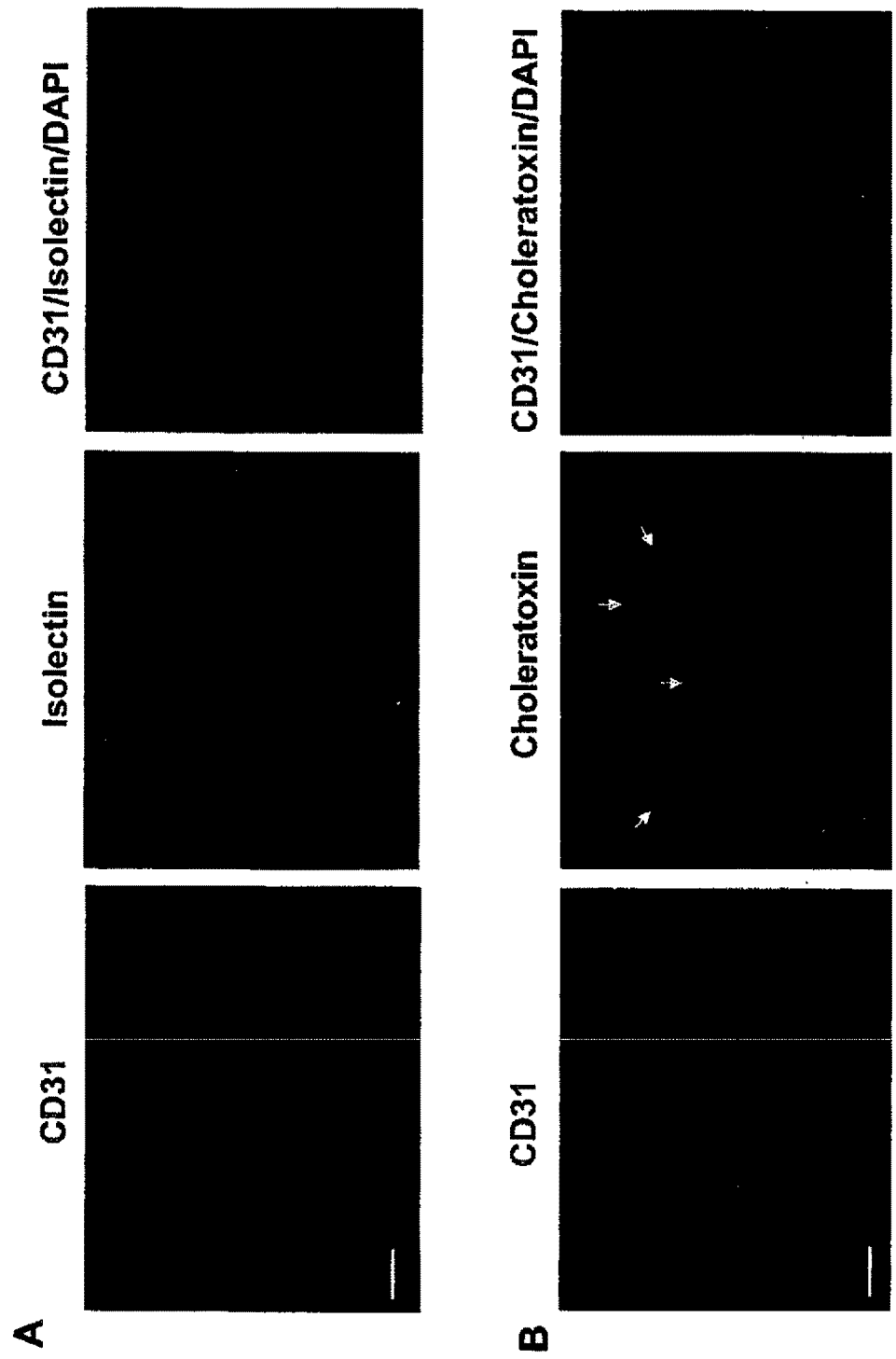
FIGS. 14A and B show that isolectin IB4 specifically stains functional tumor vasculature. They are a representative image showing that the Isolectin staining was tightly confined to the endothelial cells comprising the nascent vasculature (tumors, day 6) as compared to Choleratoxin β subunit. Tumor vasculature in animals perfused with: (A) isolectin GS-IB4 (Alexa Fluor 647) and stained with CD31 (Alexa Fluor 568); (B) choleratoxin (Alexa Fluor 647) and stained with CD31 (Alexa Fluor 568). Arrows indicate leakage of choleratoxin into the tumor mass. Scale bar, 50 μm.

We next performed flow cytometric analysis to determine the relative numbers of BM-derived EPCs (GFP+ VE-cadherin+ CD31$^{low}$ CD11b−) and non BM-derived EC (GFP− VE-cadherin+ CD31$^{high}$ CD11b−) at different stages of tumor growth (FIG. 3A). BM-derived EPCs comprised of 25-35% of the total endothelial cells in the early phases of tumor growth (day 4-6), and this contribution decreased about 4-folds in late tumors (day 14), consistent with histological analysis. Notably, in late tumors there was an enhanced recruitment of local non-BM-derived GFP− ECs (65%-75%, day 10-14), which diluted the observed contribution of BM-derived EPCs. We next quantified luminally incorporated BM-derived endothelial cells in tumor vessels. Vessel counts from optically sectioned tumors showed that about 20% of vessels had incorporated BM-derived ECs (GFP+ VE-cadherin+ CD31+) at day 6 (FIG. 3B), and these chimeric vessels markedly decreased with time (<1% remaining after 4 weeks). As an alternate approach to quantify luminal incorporation, we performed systemic perfusion with fluorescently labeled isolectin GS-IB$_4$, which stains specific carbohydrates on endothelial cells (Laitinen et al., *J Histochem Cytochem* 35, 55 (1987)). Analysis of tumor vessels with anti-CD31 antibody showed that isolectin GS-IB$_4$ staining was confined to the functional vessels (FIG. 14A) as compared to choleratoxin, which leaked into the surrounding tumor tissue (FIG. 14B). Furthermore, fluorescent isolectin specifically stained the luminal surface of endothelial cells in vessels (FIG. 3C, arrow), and these cells could be detected by flow cytometric analysis (FIG. 3D, upper right quadrant). We therefore used flow cytometric analysis to determine the percentage of luminally incorporated BM-derived endothelial cells in the tumor neovasculature. Of the total functional vasculature, as determined by Lectin+ CD31+ CD11b− cells, 31% (±8.3) of the luminal ECs (GFP+ Lectin+ CD31+ CD11b−) in day 6 LLCs (FIG. 3E) were BM-derived. A similar kinetic analysis performed in a melanoma model also showed recruitment of EPCs prior to vessel infiltration, early contribution of BM-derived endothelial cells, and their subsequent dilution by host endothelial cells (FIGS. 13 A-C). A comparison of the contribution of BM-derived EPCs and ECs in different tumors is summarized in Table 1.

TABLE 1

Contribution of BM-Derived EPCs and ECs to Growing Tumors*

| Stage | Lewis Lung Carcinoma | | Melanoma | | Breast Tumor | |
|---|---|---|---|---|---|---|
| | EPC | BM-EC | EPC | BM-EC | EPC | BM-EC |
| Early | 25-35% | 5-15% | 5-35% | 5-17% | n.d. | n.d. |
| Middle | 20-25% | 16-22% | 3-15% | 5-10% | n.d. | 5-10% |
| Late | 8-12% | 1-3% | 1-9% | 3-6% | n.d. | n.d. |

*BM-EPCs and ECs were quantified as a percentage of total endothelium. EPC contribution was determined by flow cytometric analysis. BM-derived luminally incorporated EC contribution was determined by high resolution microscopy or flow cytometry.
n.d.: not determined.

Together, these results demonstrate that BM-derived EPCs are recruited to early avascular tumors. EPCs differentiate into endothelial cells and luminally incorporate into a subset of sprouting peripheral vessels from the host. This is followed by massive invasion of peripheral vasculature into the tumor mass diluting the BM-derived vessels at late stages of tumor growth.

C. BM-Derived EPCs Contribute to Spontaneous Tumors

In order to confirm that these events are also taking place in spontaneous tumors, we performed a similar analysis in breast tumors arising in MMTV-PyMT transgenic mice (Guy et al., *Mol Cell Biol* 12, 954 (1992)). In these animals the PyMT oncogene is expressed under the transcriptional control of the mouse mammary tumor virus promoter/enhancer specifically in the mammary epithelium (Guy et al., supra). The PyMT transgene activates pathways similar to that induced by ErbB2 (Desai et al., *Proc Natl Acad Sci USA* 99, 6967 (2002)), and importantly, this murine tumor model recapitulates human breast cancer progression from early nonmalignant hyperplasia (about 6 weeks of age) and adenoma (8 to 9 weeks of age), to early and late malignant adenocarcinoma (8 to 12 weeks of age) (Lin et al., *Am J Pathol* 163, 2113 (2003)).

Figure 4:
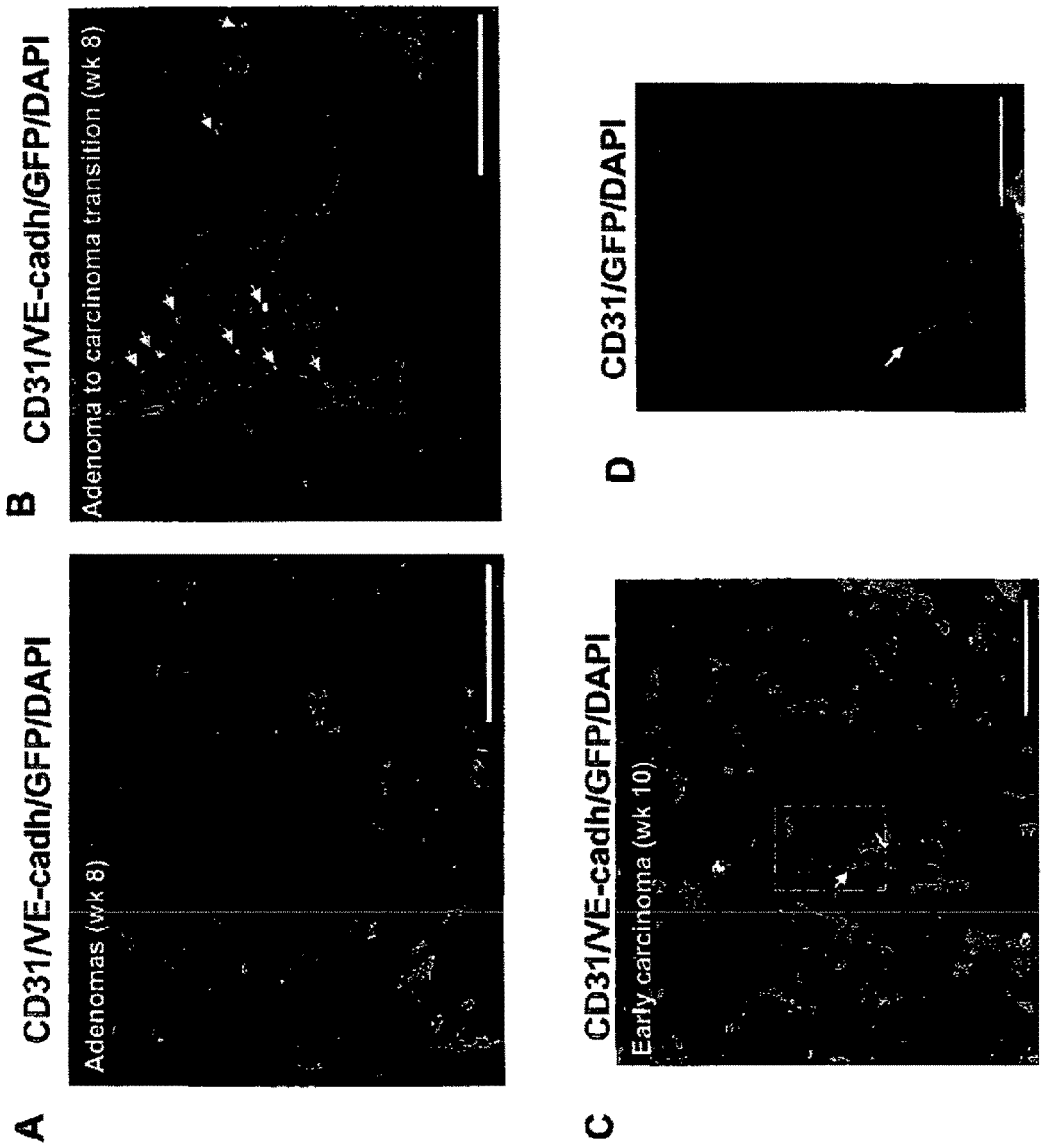
FIGS. 4A-D show contribution of BM-derived EPCs in spontaneous breast tumors.

We examined the contribution of BM-derived EPCs and luminally incorporated endothelial cells at various stages of these mammary tumors developing in animals previously transplanted with GFP$^+$ BM. Early adenomas (about 8 week of age) were identified as closely packed multifocal acini surrounded by preexisting host vessels (FIG. 4A, arrows). Adenomas at this stage had not yet recruited neovasculature from the preexisting vessels, and very few GFP$^+$ BM cells were observed infiltrating the adenoma mass (FIG. 4A). A subset of adenomas progressing into early carcinoma showed foci of BM-derived GFP$^+$ cells including EPCs (FIG. 4B, arrows). Such foci of BM-derived cell infiltration have been previously observed in adenomas (Lin et al., *Am J Pathol* 163, 2113 (2003)). Analysis of early carcinomas (10 weeks of age) showed high density of BM infiltration and increased vessel density. These vascular tumors were characterized by the presence of CD31$^+$ neovessels of various sizes (FIG. 4C). These sprouting nascent vessels had incorporated BM-derived GFP$^+$ CD31$^+$ECs (FIG. 4C). In this model, quantification of luminally incorporated BM-derived ECs by flow cytometry was technically challenging due to the closely packed, multi-focal nature of breast tumor development. We therefore performed vessel counts by microscopy of early carcinomas, which showed that approximately 5-10% of host vessels had incorporated BM-derived GFP$^+$ endothelial cells (GFP$^+$ VE-cadherin$^+$ CD31$^+$). The observation that BM-derived EPCs precede host endothelial cells and that BM-ECs contribute to neovascularization in early stages of breast tumor progression is consistent with that observed in transplanted tumors, highlighting the general relevance of these cells in tumor neovasculatization.

Figure 5:
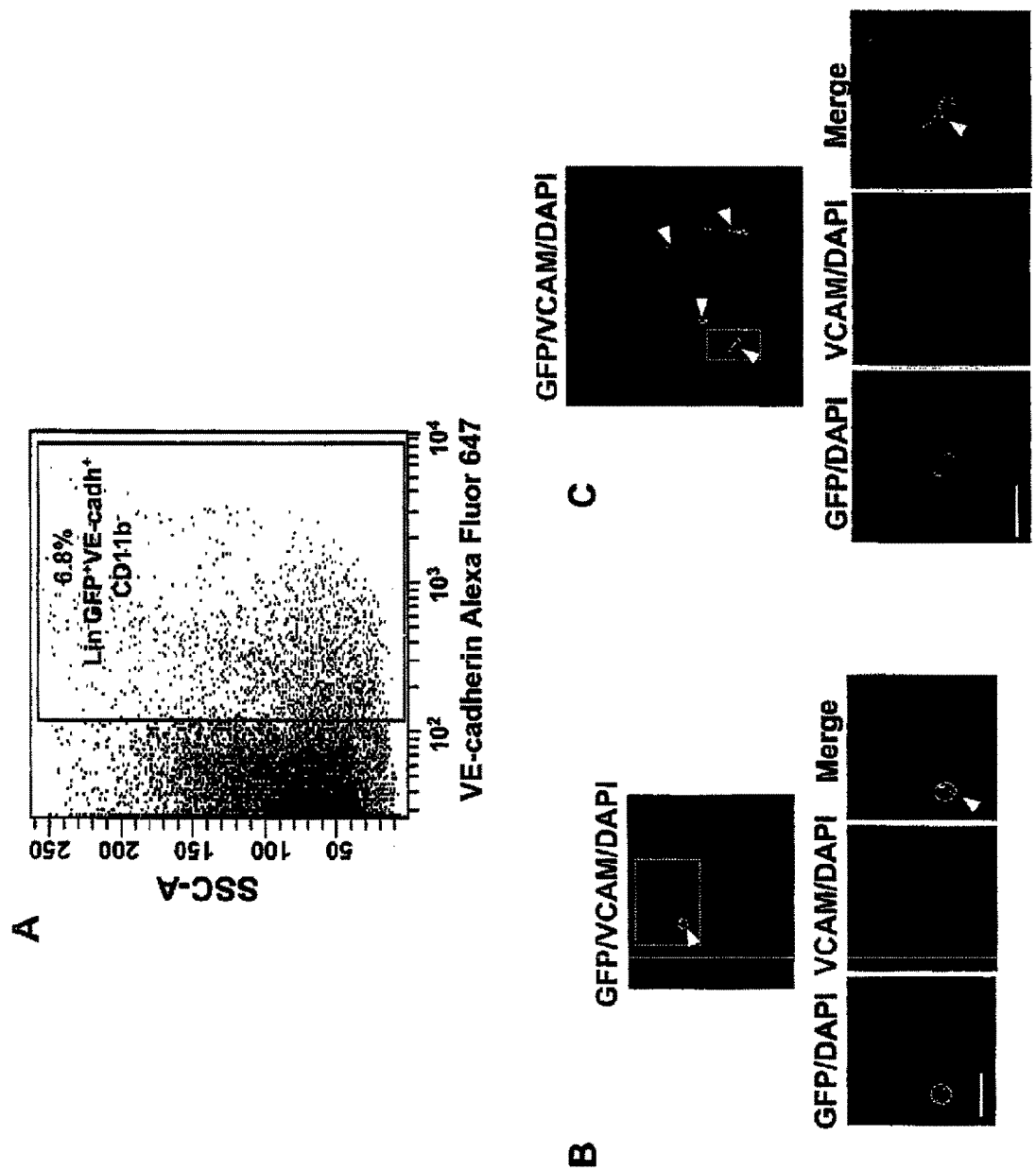
FIGS. 5A-C show BM-derived endothelial progenitor cells differentiate into mature endothelial cells and incorporate into vascular networks.
Figure 15:
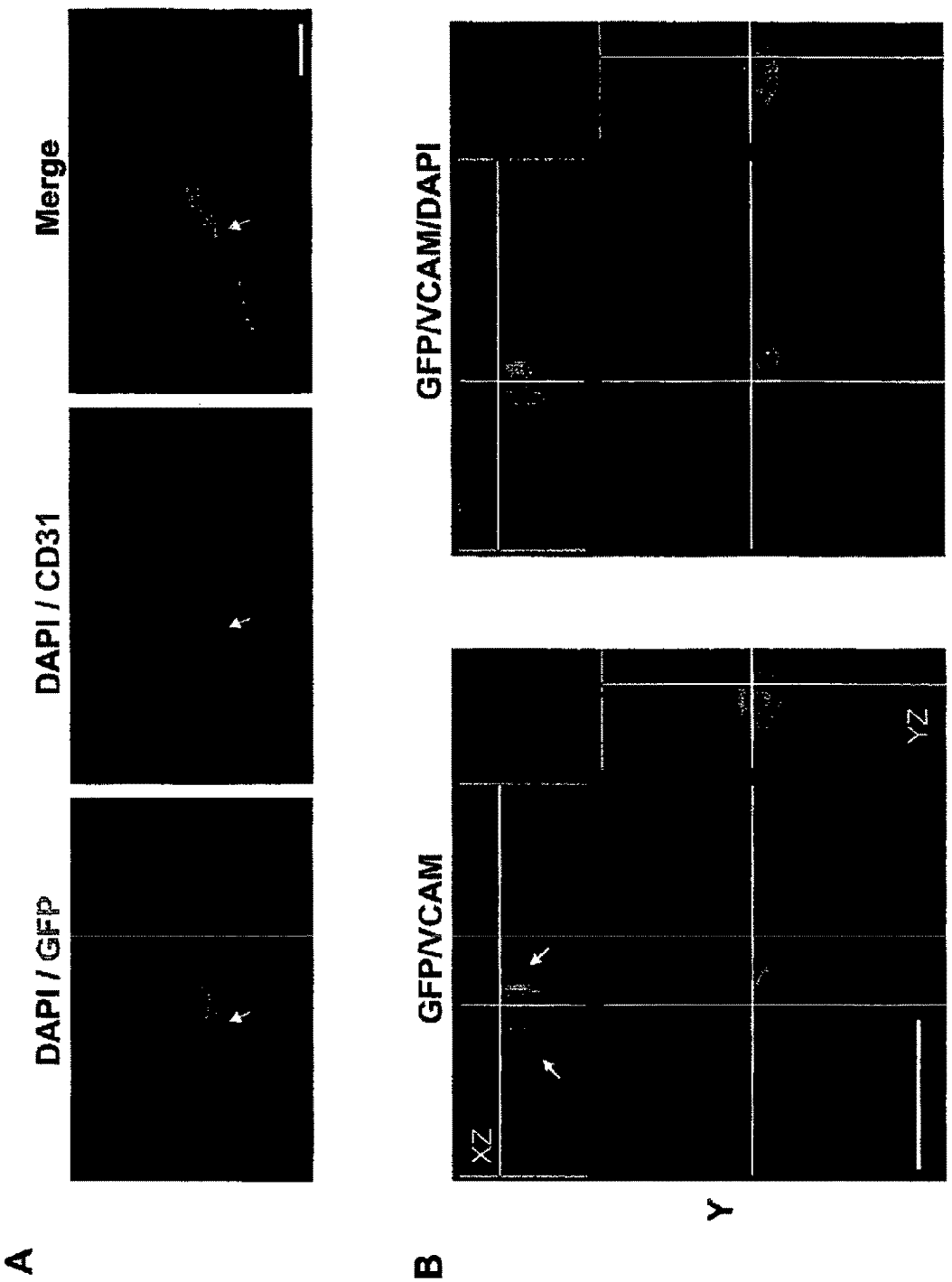
FIGS. 15A and B show data of high resolution analysis of an incorporated BM-derived EC in vascular network in matrigel.
FIG. 15B is a high resolution image of a portion of a vascular network showing an incorporated GFP+ VCAM+ EC. Optical sectioning of the incorporated GFP+ EC showing that VCAM and GFP are expressed by the same individual vessel-incorporated cell (see yellow arrows in the XZ axis, left panel, top). Scale bar, 20 μm.

D. BM-Derived EPCs Differentiate into Endothelial Cells and Incorporate into Vessels We next sought to formally demonstrate that BM-derived EPCs have the potential to differentiate into mature endothelial cells and incorporate into neovessels. First, we sorted GFP$^+$ EPCs (Lin$^-$ VE-cadherin$^+$) from the bone marrow by flow cytometry (FIG. 5A), and co-cultured them with spontaneously immortalized murine endothelial cells, mHEVc (Cook-Mills, et al., *In Vitro Cell Dev Biol Anim* 32, 167 (1996)), in matrigel. Notably, mHEVcs in culture have lost CD31 and VE-cadherin expression, but have retained VCAM expression (Cook-Mills et al., *In Vitro Cell Dev Biol Anim* 32, 167 (1996)). By 12 hours, VE-cadherin$^+$ EPCs had not differentiated into endothelial cells and remained VCAM negative (FIG. 5B). However, by day 2, GFP$^+$ BM-ECs that had incorporated into the growing vascular networks were detected (FIG. 3D, upper panel). These incorporated GFP$^+$ BM-ECs expressed VCAM (FIG. 5C, lower panel), and CD31 (FIG. 15A). High resolution microscopy confirmed that the incorporated EC was indeed derived from the GFP$^+$ EPC (FIG. 15B). We next determined whether or not the EPCs recruited to early tumors differentiated into endothelial cells and incorporated into neovessels. GFP$^+$ VE-cadherin$^+$ CD11b$^-$ EPCs were flow-sorted from early tumors (day 4 LLC tumors) and GFP$^+$ VE-cadherin$^-$ CD11b$^+$ hematopoietic cells. EPCs identified as CD31$^{low}$ was co-cultured with mature ECs (non-GFP) in 3D matrigel for 48 hours. By day 2, GFP$^+$ EPCs had differentiated into GFP$^+$ ECs and incorporated into the vascular networks. In contrast, GFP$^+$ CD11b$^+$ hematopoietic cells isolated from the same early tumors, when similarly co-cultured with mature ECs (non-GFP) in 3D matrigel gel for 48 hours, neither differentiated into endothelial cells nor incorporated into vessels. Collectively, these results demonstrate that BM-derived VE-cadherin$^+$ EPCs contribute to the endothelial lineage.

In sum, our studies showed that BM-derived EPCs, as defined by the cell surface expression of VE-cadherin, VEGFR2, CD31$^{low}$, Endoglin and Prominin I/AC133 (see Table 2 below), differentiated into mature endothelial cells and contributed both structurally and functionally to tumor angiogenesis. Further analysis demonstrated that the EPCs were distinct from other hematopoietic and pro-angiogenic BM-derived cell types such as Tie2-expressing monocytes (De Palma et al., supra), macrophages (Pollard, supra), recruited BM-derived circulating cells (Grunewald et al., supra), pericyte progenitors (Song et al., supra), infiltrating neutrophils (Nozawa et al., supra). The BM-derived ECs are also distinct from vascular leukocytes (Conejo-Garcia et al., supra), because they do not express leukocyte marker CD45.

TABLE 2

Cell Surface Markers on BM-Derived EPCs and ECs*

| Markers | BM-derived EPCs | BM-derived ECs |
|---|---|---|
| VE-cadherin | + (Uniform) | + (Junction) |
| CD31 | Low | High |
| VEGFR2 | + | + |
| Endoglin | + | + |
| VCAM | − | + |
| Prominin 1 | + | − |
| Isolectin | − | + |
| CD11b | − | − |
| CD45 | − | − |
| CD41 | − | − |

*Flow cytometry and/or immunofluorescence microscopy were used to determine markers on BM-derived EPCs and ECs. Low: low expression level; high: high expression level.

Analysis of multiple tumor types showed that EPCs differentiated into mature ECs and luminally incorporated into neovessels, clearly demonstrating the derivation of tumor vasculature from transplanted BM cells. A systematic kinetic analysis showed that EPCs were recruited to the tumor periphery preceding vessel formation, and were luminally incorporated into a subset of sprouting tumor neovessels. These chimeric BM-derived vessels were eventually diluted with host-derived vessels, thereby explaining the low contribution observed by other investigators in large, established tumors (De Palma et al., 2003 and 2005, supra; Gothert et al., supra; Rajantie et al., supra; Larrivee et al., *J. Immunol.* 175 (5):2890-2899 (2005); Duda et al., *Blood* 107(7):2774-2776 (2006)).

Our studies showed that luminal incorporation could be reliably quantified by flow cytometry in the context of specific isolectin administration and analysis of Isolectin$^+$ CD31$^+$GFP$^+$ CD11b$^-$ cells. GFP determined BM derivation;

isolectin ensured luminal incorporation; CD31 confirmed endothelial cells; and CD11b gated out any hematopoietic contribution in the CD31 channel. This approach was critical because CD31 was also expressed by a subset of hematopoietic cells (Baumann et al., *Blood* 104(4):1010-1016 (2004)), and therefore the use of CD31 alone, as previously done by other groups (e.g., Spring et al., *Proc Natl Acad Sci USA* 102(50):18111-18116 (2005)), provided an unreliable measure of bona fide endothelial cells.

Figure 6:
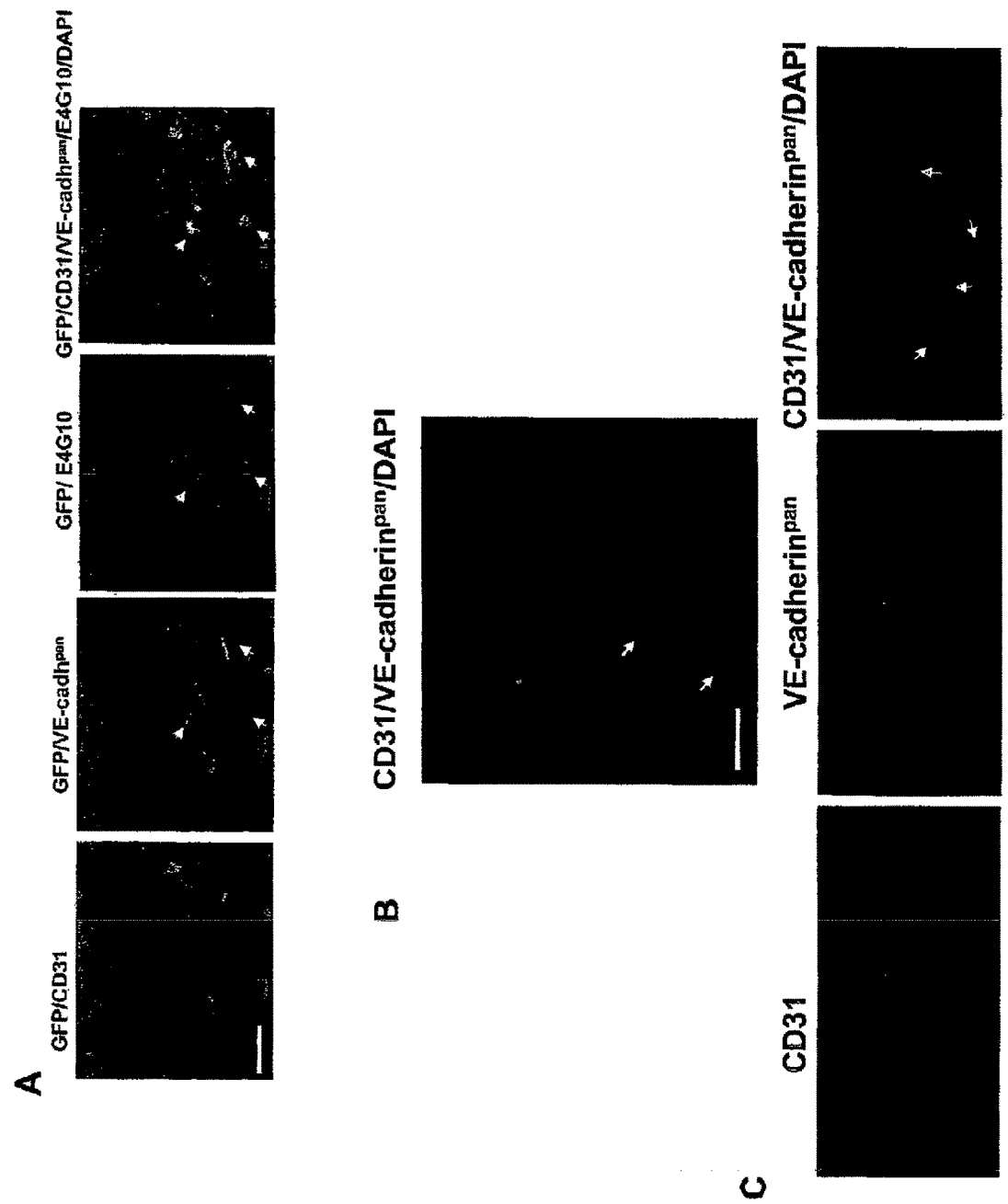
FIGS. 6A-C show that VE-cadherin monoclonal antibody E4G10 specifically recognizes EPCs and not mature endothelial cells.
Figure 16:
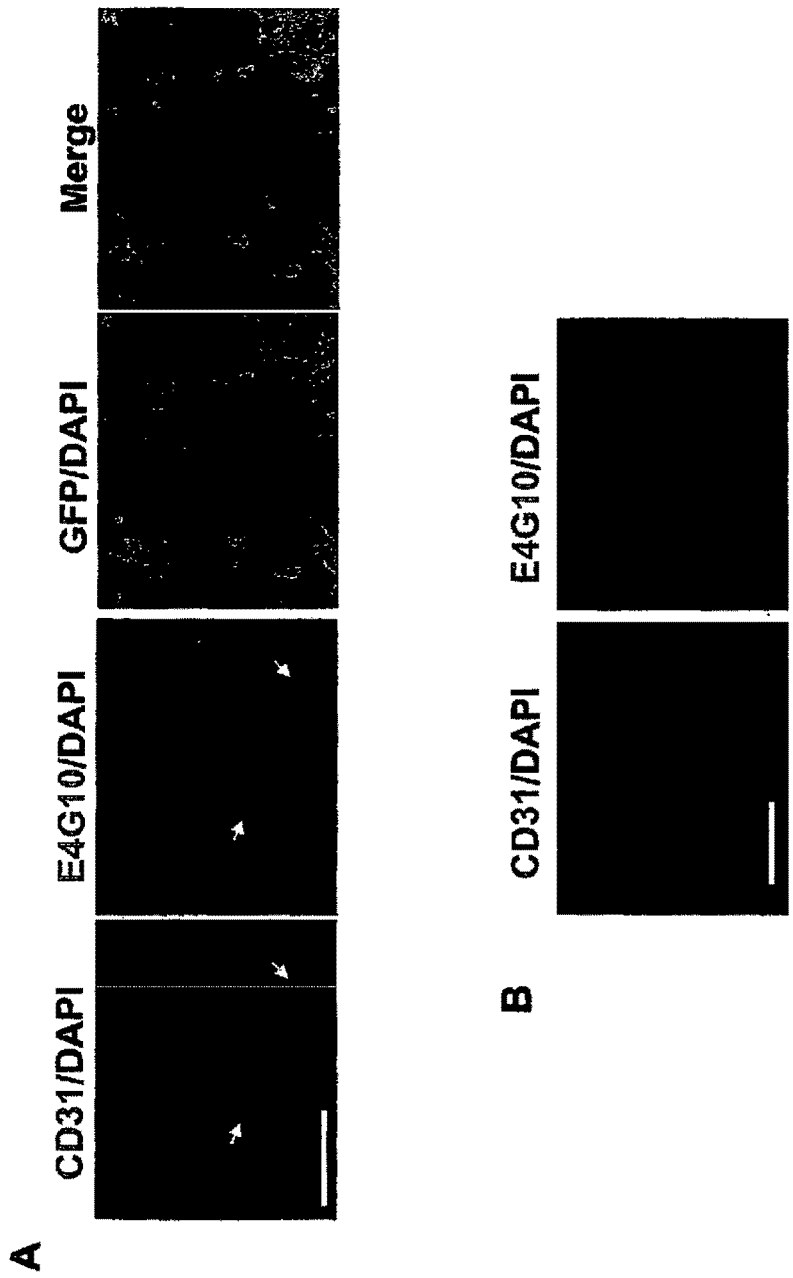
FIGS. 16A and B show that the anti-VE-cadherin antibody E4G10 recognizes EPCs and not ECs in vessels. Immunostaining of early tumors (day 6) with CD31 and VE-cadherin antibody E4G10.
FIG. 16B shows that in early tumors, endothelial cells in the nascent vasculature do not show E4G10 staining. Scale bar 20 μm.

E. Specific Ablation of EPCs Results in Defects in Angiogenesis-Mediated Tumor Growth To determine if the BM-derived EPCs had a functional role in angiogenesis-mediated tumor growth, we selectively ablated EPCs with an anti-VE-cadherin antibody, E4G10. The monoclonal antibody E4G10 specifically recognizes the exposed monomeric epitope on the immediate N-terminus of VE-cadherin, which becomes masked upon trans-dimerization in mature endothelial cells in vessels (May et al., *Blood* 105, 4337 (2005)). Thus, E4G10 allows targeting of monomeric VE-cadherin present on EPCs, but not the dimerized form present in vessel incorporated endothelial cells. We confirmed that E4G10 recognizes VE-cadherin only on the EPCs, but not in mature endothelial cells comprising the nascent early tumor neovessels (FIG. 6A, white arrows, FIGS. 16A and B), compared to a pan VE-cadherin antibody 11D4.1 (VE-cadh$^{pan}$) that recognized both the monomeric VE-cadherin on EPCs and homodimerized VE-cadherin on endothelial cells in vessels (FIG. 6A, red arrows). In addition, the VE-cadherin epitope was exposed in neither the luminally incorporated BM-derived GFP$^+$ endothelial cells, nor the endothelial cell projections of sprouting nascent vessels in early tumors (FIGS. 6B and C).

Figure 7:
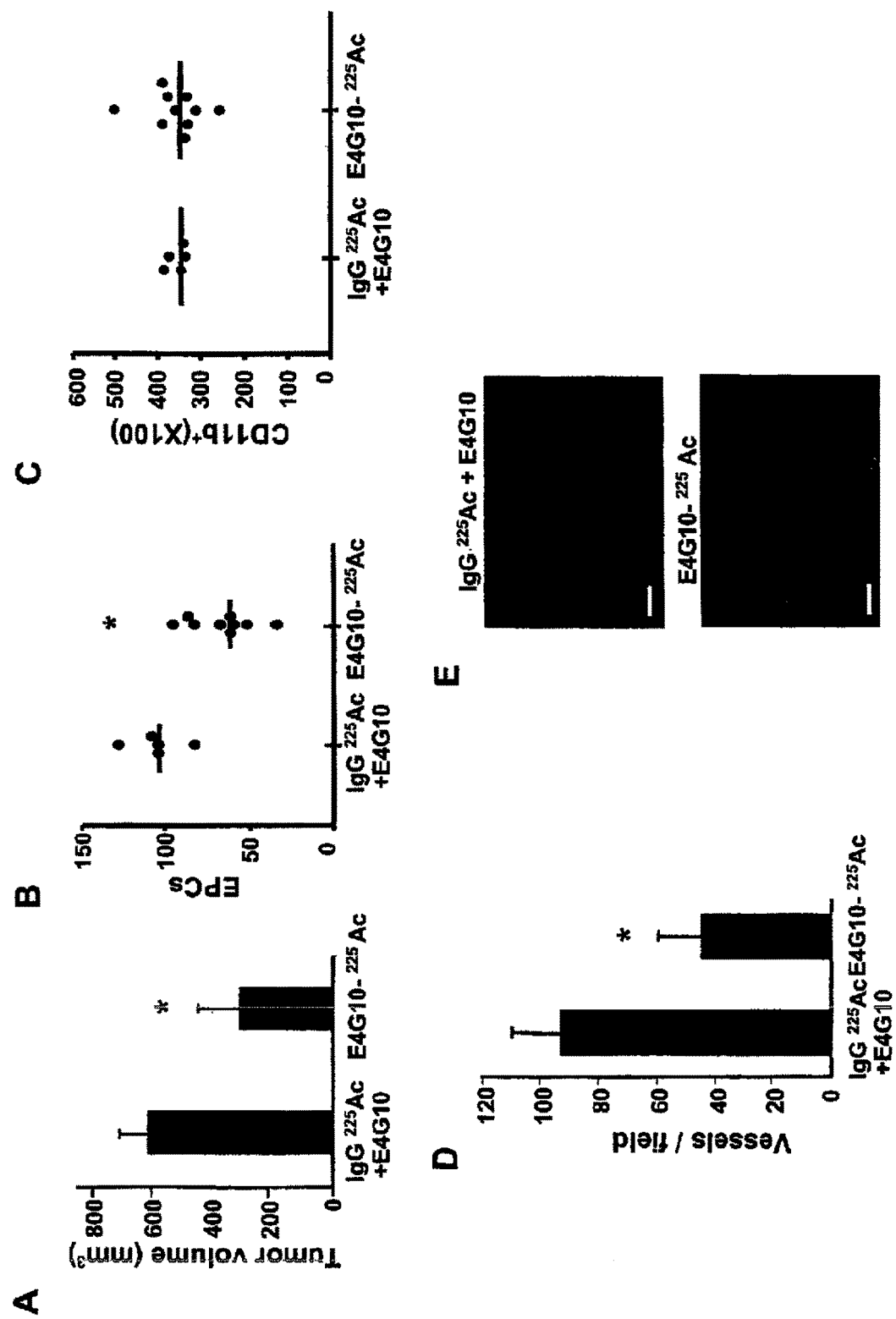
FIGS. 7A-E show that selective ablation of endothelial progenitor cells results in delayed tumor growth in vivo.

The cytotoxic potency of E4G10 was enhanced by coupling the antibody to an alpha particle emitting isotope, actinium-225 ($^{225}$Ac) (McDevitt et al., *Science* 294, 1537 (2001)), so that target cells could be effectively killed at low concentrations of the antibody. Administration of $^{225}$Ac-labeled E4G10 (50 nCi, 0.6 µg antibody per administration/animal) reduced accumulated LLC tumor burden per animal by approximately 50% (day 14, p=0.001) compared to the administration of equivalent amounts of $^{225}$Ac-labeled IgG isotype control mixed with unlabeled E4G10 (FIG. 7A). The impaired tumor growth was associated with a marked reduction in EPC contribution (>45%, p=0.004) as determined by flow cytometry (FIG. 7B) and confirmed by histology. Ablation of VE-cadherin$^+$ cells was specific, since no detectable change was observed in other BM-derived GFP$^+$ infiltrating cell populations, including the CD11b$^+$ hematopoietic cells available in the immediate proximity (FIG. 7C, p=0.86). Notably, ablation of VE-cadherin$^+$ EPCs resulted in a 40% reduction in BM-derived luminally incorporated ECs (GFP$^+$ CD31$^+$Isolectin$^+$ CD11b$^-$) (p=0.016, data not shown), and a dramatic reduction in vessel density (p=0.006) in later tumors (FIGS. 7D and E). No gross or histopathological toxicity was observed in normal tissues or their vasculature at the dosage administered. Taken together, these results suggest that ablation of EPCs results in marked delay in tumor growth associated with decreased vessel density.

Materials and Methods

Cell Lines and Growth Conditions

The murine lymphoma cell line B6RV2 (Lyden et al., *Nat Med* 7, 1194 (2001)), Lewis lung carcinoma cell line LLCs/D122 (provided by Lea Eisenbach, Wiesmann Institute of Science, Rehovot, Israel), and melanoma cell line B16F0 (ATCC) were used for generating tumors in C57BL/6 mice. LLCs and B16F0 were maintained in DMEM supplemented with 10% fetal bovine serum. B6RV2 cells were maintained in RPMI with 15% FBS. Murine endothelial cells, mHEVc were cultured as described (Cook-Mills et al., *In Vitro Cell Dev Biol Anim* 32, 167 (1996); Tudor et al., *Biochem Cell Biol* 78, 99 (2000)).

Spontaneous Tumor Model

Male PyMT mice (obtained from mouse models of human cancer consortium, NCI) on a FVB/N background were randomly bred with FVB/N females (Jackson Labs) lacking the PyMT transgene to obtain female mice heterozygous for the PyMT transgene. These female carriers developed mammary tumors by 5-6 which were staged according to Lin et al., *Am J Pathol* 163, 2113 (2003).

BM Isolation, Lin$^-$ Cell Purification and Transplantation.

GFP transgenics, C57BL/6-Tg (ACTbEGFP) 10sb/J or FVB.Cg-Tg(GFPU)5Nagy/J (The Jackson Laboratory, Bar Harbor, Me.), were used as the donor strain. In these strains, GFP was driven by a hybrid chicken β-actin promoter and cytomegalovirus intermediate early enhancer. BM cells were harvested by flushing femurs and tibias of adult animals. $1 \times 10^7$ total BM cells were transplanted into lethally irradiated (1100 rads) recipients. Lin$^-$ cells were enriched using the Lineage Cell Depletion Kit (CD5, CD45R (B220), CD11b, anti-Ly-6G (Gr-1), 7-4, and Ter119 antibodies, and a magnetic separation device, MACS (Milteyni Biotech, Auburn, Calif.). The purity of the Lin$^-$ fraction was determined using a fluorescent antibody specific for lineage specific markers by flow cytometry.

Flow Cytometry, Tumor Growth, Immunohistochemistry and Microscopy

C57BL/6 mice were inoculated intradermally with ($5 \times 10^6$-$2 \times 10^7$ LLC/D122 or B6RV2 cells, or with $5 \times 10^5$ B16F0 cells and tumor size was monitored (width$\times 0.5$ length$^2$).

Tumors were excised from sacrificed animals, minced, and then digested at 37° C. for 45-60 min with an enzyme cocktail (Collagenase A, elastase, and DNase I, Roche Applied Science) and filtered through a 30-µm strainer. Single cell suspensions were pre-blocked with Fc block (CD16/CD32, BD Biosciences PharMingen) and then incubated with the following primary antibodies from Pharmingen: rat IgG2aκ and IgG2aβ isotype control, CD31/PECAM-1 (clone MEC 13.3); VE-cadherin/CD144 (clone 11D4.1); CD11b (clone M1/70.), VEGFR2/Flk1 (clone avas12alpha1). Labeled cell populations were measured by LSRII flow cytometer (Beckton Dickenson), compensation for multivariate experiments was performed with FACS Diva software (Becton Dickinson Immunocytometry Systems, Franklin Lakes, N.J., USA). Flow cytometry analysis was performed using a variety of controls such as, isotype antibodies, FMO samples 55, and unstained samples for determining appropriate gates, voltages, and compensations required in multivariate flow cytometry. Tumor bearing mice were anesthetized and then perfused with phosphate buffer followed by 4% paraformaldehyde. In some cases animals were injected with Alexa Fluor 647 conjugated isolectin GS-IB4 or Choleratoxin β subunit (50 µg for 10 min, Molecular Probes) prior to phosphate buffer perfusion. Tumors were incubated overnight in paraformaldehyde, followed by 20% sucrose, and cryoembedded in Tissue-tek O.C.T. embedding compound (Electron Microscopy Sciences). Immunohistochemistry was performed using the primary antibodies, Prominin1 (Clone 13A4) (eBiosciences), Endoglin (clone MJ7/18), CD45RB (Clone 16A), pan CD45 (Clone 30-F11), CD41 (Clone MWREQ30) (BD Pharmingen), and E4G10 (ImClone) in addition to antibodies described for flow cytometry on 30 µM thick sections. Usually primary antibodies were directly conjugated to various Alexa Fluor dyes or Quantum Dots using antibody labeling kits (Inivtrogen) performed as per manufacturer's instructions. In the case of Alexa Fluor 750, conjugations were performed using succinimidyl esters and purified over BioSpin P30 Gel (Biorad). GFP positive cells were detected by their own signal.

Fluorescent images of endothelium that contained donor-derived endothelial cells were obtained using a computerized Zeiss fluorescent microscope (Axiovert 200M), fitted with an apotome and a HRM camera. Images were analyzed by using Axiovision 4.5 software. The average depth of the optical sections was 30 µm, with a resolution of 0.275-0.35 µm.

EPC Differentiation Assay

Total BM cells from GFP transgenic animals were first enriched for Lin⁻ cells as described before. Lin⁻ cells were incubated with VE-cadherin (Alexa Fluor 647) and CD11b (Alexa Fluor 750) antibodies. Using multivariate flow sorting a pure GFP$^+$ EPC population (VE-cadherin$^+$ CD11b$^-$) was collected by FACS Aria (BD Biosciences). Approximately 5000 EPCs were co-cultured with $5\times10^4$ murine endothelial cells, mHEVc (gift from Cook-Mills) on matrigel (BD Biosciences) supplemented with Medium 200 and LSGS (Cascade Biologics). Similarly, EPCs ($1\times10^3$) and hematopoietic cells (approximately $5\times10^4$) were flow sorted from early tumors (day 4) derived from GFP$^+$ BMT animals and co-cultured with $5\times10^4$ murine endothelial cells. Low CD31 expression on EPCs was confirmed with a PE-conjugated CD31 antibody. Immunostaining was directly performed on matrigels with VCAM (clone 429, MVCAM.A, BD Pharmingen), and CD31/PECAM-1 (clone MEC 13.3) antibody after fixation with 4% paraformaldehyde.

Preparation and Administration of Radioimmunoconjugate $^{225}$Ac (Oak Ridge National Laboratory, Oak Ridge, Tenn.) was conjugated to E4G10 (ImClone, N.Y.) using a two-step labeling method, as described (Borchardt et al., *Cancer Res* 63, 5084 (2003); M. R. McDevitt et al., *Appl Radial Isot* 57, 841 (2002)). Radio-purity and immunoreactivity of the radioimmunoconjugate (RIC) was determined, as described (Borchardt et al., supra). Mice were anesthetized and injected intravenously with the RIC in 100 µl at days 3, 5, 8, and 12 (50 nCi, 0.6 µg antibody per administration).

Statistical Analysis

Analysis of different treatment groups were performed using the Mann-Whitney T test.

EXAMPLE 2

In cancer patients malignant tumor cells disseminate from their site of origin, metastasize and colonize distant organs resulting in drastic morbidity and mortality. In the last few years, a major focus of research has been to identify molecular mediators of metastasis (Minn et al., *Nature* 436, 518 (2005); Steeg, *Nat Med* 12, 895 (2006)) and delineate mechanisms that govern tumor-cell homing and colonization of specific organ sites (Gupta and Massague, *Cell* 127, 679 (2006)). Recently, tumor-specific "pre-metastatic niche" formed by BM-derived VEGFR1$^+$ hematopoietic cells has been implicated in the establishment of metastatic colonies (Kaplan et al., *Nature* 438, 820 (2005); Hiratsuka et al. *Nat Cell Biol* 8, 1369 (2006)). Following initial colonization, these metastatic colonies usually remain microscopic or dormant (Naumov et al., *J Natl Cancer Inst* 98, 316 (2006); Townson and Chambers, *Cell Cycle* 5, 1744 (2006)), and may eventually progress into macrometastases leading to drastic morbidity and mortality as a consequence of organ dysfunction (Gupta and Massague, supra; Chambers et al., *Nat Rev Cancer* 2, 563 (2002)). However, despite these advances little is known about how, following initial colonization, micrometastases develop into deadly macrometastases.

The process of metastasis is inextricably linked to angiogenesis (Hanahan et al., supra; Naumov et al., supra). In primary tumors, an angiogenic switch is a necessary step to sustain its progressive expansion into a malignant form. Moreover, the neovasculature provides avenues for malignant cells to escape the primary site to establish metastatic lesions in secondary organs. Once the cells arrive at the metastatic site, they usually remain dormant (Townson et al., supra). In some cases, the micrometastases may activate the angiogenic switch to sustain further growth (Naumov et al., supra; Holmgren et al., *Nat Med* 1:149-153 (1995)). However, the cellular and molecular mechanisms regulating the angiogenic switch and the dynamics of vessel assembly during the progression of micrometastases to macrometastases remain poorly understood. This has limited the utility of anti-angiogenic approaches in controlling progression of metastatic lesions.

Figure 21:
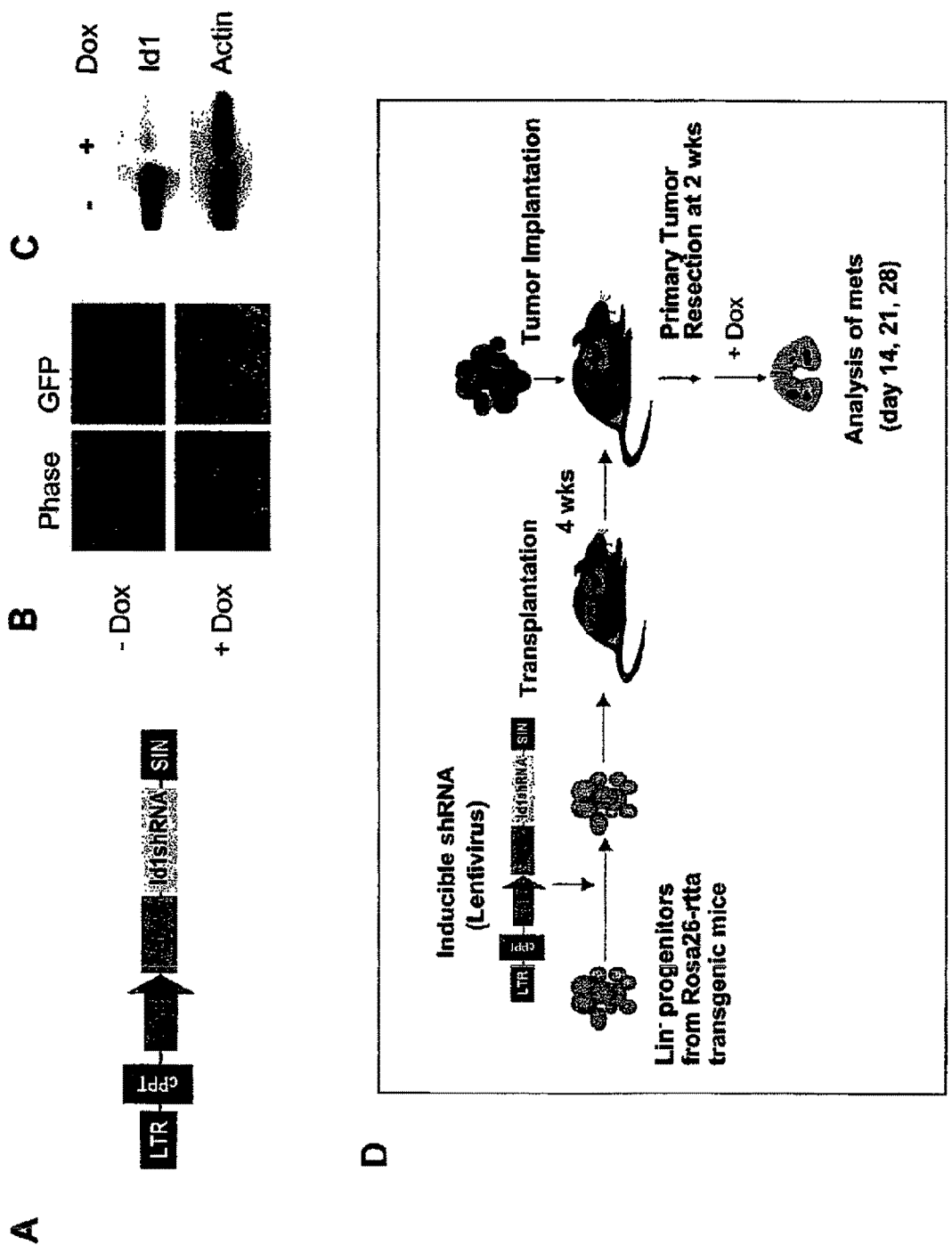
FIGS. 21A-D show a doxycycline-mediated inducible shRNA expression system for suppressing cognate genes in BM progenitors.
Figure 22:
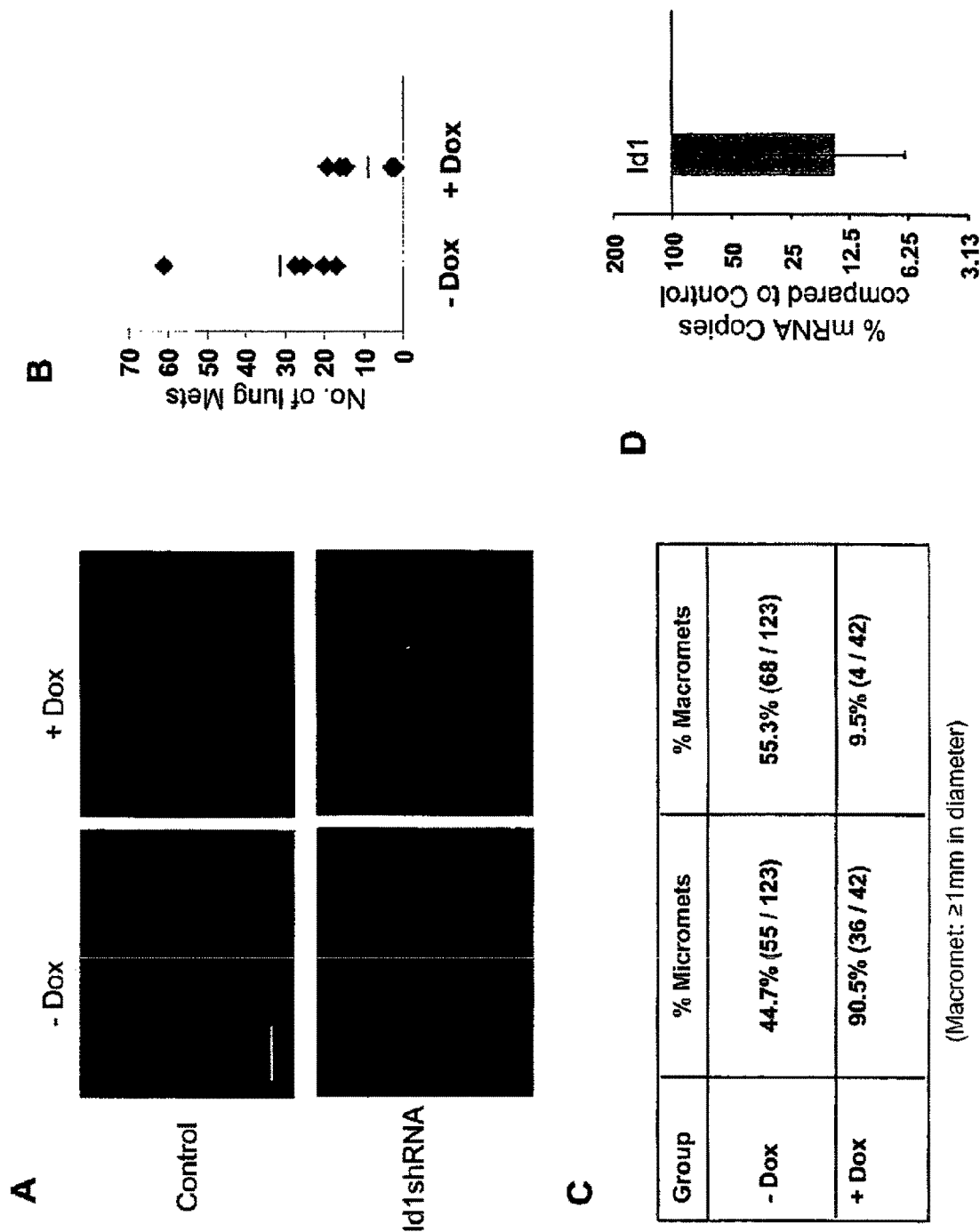
FIGS. 22A-D show that doxycycline induced shRNA suppression of Id1 in the BM progenitors reduced metastases progression in the lung.
Figure 23:
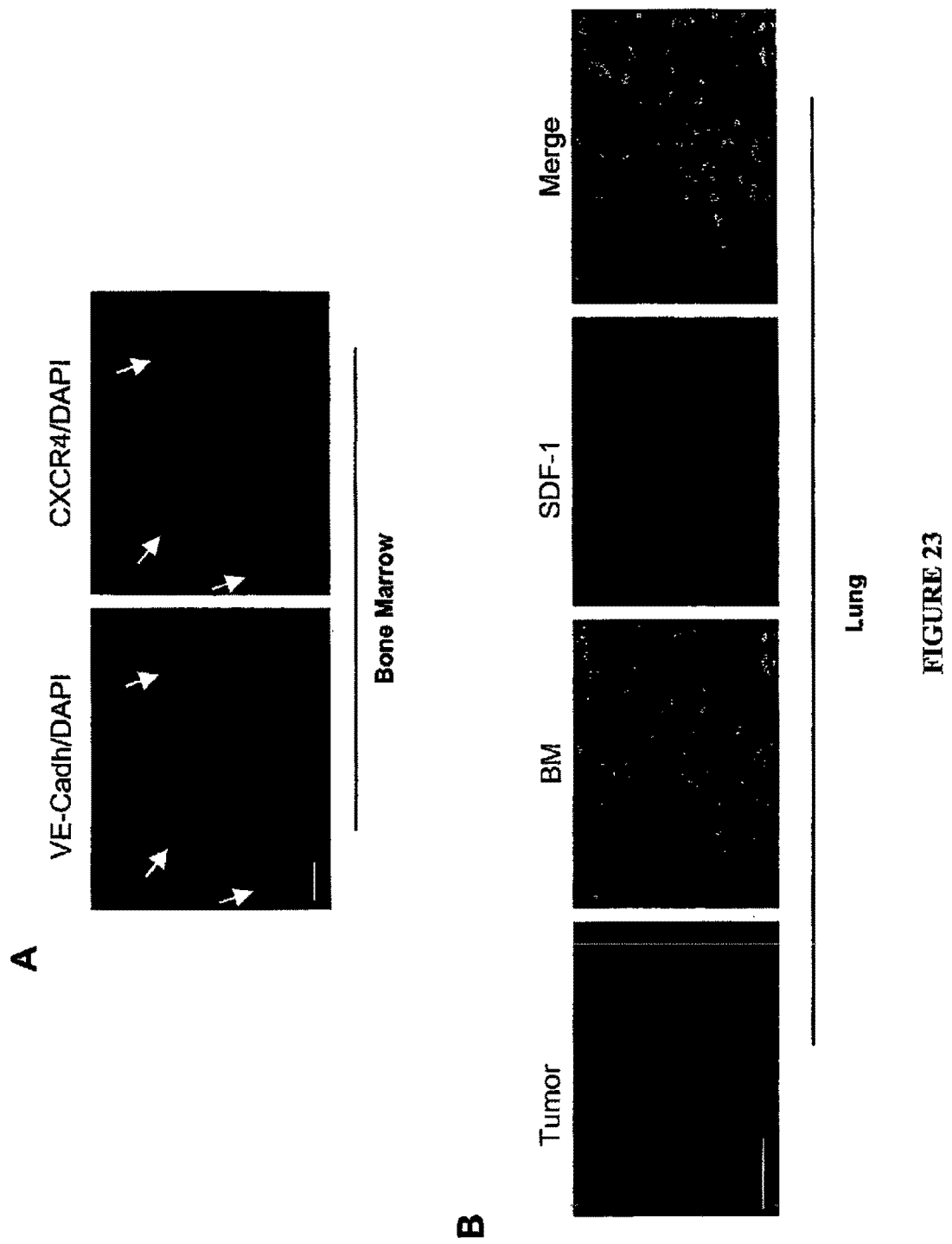
FIGS. 23A and B show that a CXCR4-SDF axis is involved in the recruitment of BM-derived EPCs to the sites of metastases.
FIG. 23B is a representative fluorescent image showing SDF1 gradients in LLC metastases in the lungs (day 14). Tumor cells (RFP) and BM-derived cells (GFP) in lung metastatic lesions. Scale bar, 100 μM. DAPI was used to stain all nuclei.

In this example, we demonstrated that an angiogenic switch was associated with the progression of micrometastases to macrometastases. Our analysis showed that BM-derived EPCs contributed to neovessel formation during metastases progression. EPCs were recruited to sites of active neovascularization via the SDF1-CXCR4 and VLA-VCAM interactions (FIG. 23). RNAi-mediated silencing of Id1 transcription factor in the BM progenitors (FIG. 21) did not affect initial colonization of lungs by malignant primary tumor cells, but markedly impaired metastases progression (FIGS. 22 A and B) as a consequence of decreased neovascularization.

A. An Angiogenic Switch is Associated with the Progression of Micrometastases to Macrometastasis.

To understand the role of BM-derived EPCs in metastasis progression, we developed a system for tracking both the BM-derived cells and tumor cells in vivo, so that these cells could be localized at the sites of metastases in the secondary organs. Lewis lung carcinoma (LLC) cells stably expressing monomeric red fluorescent protein (RFP, cherry version) were generated. Compared with traditionally used DsRed2 protein, mRFP-cherry is brighter, less photobleachable, more stable, and less toxic (Shaner et al., *Nat Methods* 2, 905 (2005)). These features allowed the tracking of disseminated tumor cells from primary tumors to metastatic sites and allowed direct detection of metastatic lesions both in the entire organs, and in histological sections.

Figure 17:
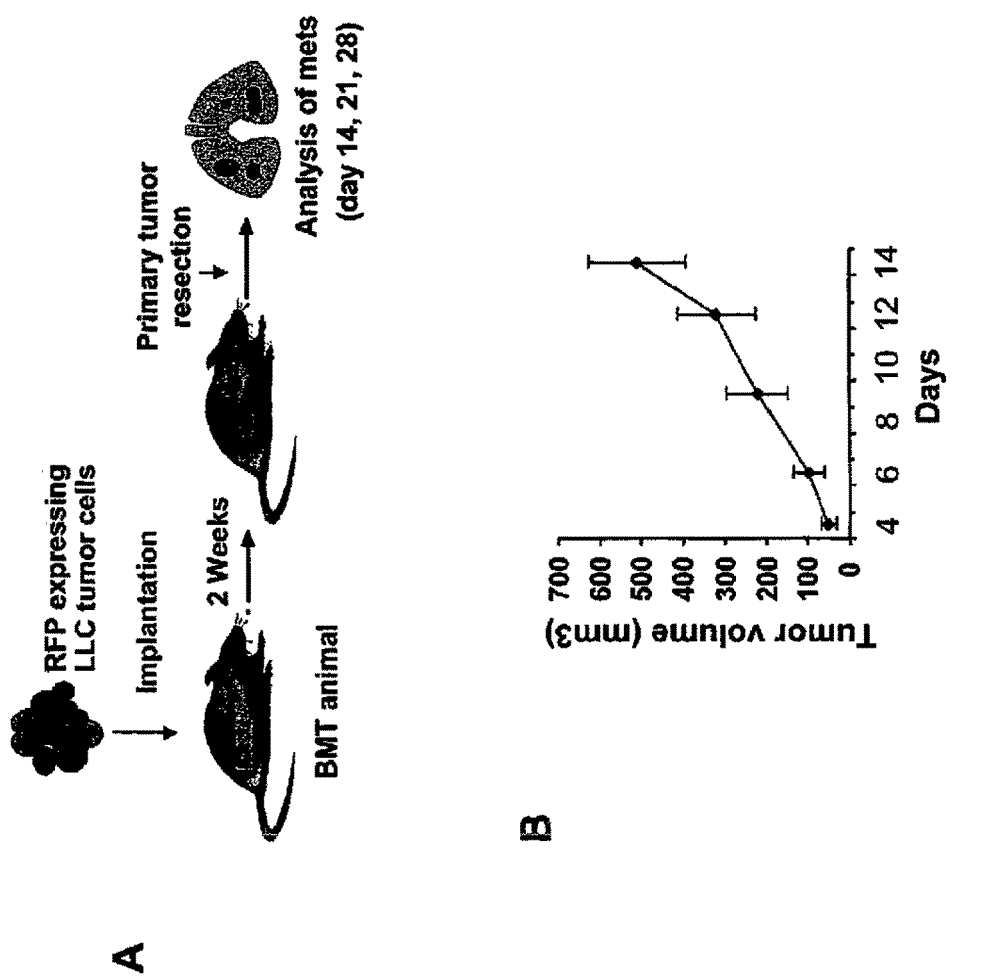
FIGS. 17A and B show a lung metastasis model.
FIG. 17B shows that tumors derived from 5×10^6 LLC cells stably expressing RFP were inoculated intradermally in the flank region of GFP+ BM reconstituted mice. Tumor size was measured every 2-3 days with a caliper. Tumor growth is represented as the mean±SD, n=20. SD, Standard deviation.
Figure 18:
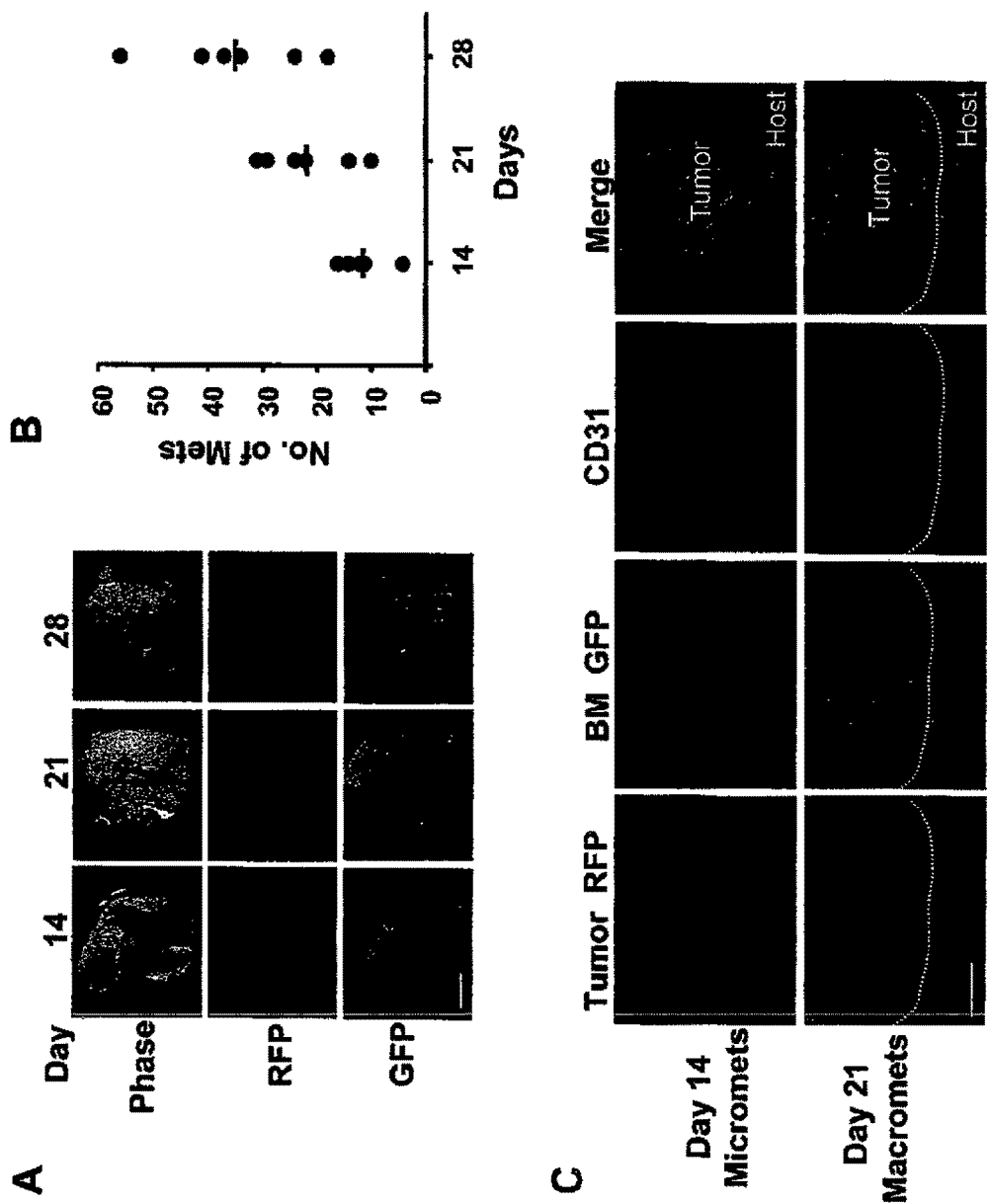
FIGS. 18A-C show that progression of micrometastases to macrometastases is associated with an angiogenic switch.

To determine the contribution of BM-derived EPCs to the formation of neovasculature in the metastatic colonies, GFP$^+$ BM cells were transplanted into lethally irradiated age matched, syngeneic, non-GFP recipients by tail vein injections as described previously. Next, these GFP$^+$ BM reconstituted mice were intradermally implanted with RFP expressing LLCs ($1\times10^6$ cells), which metastasized to the lungs (FIG. 17A). The primary tumors were allowed to grow for two weeks (average volume 500 mm$^3$), and then resected to control morbidity associated with excessive primary tumor burden which would have otherwise occurred later (FIG. 17B). Animals were sacrificed at day 14, 21, 28 and their lungs were examined for pulmonary metastasis using a fluorescent stereomicroscope. In early lungs (day 14), numerous RFP$^+$ small metastases (12 on average per animal) were observed. All of them were micrometastases (100%, <1 mm in diameter). The total number of metastases increased with time (22 and 35 on average per naimal, at day 21 and day 28, respectively), with a concomitant increase in the percentage of macrometastases 1 mm in diameter, 47% at day 28) (FIGS. 18A and B). This indicated a time window of micro- to macro-metastasis progression. Noticeably, in most metastases, GFP$^+$ BM-derived cells were observed to colocalize with the tumor cells (FIG. 18A), suggesting that these cells may have played important roles in the progression of these lesions. Micrometastases were not observed in the lungs during early phases of primary tumor growth, suggesting that the metastasis had resulted from the dissemination of the malignant primary tumors. Histological analysis showed that early micrometastases (<1 mm in diameter) were avascular as determined by the absence of CD31$^+$ vessels in the tumor bed (FIG. 18C, top). However, at this stage many BM-derived GFP$^+$ cells were observed to be infiltrating the tumor bed. Analysis of macrometastases (>1 mm in diameter) showed the recruitment of CD31$^+$ neovessels of various sizes (FIG. 17C, bottom), indicating that these colonies had undergone an angiogeneic switch.

Figure 19:
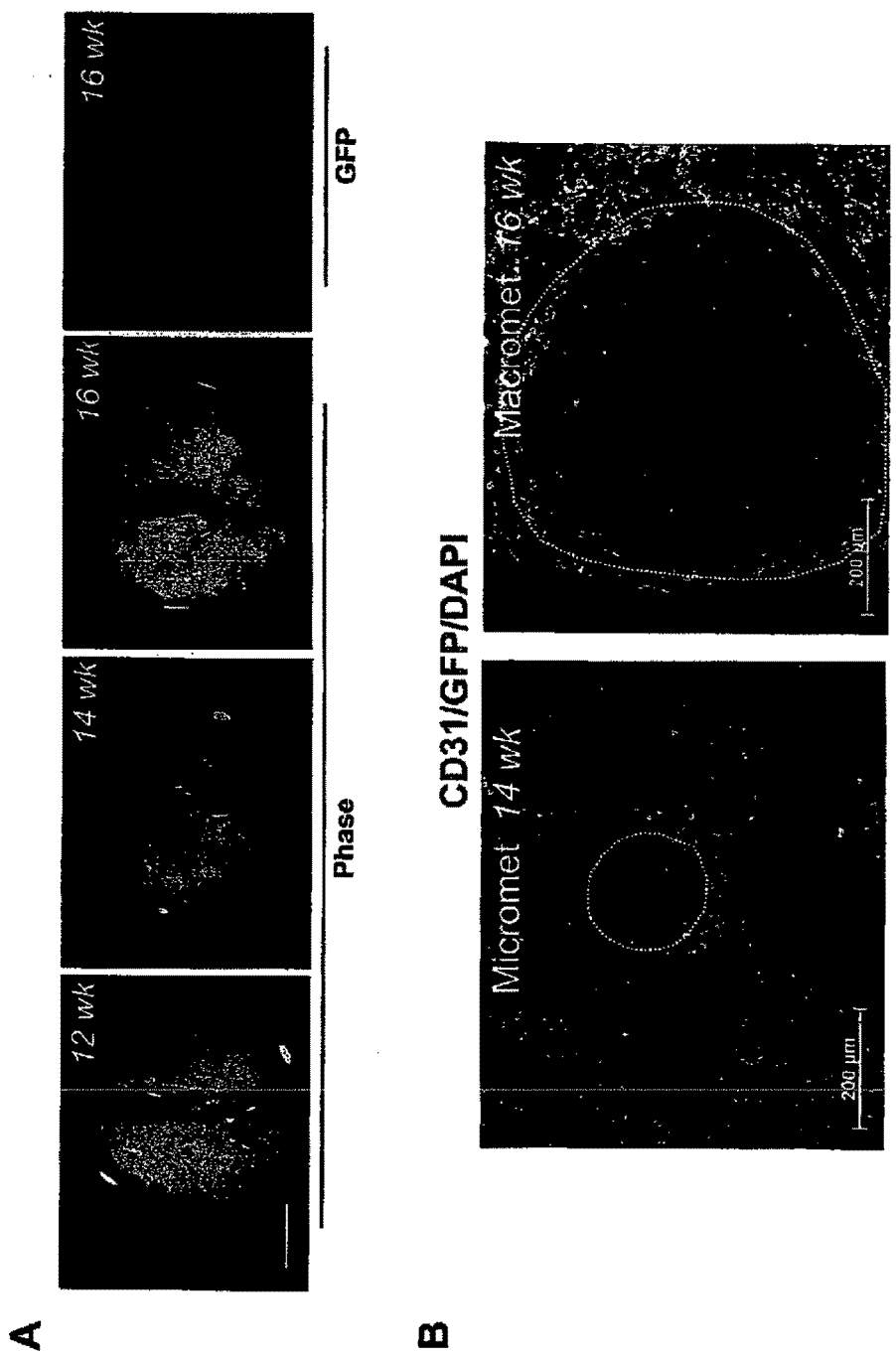
FIGS. 19A and B show the progression of micrometastases to macrometastases in a mouse model of spontaneous breast tumors developing in MMTV-PyMT trangenic mice.
FIG. 19B is a representative fluorescent image showing an avascular metastatic lesion (week 14), and a vascularized macrometastases (week 16). Blood vessels were detected by anti-CD31 antibody. Scale bar, 200 μM. The dotted line separates the host tissue from the tumor. Scale bar, 200 μM.

In order to confirm that these events were also taking place in metastases developing in a spontaneous metastatic tumor model, we performed a similar analysis of lung metastases arising in MMTV-PyMT breast cancer transgenic mice. In these mice, pulmonary micrometastases were detected at 12 weeks of age, which progressed into numerous macrometastases by week 16 (Guy et al., *Mol Cell Biol* 12, 954 (1992)). We transplanted the mice with syngeneic GFP$^+$ BM. Animals were sacrificed (Lyden et al., *Nat Med* 7, 1194 (2001); Ruzinova et al., *Cancer Cell* 4, 277 (2003); Shaked et al., *Science* 313, 1785 (2006); Grunewald et al., *Cell* 124, 175 (2006); Jin et al., *J Clin Invest* 116, 652 (2006)) and their lungs were examined for pulmonary metastasis. By 12 weeks we observed the appearance of micrometastases (average 2-5 per animal, <0.5 mm in diameter), which rapidly increased in numbers by week 14, and progressed to numerous macrometastases by week 16 (>1 mm in diameter, FIG. 19A). Noticeably, in most metastases GFP$^+$ BM-derived cells were observed to colocalize with the tumor cells (FIG. 19A). Histology showed that micrometastases were avascular and lacked CD31$^+$ vessels (FIG. 19B, left), whereas macrometastases were invaded with CD31$^+$ neovessels of various sizes (FIG. 19B, right), indicating that these colonies had undergone an angiogeneic switch. Further quantification showed that 11.7±3.6% of vessels in the metastases contained incorporated GFP$^+$ BM-derived endothelial cells. Collectively, these results suggest that an angiogenic switch is associated with the progression of micrometastases to macrometastases and that the BM-derived EPCs are recruited to the active sites of neovascularization and contributes to neovessel formation.

Figure 20:
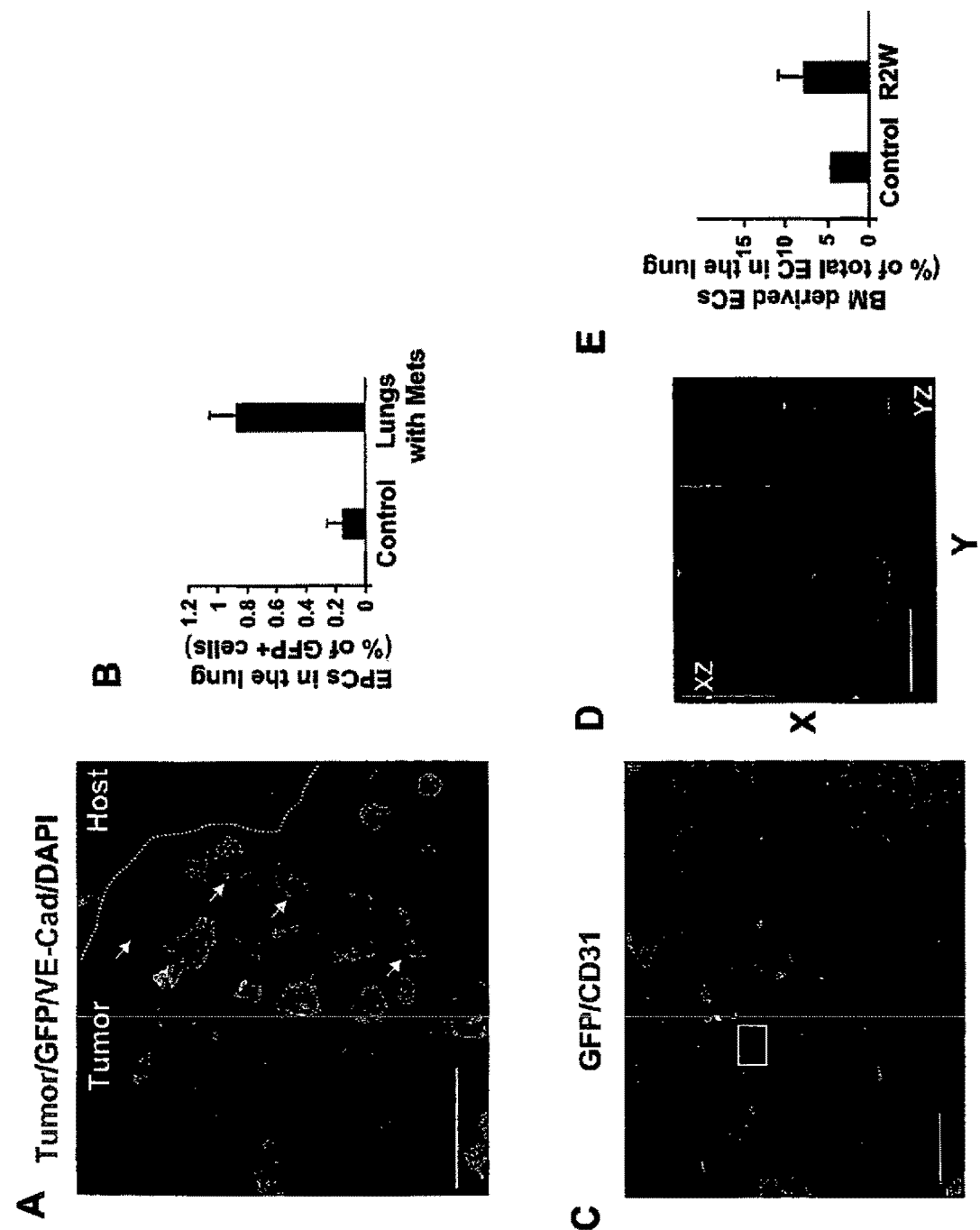
FIGS. 20A-E show that BM-derived EPCs contribute to neovasculature formation during the growth of micrometastases to macrometastases.

B. BM-Derived EPCs Contribute to Neovasculature Formation During Macrometastases Formation We next determined the contribution of BM-derived EPCs in neovessel formation in growing metastatic lesions. Lungs bearing metastatic lesions were isolated, cryosectioned, and immunostained for EPC markers (VE-cadherin, VEGFR2, CD31$^{low}$) described above. Micrometastases showed a marked recruitment of GFP$^+$ BM-derived EPCs as judged by the expression of GFP and VE-cadherin at the periphery of the tumor margins (FIG. 20A). Noticeably, EPCs were observed in these micrometastases prior to vessel recruitment from the peripheral host vasculature (FIG. 20A). We next quantified the contribution of BM-derived EPC in these micrometastases by flow cytometric analysis. The analysis showed that lungs bearing micrometastases had a five-fold increase in BM-derived EPCs (GFP$^+$ VE-cadherin$^+$ CD31$^{low}$ CD11b$^-$) as compared to that of control normal lungs (198.5±29.9 vs. 37.3±6.1, p<0.0001). BM-derived EPCs comprised of 1% of total GFP$^+$ cells in these micrometastases as compared to lungs devoid of metastases (FIG. 20B). Analysis of early vascular macrometastases (3 weeks post primary tumors) showed the recruitment of CD31$^+$ neovessels of various sizes with incorporated BM-derived GFP$^+$ CD31$^+$ECs (FIG. 20C). Optical sectioning (Z-stack resolution of 0.275 µM) further confirmed that the BM-derived ECs had a single nucleus, and that the GFP and CD31 signals were localized to the same individual cell in all serial confocal planes (FIG. 20D).

We also quantified luminally incorporated BM-derived ECs in tumor vessels by perfoming systemic perfusion with fluorescently labeled isolectin GS-IB$_4$ that specifically stains the ECs in functional blood vessels. Macrometastases were microdissected from the lungs and analyzed by flow cytometry. The luminally incorporated BM-derived endothelial cells (GFP$^+$ Lectin$^+$ CD31$^+$ CD11b$^-$) represented on average 12.7±2.9% of total endothelial cells (Lectin$^+$ CD31$^+$ CD11b$^-$) in the macrometastases. Of the total functional vasculature (Lectin$^+$ CD31$^+$ CD11b$^-$), approximately 10% ECs were BM-derived (GFP$^+$Lectin$^+$ CD31$^+$ CD11b$^-$) (FIG. 20E). Together, these results demonstrate that BM-derived ECs contribute to neovessel formation during progression of avascular micrometastases to vascular metastases.

C. EPC Mobilization Defects Impair Progression of Micrometastases to Macrometastases To explore the biological function of the BM-derived EPCs in mediating the progression of micrometastasis to macrometastasis, we set up an experimental metastasis model in Id1 knockout mice. Id1 knockout mice had been shown to exhibit impaired tumor growth and BM-associated angiogenesis defects (Lyden et al., supra; Ruzinova et al., supra). Injection of tumor cells via the tail vein resulted in pulmonary micrometastases formation in both Id1 knockout and wild type mice. In contrast, macrometastases formation was significantly impaired in Id1 knockout mice as compared to wild type littermates. Metastatic lesions in Id1 knockout mice were associated with significantly reduced vessel density as compared to wild type animals, suggesting that angiogenesis inhibition was the major cause for the failure of metastasis progression. Flow cytometric analysis revealed significant defects in the recruitment of EPCs (c-kit$^+$ VEGFR2$^+$ CD45$^-$, P=0.0041), but not hematopoietic lineages including leukocytes, macrophages or hematopoietic progenitor cells (HPC) in the lungs and peripheral blood in Id1 knock out mice. Taken together, these results suggest that EPC mobilization defects in Id1 knockout animals caused impaired progression of micrometastases to macrometastases.

D. Specific Ablation of BM-Derived EPCs by shRNA-Mediated Suppression of Id1 Transcription Factor Reduces Macrometastases Formation.

To explore the mechanisms by which Id1 deficiency leads to a failure in metastatic progression, we first examined Id1 expression in the BM cells. In response to a tumor challenge, Id1 mRNA expression was upregulated by about 2.5 folds. Most notably, Id1 protein expression was confined to EPCs and not to other BM cells, suggesting that Id1 may be critical for EPC function in angiogenesis-mediated progression of lung metastasis. To dissect the role of Id1 in EPC-mediated progression of metastatic lesions in spontaneous metastasis model, we employed a lentiviral-based tetracycline inducible miR-30-based short hairpin RNA (shRNA) expression system to target Id1 expression in vivo (Stegmeier et al., *Proc Natl Acad Sci USA* 102:13212-7 (2005)). This approach allowed us to generate acute Id1 suppression in the BM precisely following metastatic colonization in the lungs, thereby ensuring that the contribution of BM-derived endothelial cells to the growth of primary tumor was not compromised.

Figure 25:
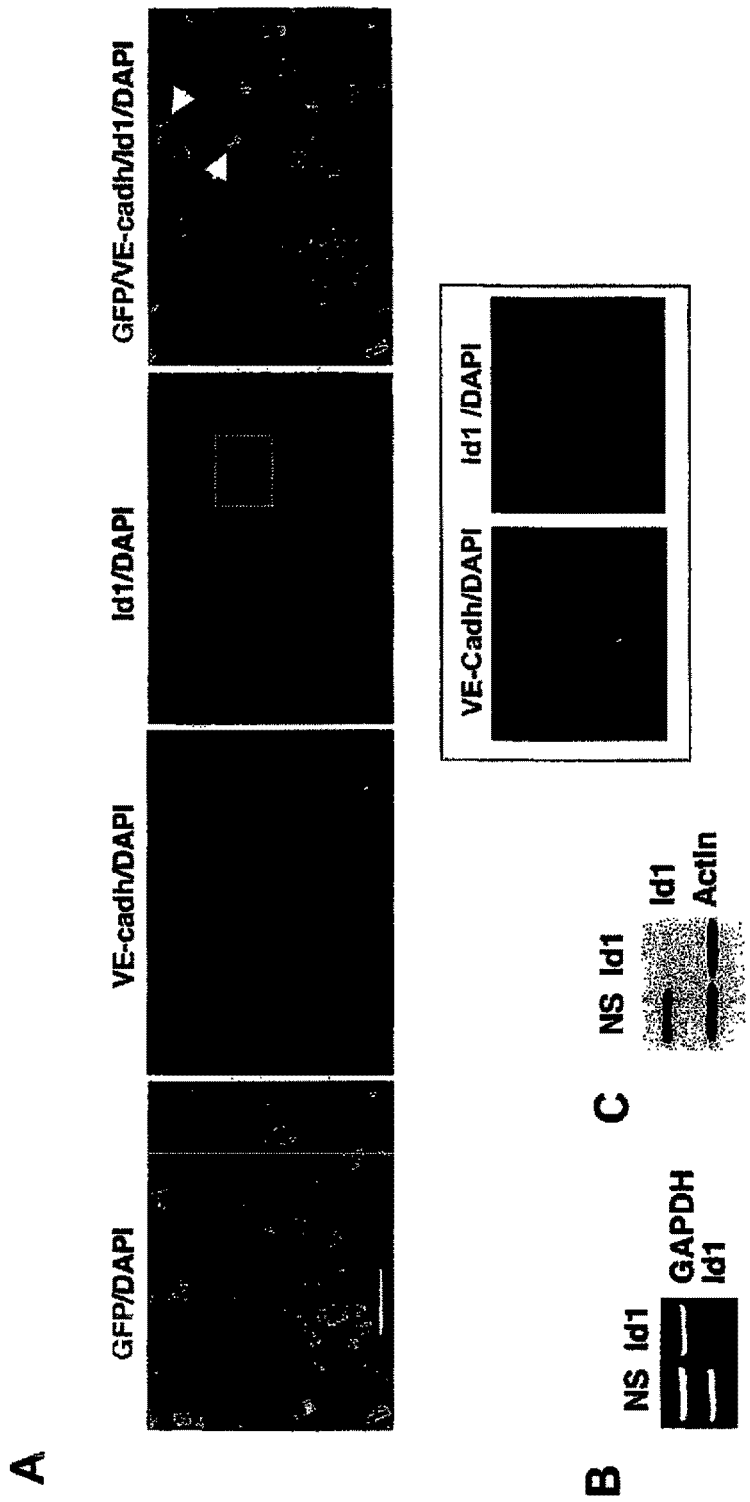
FIGS. 25A-C shows that Id1 is expressed in immature endothelial cells.

More specifically, we identified shRNAs that reduced endogenous Id1 mRNA and protein levels in cell culture (>95% reduction) as determined by both real time-polymerase chain reaction (RT-PCR) and Western blotting (FIGS. 25B and C). Lentiviral vectors expressing a non-specific shRNA, Id1-specific shRNA and a GFP transgene reporter were generated to transduce BM progenitor cells. To ensure that the EPC contribution to the primary tumors was not compromised in these experiments a doxycycline (dox) inducible shRNA expression system was used (FIG. 21A), which showed tight regulation in vitro as determined by GFP expression and Id1 suppression (FIGS. 21B and C). BM-derived Lin⁻ progenitor cells harvested from Rosa26-rtta transgenic animals were transduced ex vivo with lentivirus expressing either the Id1-specific shRNA or a non-specific shRNA (FIG. 21D). In order to maximize the pluoripotency of the BM precursor cells all transductions were performed ex vivo for 12-18 h on freshly isolated cells in the absence of serum or cytokines followed by transplantation into recipient mice. Following BM reconstitution, LLC cells were implanted in the shRNA bone-marrow-transplanted (BMT) mice, allowed to grow for 2 weeks and resected. Following tumor resection shRNA expression was induced by dox administration (0.2 or 2 mg/ml in drinking water). Metastases were analyzed in the lungs to determine the impact of the suppression of Id1 gene expression. There was a pronounced reduction of macrometastases formation in dox treated Id1 shRNA-BMT mice compared with that of control non-specific shRNA-BMT (FIGS. 22A-C). Notably, micrometastases were observed in the lungs of dox treated Id1-shRNA BMT animals (FIG. 22A, bottom right panel, FIG. 22C) suggesting that Id1 suppression did not prevent initial lung colonization by malignant primary LLC tumor cells but impaired their progression into vascularized macrometastases. Stable and inducible suppression of Id1 mRNA in vivo was confirmed in the BM of dox treated mice by quantitative RT-PCR (FIG. 22D).

Collectively, these results suggest that shRNA-mediated suppression of Id1 results in impaired EPC-mediated progression of micrometastases to macrometastases. Thus, targeting EPCs is a clinically appropriate therapeutic approach to blocking the growth of metastatic lesions.

E. The SDF-1 and VCAM-1 Gradients Mediate the Recruitment of EPCs to the Metastatic Lesions We next investigated the mechanisms governing the recruitment of BM-derived EPCs to sites of active neovascularization in progressing metastases. We examined the role of the SDF1-CXCR4 axis and the VLA-VCAM interactions. These interactions have been previously demonstrated to promote the homing of hematopoietic progenitor cells and other circulating mononuclear cells to the vascular endothelium during neovascularization. (Grunewald et al., 2006; Jin et al., 2006).

Figure 24:
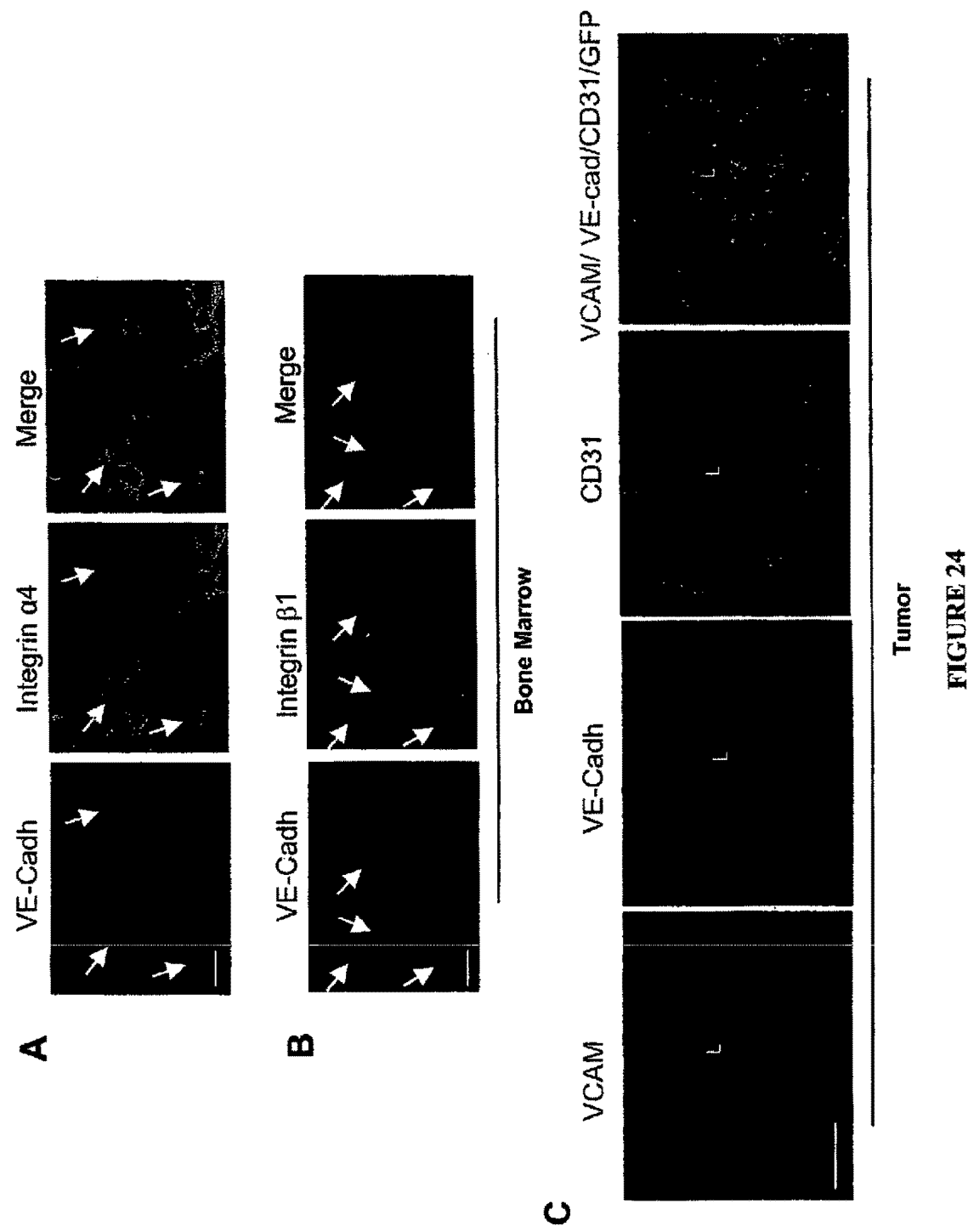
FIGS. 24A-C show that a VLA-VCAM axis is involved in the recruitment of BM-derived EPCs to the neovessels at the sites of metastases.

EPCs expressed CXCR4 as determined by immunostaining of VE-cadherin⁺ BM-derived cells (FIG. 23A). Notably, in the metastatic lesions EPCs were observed to be concentrated around the SDF-1 gradients (FIG. 23B). EPCs also expressed significant levels of integrins $\alpha 4\beta 1$ (FIG. 24A). We examined metastases undergoing neovascularization for expression of the $\alpha 4\beta 1$ ligands VCAM. VCAM was expressed in CD31⁺ nascent vessels (FIG. 24B). Notably, EPCs were present around these VCAM+ vessels (FIG. 24B).

Together, these results suggest that CXCR4⁺ EPCs are recruited to SDF1 gradients available at the sites of metastases, and that $\alpha 4\beta 1$-VCAM interaction promote adhesion of $\alpha 4\beta 1^+$ EPCs to the VCAM⁺ neovessels.

EXAMPLE 3

Figure 26:
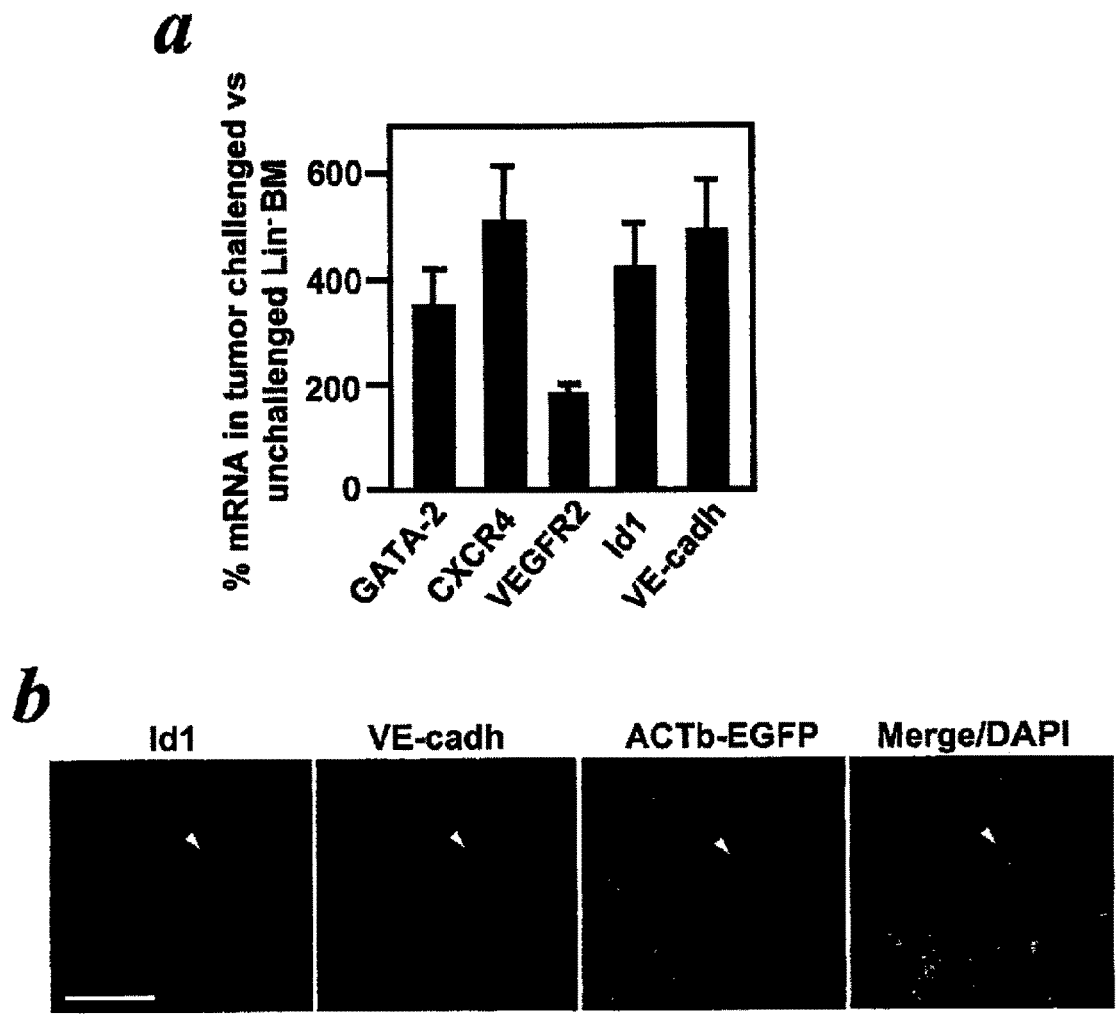
FIG. 26 B is a representative immunoflurescent microscopy image of an early tumor from ACTb-EGFP BMT mice (day 6, LLC), showing recruitment of BM-derived ACTb-EGFP$^+$ Id1$^+$ VE-cadherin$^+$ cells (arrow). Scale bar=20 μM. DAPI was used to stain the nuclei of all cells.

Our previous demonstration that EPCs dictate angiogenesis-mediated tumor growth establishes a powerful paradigm in cancer biology. Since EPCs comprise of a minor population of the BM compartment (1 in 10,000 BM cells is an EPC), it is critical to specifically mark these cells in vivo. To determine novel EPC specific genes, we compared gene expression profiles of tumor challenged BM-progenitors with tumor unchallenged BM progenitors. Of the 14 K genes examined, 500 of the transcripts, on average, were found to be differentially regulated by at least 1.5-fold. Quantitative RT-PCR further validated certain candidate genes such as helix-loop-helix transcription factor Id1, CXCR4, VE-cadherin, flk1/VEGFR2, and GATA2 (FIG. 26A). Using histological analysis and flow cytometry expression of Id1, VE-cadherin and VEGFR2/flk1 was localized to the BM-derived GFP⁺ EPCs (FIG. 26B).

Figure 27:
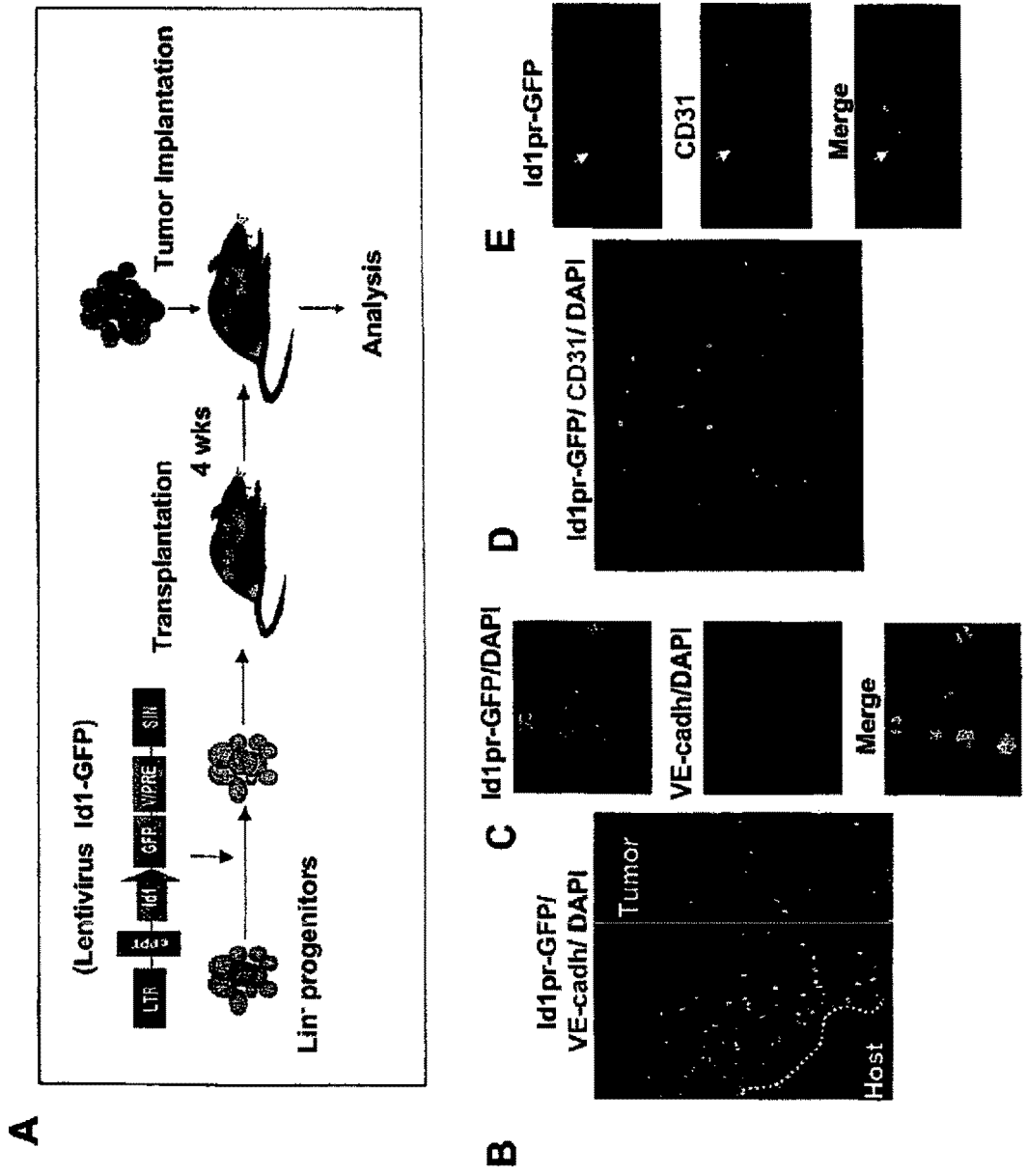
FIGS. 27A-E show that the Id1 promoter marks EPCs in vivo.
Figure 28:
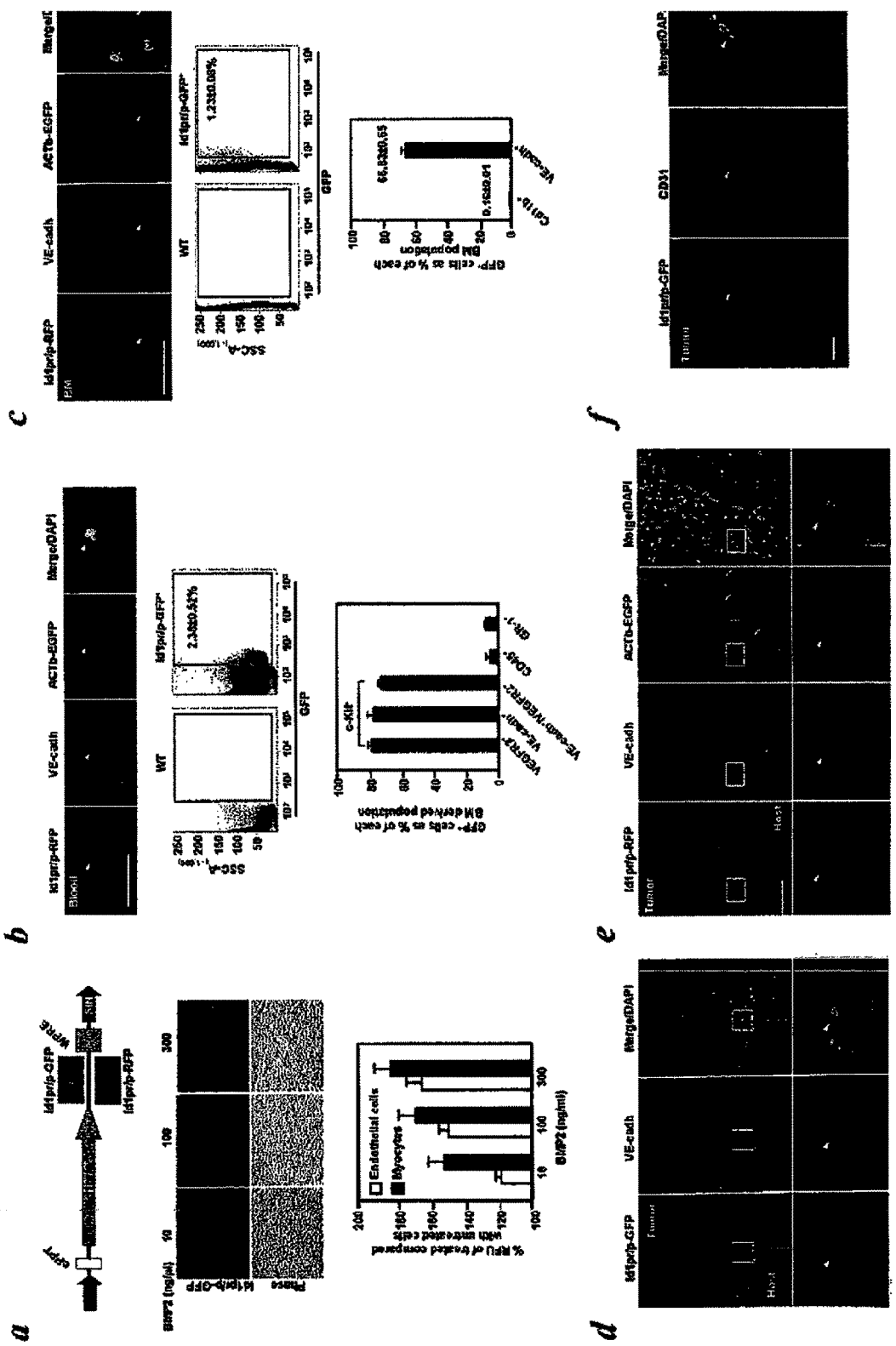
FIGS. 28A-F show that Id1pr/p (Id1 proximal promoter) marks EPCs in the blood, BM and tumor

We investigated promoters of these genes (Id1, VEGFR2 and VE-cadherin) for their ability of mark EPCs in vivo. We constructed a lentiviral vector that expresses GFP under the transcriptional control of the Id1 promoter (FIG. 27A). Of note, Lentiviruses are particularly useful as gene-delivery vectors because they incorporate randomly into the host genome in nondividing cells (such as BM-progenitor cells) and achieve successful long-term expression of the transgenes in vivo. We first tested whether the Id1 promoter regulated GFP activity in vitro by generating stable cell lines. Previous studies have shown that the bone morphogenic protein 2 (BMP2) induces Id1 promoter activity (Katagiri et al., *Genes Cells* 7, 949 (2002); Korchynskyi and P. ten Dijke, *J Biol Chem* 277, 4883 (2002)). Indeed, treatment of these stable cells with increasing dosage of BMP2 enhanced GFP expression (FIG. 28A).

Figure 33:
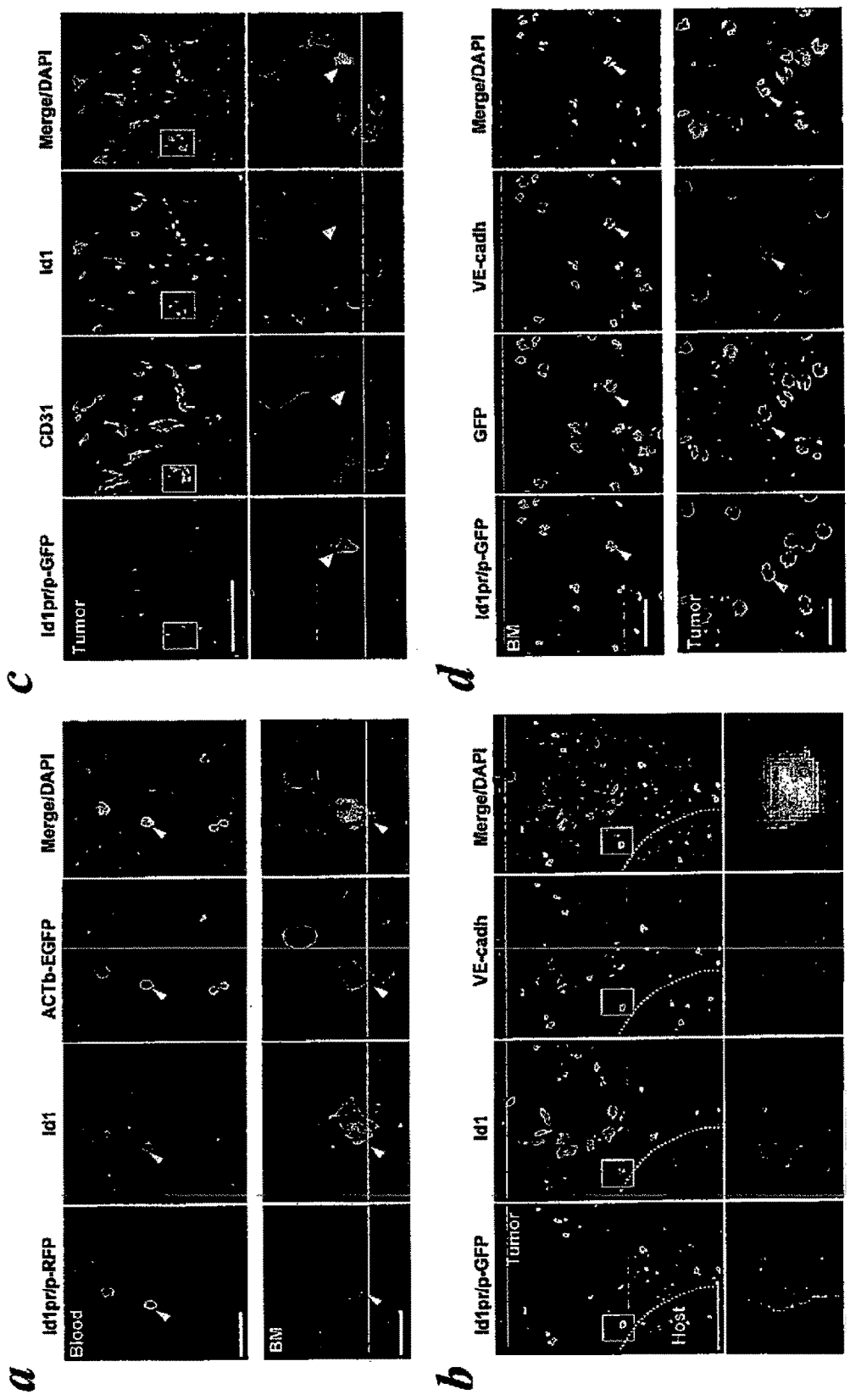
FIGS. 33A-D show that Id1 promoter targets gene expression to EPCs.
Figure 34:
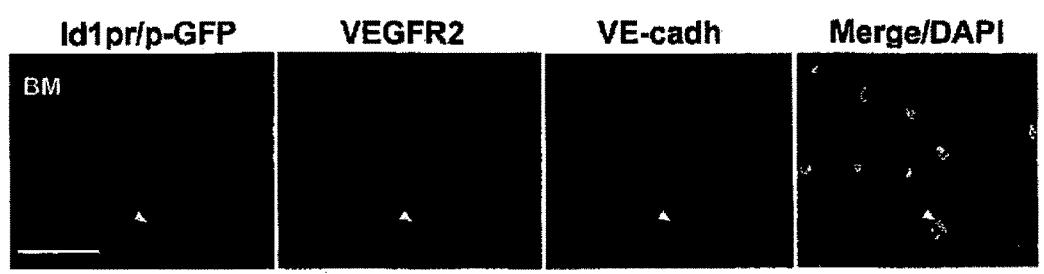
FIGS. 34A-C shows that Id1 promoter targets gene expression to EPCs. BM cells were transduced with viral vector encoding GFP driven by Id1 promoter. GFP expression was limited to the subset of BM cells that are EPCs.
Figure 34:
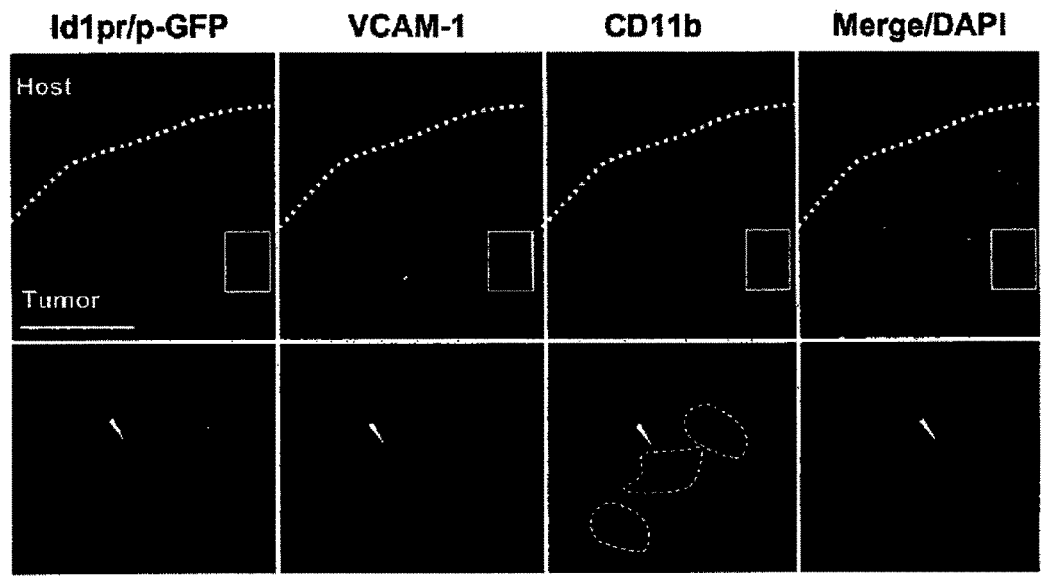
Figure 34:
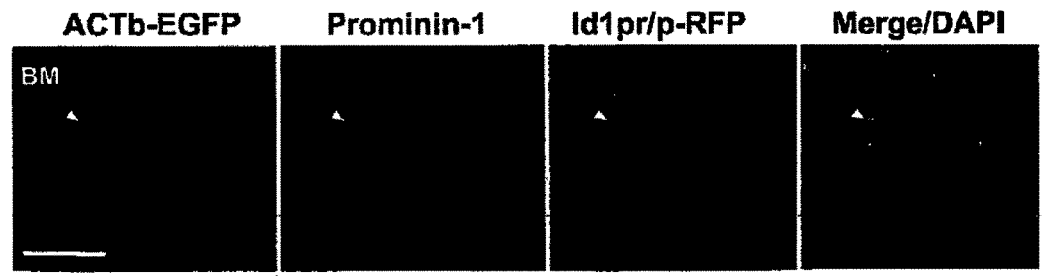

To stably deliver this construct into the BM progenitor cells, freshly isolated BM-derived Lineage negative (Lin⁻) progenitor cells from ACTb-EGFP⁺ mice were transduced ex vivo with lentiviral vector (FIG. 27A). In order to maximize the pluoripotency of the BM precursor cells, all transductions were performed for 12-18 h on freshly isolated cells in the absence of serum or cytokines, followed by transplantation into recipient mice. Animals were allowed to reconstitute for 4 weeks, and Lewis lung carcinoma (LLC) cells were implanted. Tumors were examined to determine the presence of GFP⁺ EPCs. Analysis of early tumors (day 4-6), showed a marked recruitment of donor BM-derived GFP⁺ cells at the periphery of the advancing tumor margins (FIG. 27B). Every GFP⁺ cells also expressed EPC markers including VE-cadherin (FIGS. 27C, 34A), VEGFR2/flk1 (FIG. 34) and Promini-nin-1 (FIG. 34C). We also performed experiments where a lentiviral vector encoding red fluorescent protein (RFP) under the Id1 promoter were used for transducing GFP⁺ BM harvested from β-actin-EGFP (ACTb-EGFP) transgenic mice (C57BL/6, Jackson Labs). In this case we observed that only the GFP⁺ RFP⁺ cells expressed Id1 protein (FIG. 33A) or VE-Cadherin protein (FIG. 28B). Id1-GFP⁺ EPCs also differentiated into mature endothelial cells and luminally incorporated into mature blood vessels (FIG. 28F). Together, these results demonstrate that the Id1 promoter specifically marks EPCs that contribute to neovessel formation during tumor angiogenesis.

Figure 29:
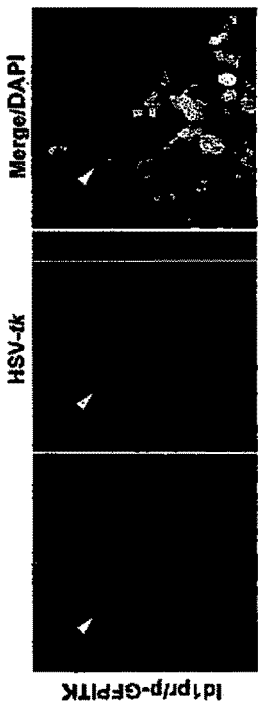
FIGS. 29A-D show that the Id1 promoter directs expression of Thymidine kinase (TK) and that administration of ganciclovir kills TK positive cells.
Figure 29:
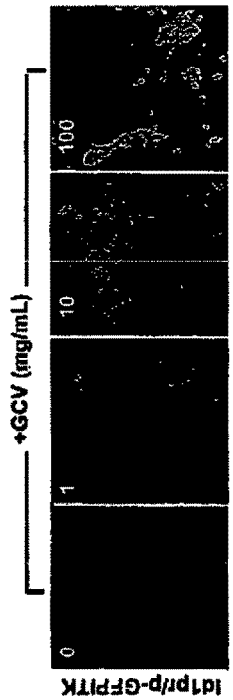
Figure 29:
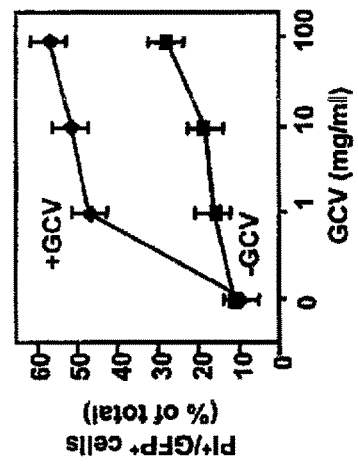
Figure 29:
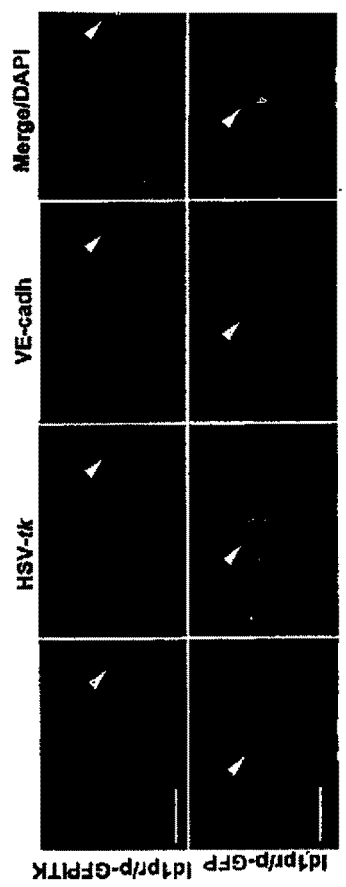
Figure 29:
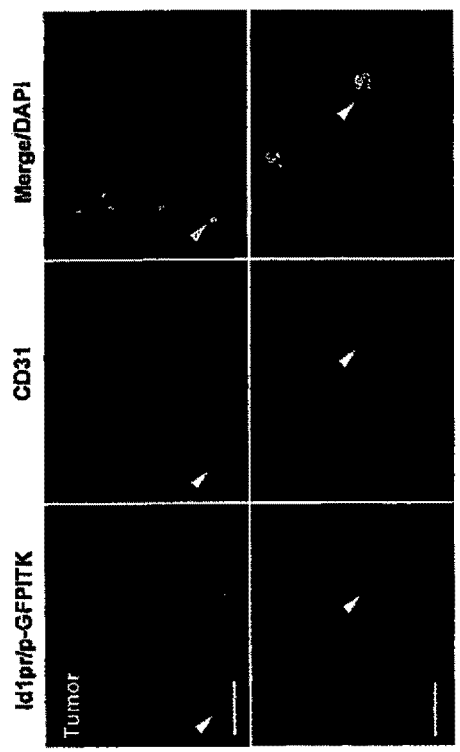

We next investigated whether the exquisite property of the Id1 promoter to mark EPCs can be exploited for cell specific ablation or generating loss of EPC function. The Id1 promoter was used to deliver a suicide gene HSV-tk. We confirmed that stable cell lines expressing GFP also expressed TK protein (FIG. 29A). Treatment with prodrug ganciclovir (GCV) ablated these GFP⁺ cells in a dose-dependent manner (FIG. 29B).

Figure 30:
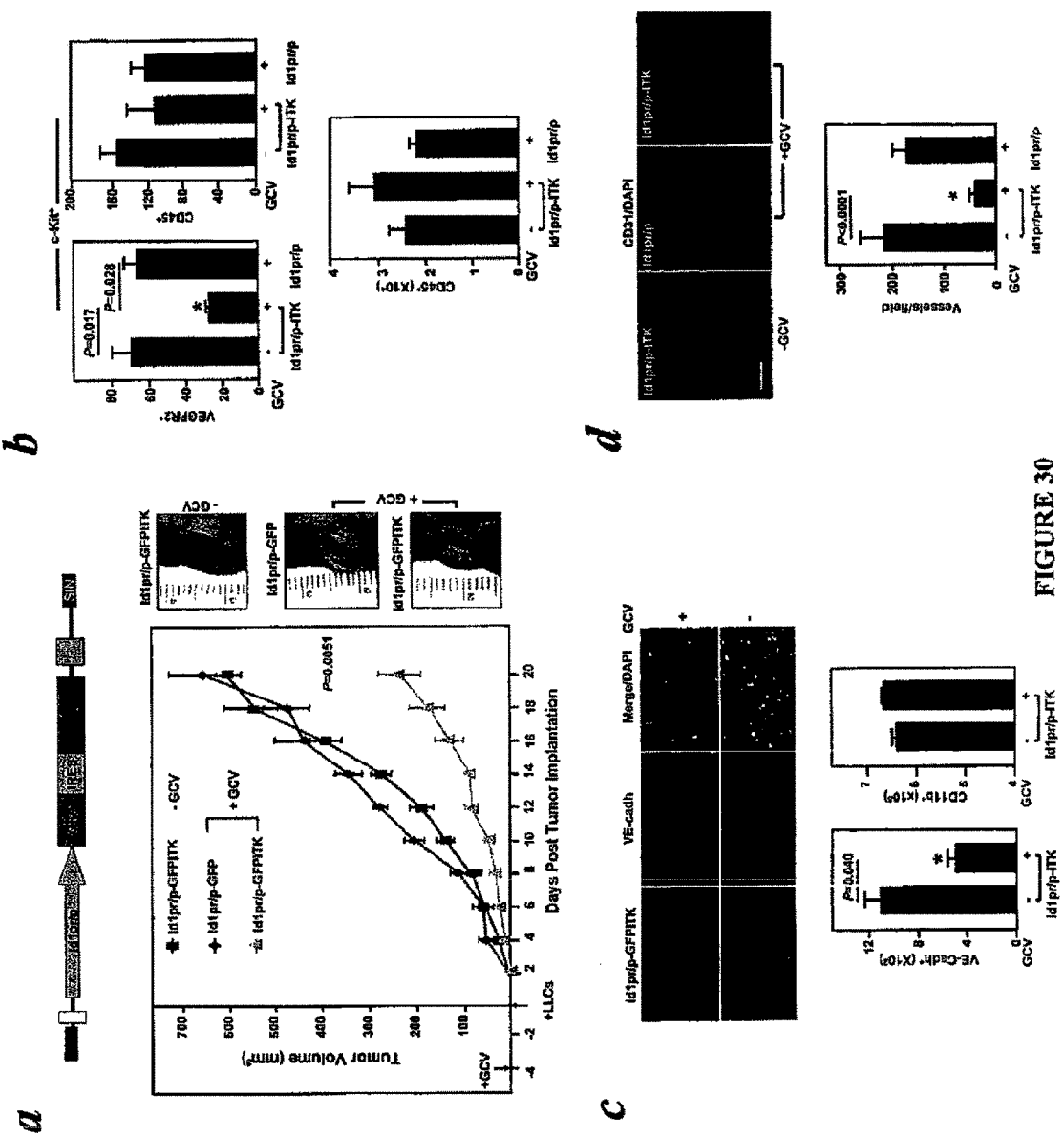
FIGS. 30A-D show that selective elimination of Id1pr/p-TK+ EPCs by delivery of a suicide gene HSV-tk impairs tumor growth in vivo.

Next, we investigated the delivery of TK in EPCs in vivo. BM-derived Lin⁻ progenitor cells were transduced ex vivo with a lentiviral vector encoding GFP alone or GFP-IRES-TK under the transcriptional control of the Id1 promoter and transplanted into irragiated WT recipients. We found that expression of TK (and GFP) was restricted predominantly to VE-cadherin$^+$ EPCs (FIG. 29C). Following transplantation into recipient mice, LLC cells were implanted and their growth measured for 2 weeks to determine the impact of delivering TK. Administration of GCV showed a delay in the appearance of tumors and slower tumor growth (>60% by day 20) in Id1 TK-BMT mice (+GCV) compared with Id1 TK-BMT (−GCV) or control Id1 GFP-BMT (+GCV) (FIG. 30A). The LLC tumors in −GCV mice were larger and appeared to be vascularized (red tumors), as compared to the relatively smaller pale tumors (−GCV). The tumors in GCV-treated TK-BMT mice showed a dramatic reduction in vascular density as compared to untreated mice (FIG. 30D), suggesting that vasculature defects in Id1 TK-BMT is the major cause for reduced tumor growth. FACS analysis of BM-derived peripheral blood (PB) cells showed that administration of GCV ablated VEGFR2$^+$ CEPs (circulating EPCs) specifically but did not affect normal hematopoiesis, since levels of CD45$^+$ c-Kit$^+$ hematopoietic progenitors and CD45$^+$ hematopoietic cells remained relatively unchanged (FIG. 30B). Analysis of BM showed a ~2-fold reduction in the level of EPCs (VE-cadherin$^+$) after the administration of GCV (FIG. 30C). These results show that delivery of suicide gene HSV-tk under the control of Id1 promoter is capable of inhibiting tumor angiogenesis as well as angiogenesis-mediated tumor growth.

Figure 31:
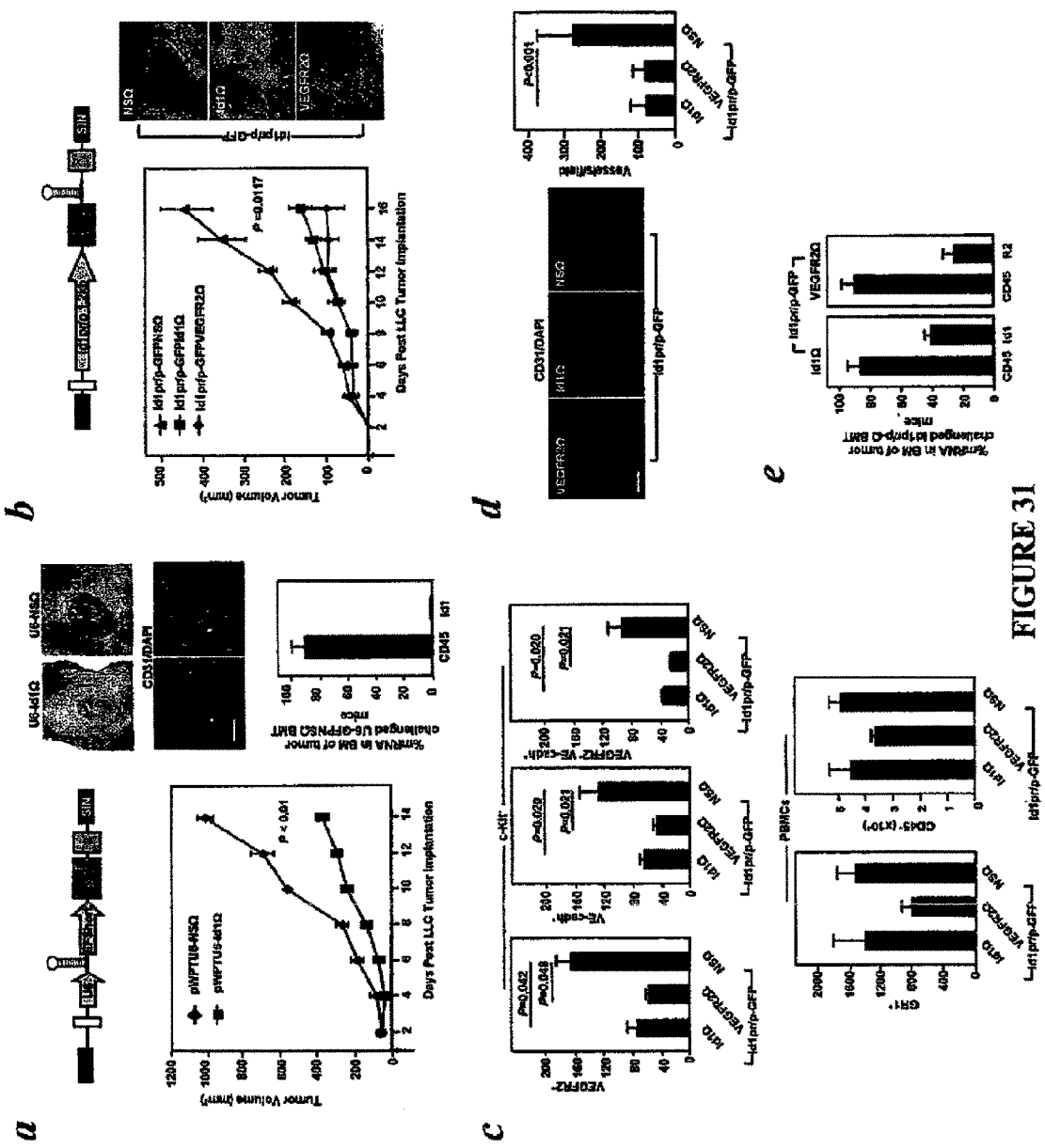
FIGS. 31A-E show that Id1pr/p shRNA-mediated suppression of VEGFR2 and Id1 in the EPCs results in angiogenesis inhibition and impaired tumor growth
Figure 32:
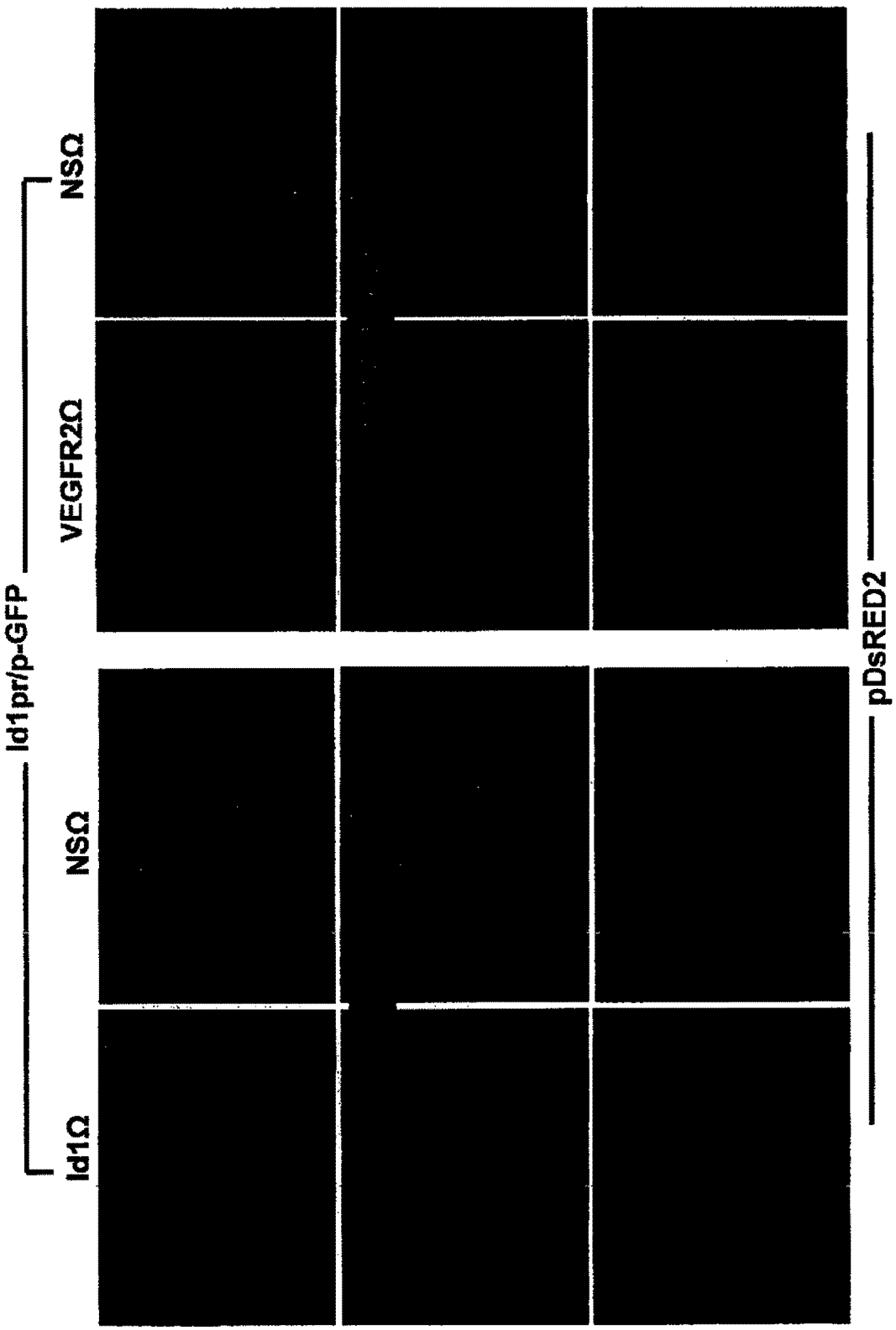
FIG. 32 shows that 293T cells stably transfected with Id1pr/p-GFPId1Ω and Id1pr/p-GFPVEGFR2Ω effectively silenced co-transfected Id1-CFP and VEGFR2-CFP fusion constructs respectively. pDsRed2-1 was used a transfection normalization control. Scale bar=100 μM.
Figure 35:
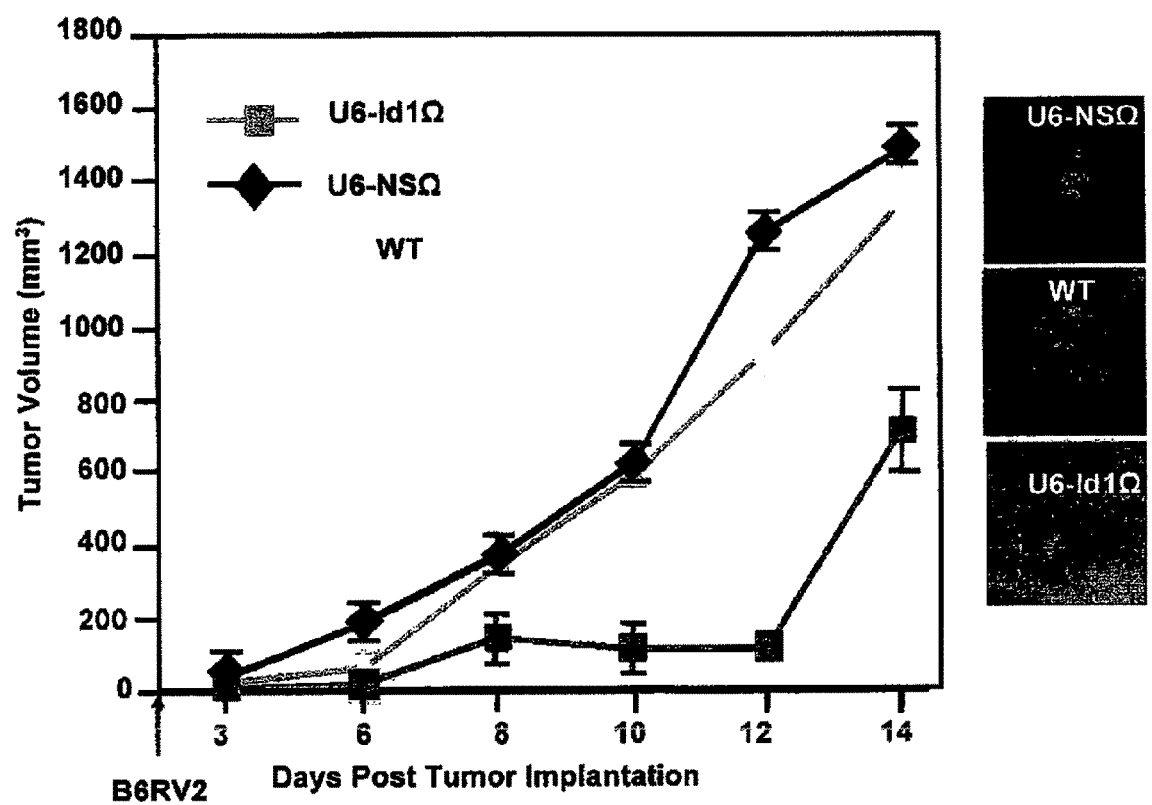
FIG. 35 shows B6RV2 tumor growth in pWPTU6-NSCΩ, pWPTU6-Id1Ω BMT and WT non-BMT mice (left, mean volume±S.E.M, P<0.001 by one-way ANOVA, n=5 per group). B6RV2 tumor morphology in pWPTU6-NSΩ or WT mice were larger and appeared to be more vascularized (red tumors), compared with the relatively smaller paler tumors observed in pWPTU6-Id1Ω mice.
Figure 36:
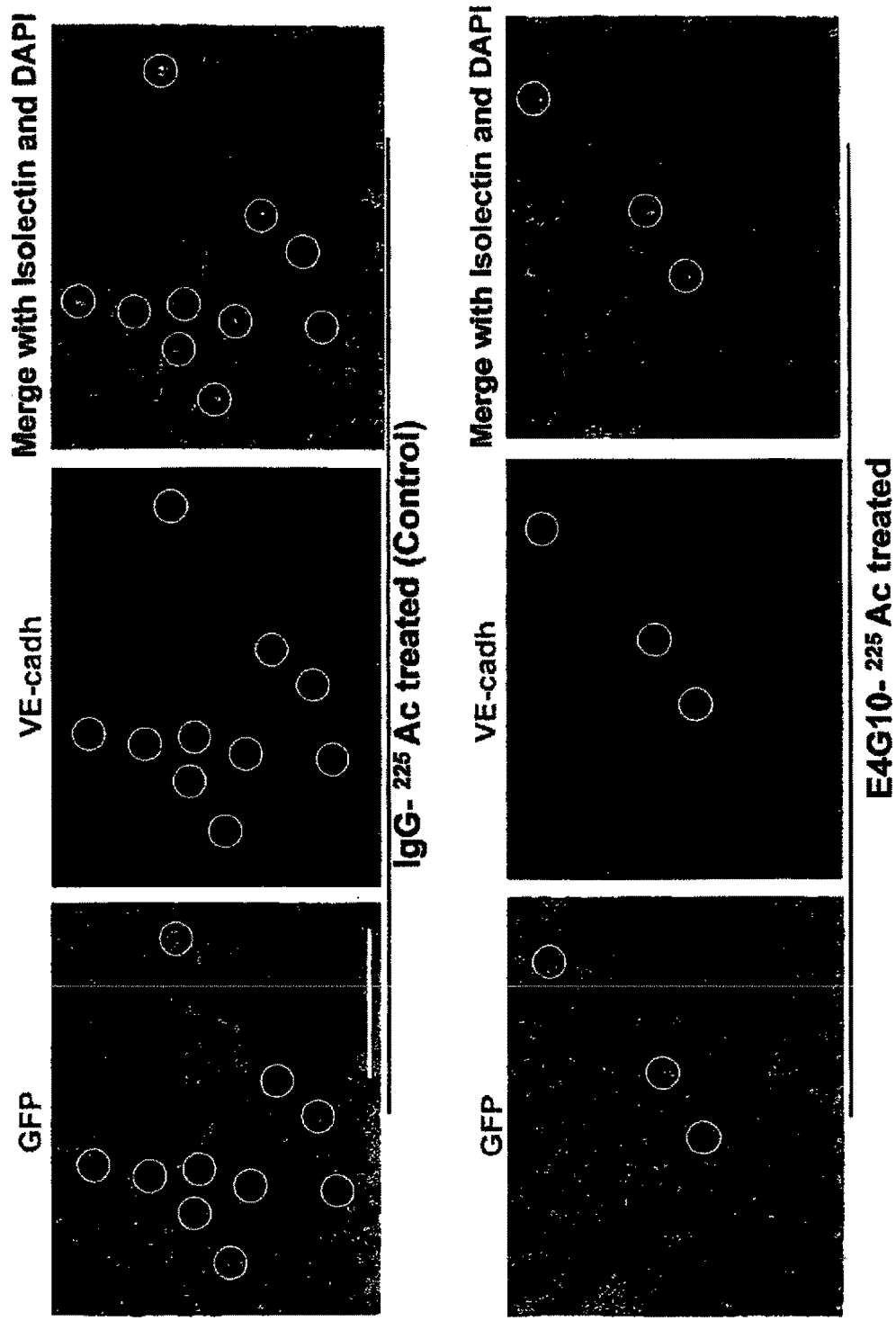
FIG. 36 shows the results of histological analysis of EPC ablation by anti-VE-cadherin antibody $^{225}$Act-4G10, with representative images of day 6 LLC tumors from animals administered with isotype control $^{225}$Act-IgG (top panels) or $^{225}$Act-E4G10 antibody (bottom panels). Yellow circles represent GFP+ VE-cadherin+ EPCs. The number of EPCs in tumors of E4G10-treated animals was reduced as compared to control animals. The contribution of total BM-derived GFP+ cells remained unchanged in both treatments. DAPI was used to stain the nucleus of all cells. Isolectin stained the blood vessels. Scale bar, 100 µm.

In another approach, we used RNA interference (RNAi) for suppressing Id1 gene expression directly in BM progenitor cells to determine consequences in angiogenesis-mediated tumor growth. Short hairpin RNAs (shRNAs) targeting Id1 were designed, and tested for effectiveness using a method developed previously in the laboratory (Kumar et al., *Genome Res* 13, 2333 (2003)). We designed a potent shRNA that effectively reduced endogenous Id1 mRNA and protein levels by >95% (FIG. 32 left). To stably deliver these shRNAs to the progenitor cells, we first generated lentiviral vectors encoding non-specific shRNA or Id1-specific shRNA with a GFP reporter under a constitutive promoter (FIG. 31A, top left). BM-derived Lin$^-$ progenitor cells were transduced ex vivo with the lentiviral vector encoding either the Id1-specific shRNA or a non-specific shRNA. Flow cytometry analysis of a small portion of transduced cells showed >90% transduction. Animals were allowed to reconstitute for 4 weeks after BM transplantation, and LLC cells were implanted. Their growth was measured for 2 weeks to determine the impact of the suppression of Id1 gene expression. There was a pronounced delay in the appearance of LLC tumors and slower tumor growth in Id1 shRNA-BMT mice compared with that of non-specific shRNA-BMT mice (>60% by day 14; FIG. 31A, bottom left). Similar results were obtained with B6RV2 lymphomas (FIG. 35). The tumors in non-specific (NS) shRNA-BMT mice were larger and appeared to be highly vascularized (red tumors), as compared to the relatively smaller pale tumors, observed in the Id1 shRNA-BMT mice (FIG. 31A, top right). In addition, the tumors in Id1-specific shRNA-BMT mice showed a dramatic reduction in vascular density as compared to non-specific shRNA-BMT (FIG. 31A, top right), suggesting that vasculature defects in Id1 shRNA-BMT is the major cause for reduced tumor growth. Notably, stable suppression (>100 fold) of Id1 mRNA in vivo in BM cells, 6 weeks post BMT, was observed, while suppression of Id1 did not affect normal hematopoiesis (levels of pan hematopoietic mRNA, CD45, remained relatively unchanged; FIG. 31A, bottom right).

Encouraged by these results, we repeated the experiment, this time limiting expression of shRNA specifically to the EPCs by placing shRNA expression under control of the Id1 proximal promoter (Id1pr/p; FIG. 31C). In addition, we sought to determine how suppressing VEGFR2/flk1 (another EPC marker gene that's upregulated during tumor challenge) affects tumor growth, and designed a shRNA that effectively suppressed VEGFR2 expression (FIG. 32, right). We generated animals reconstituted with transduced BM expressing VEGFR2/flk1 shRNA, Id1 shRNA or non-specific (NS) shRNA under control of the Id1 promoter (FIG. 13B, top). After LLC tumor challenge, Id1 or VEGFR2 suppression in EPCs resulted in reduced EPC mobilization compared to controls, indicated by reduced circulating EPC (VEGFR2$^+$ or VE-cadherin$^+$) in peripheral blood (FIG. 31C, top), although no change was observed in either GR1$^+$ neutrophils or CD45$^+$ hematopoietic cells. Both Id1 and VEGFR2 suppression further resulted in reduced tumor vessel density (FIG. 31D). Most importantly, tumor growth was impaired in both VEGFR2 and Id1 shRNA BMT animals compared with NS shRNA BMT animals (FIG. 32B), demonstrating that suppressing these genes specifically in EPCs is sufficient for reducing angiogenesis-mediated tumor growth.

What is claimed is:

1. A method of inhibiting tumor growth in a subject, comprising isolating Endothelial Progenitor Cells (EPCs) from the subject, conjugating to the isolated EPCs a cancer therapeutic agent, and implanting the conjugated cells to the subject, wherein the EPCs are VE-cadherin$^+$ VEGFR2$^+$ CD31$^{low}$ Endoglin$^+$ Prominin I/AC 133$^+$ CXCR4$^+$ VLA4$^+$ c-kit$^+$.

2. The method of claim 1, wherein the EPCs are isolated from the subject by flow-cytometry-based cell sorting, magnetic cell sorting, and/or antibody panning.

3. The method of claim 1, wherein the EPCs are isolated from the bone marrow, peripheral blood, or cord blood of the subject.

4. A composition of substantially purified population of human EPCs, wherein the EPCs are isolated from the bone marrow, peripheral blood, or cord blood of a subject, and wherein a cancer therapeutic agent is conjugated to the EPCs and the EPCs are VE-cadherin$^+$ VEGFR2$^+$ CD31$^{low}$ Endoglin$^+$ Prominin I/AC 133$^+$ CXCR4$^+$ VLA4$^+$ c-kit$^+$.

5. A method of inhibiting progression of micro-metastases to macro-metastases in a subject, comprising implanting autologous endothelial progenitor cells (EPCs) conjugated to an anti-cancer therapeutic agent to the subject, wherein the EPCs are VE-cadherin$^+$ VEGFR2$^+$ Endoglin$^+$ Prominin I/AC 133$^+$ CXCR4$^+$ VLA4$^+$ c-kit$^+$.

6. The method of claim 5, wherein Endothelial Progenitor Cells (EPCs) are isolated from the subject, conjugated to a cancer therapeutic agent and the conjugated cells are implanted to the subject.

7. The method of claim 6, wherein the EPCs are isolated from the subject by flow-cytometry-based cell sorting, magnetic cell sorting, and/or antibody panning.

8. The method of claim 6, wherein the EPCs are isolated from the bone marrow, peripheral blood, or cord blood of the subject.

* * * * *